US012384832B2

(12) United States Patent
Oelkrug et al.

(10) Patent No.: US 12,384,832 B2
(45) Date of Patent: Aug. 12, 2025

(54) ANTIBODY-MEDIATED NEUTRALIZATION OF BETA-LACTAMASES

(71) Applicants: Christopher Roland Oelkrug, Rottenburg am Neckar (DE); Andreas Bernhard Joachim Schubert, Leipzig (DE)

(72) Inventors: Christopher Roland Oelkrug, Rottenburg am Neckar (DE); Andreas Bernhard Joachim Schubert, Leipzig (DE)

(73) Assignees: Christopher Oelkrug, Rottenburg am Neckar (DE); Andreas Schubert, Leipzig (DE)

( * ) Notice: Subject to any disclaimer, the term of this patent is extended or adjusted under 35 U.S.C. 154(b) by 647 days.

(21) Appl. No.: 17/596,652

(22) PCT Filed: Jun. 19, 2019

(86) PCT No.: PCT/IB2019/055189
§ 371 (c)(1),
(2) Date: Dec. 15, 2021

(87) PCT Pub. No.: WO2020/254861
PCT Pub. Date: Dec. 24, 2020

(65) Prior Publication Data
US 2023/0340086 A1    Oct. 26, 2023

(51) Int. Cl.
| | |
|---|---|
| A61K 38/04 | (2006.01) |
| A61K 45/06 | (2006.01) |
| A61P 31/04 | (2006.01) |
| C07K 16/12 | (2006.01) |
| A61K 39/00 | (2006.01) |

(52) U.S. Cl.
CPC .......... *C07K 16/1203* (2013.01); *A61K 45/06* (2013.01); *A61P 31/04* (2018.01); *A61K 2039/55566* (2013.01); *A61K 2039/6018* (2013.01); *A61K 2039/6081* (2013.01)

(58) Field of Classification Search
None
See application file for complete search history.

(56) References Cited

U.S. PATENT DOCUMENTS

| | | |
|---|---|---|
| 4,816,397 A | 3/1989 | Boss et al. |
| 4,816,567 A | 3/1989 | Cabilly et al. |
| 4,975,369 A | 12/1990 | Beavers et al. |
| 4,978,775 A | 12/1990 | Ikegami et al. |

FOREIGN PATENT DOCUMENTS

| | | |
|---|---|---|
| WO | WO 1993/006213 | 4/1993 |
| WO | WO 2008/095222 | 8/2008 |

OTHER PUBLICATIONS academic.oup.com, "UniProt: the universal protein knowledgebase," Nucleic Acids Research, Jan. 2017, 45(D1):D158-D169.
Adachi et al., "Site-directed mutants, at position 166, of RTEM-1 beta-lactamase that form a stable acyl-enzyme intermediate with penicillin," Journal of Biological Chemistry, Feb. 15, 1991, 266(5):3186-91.
Arimitsu et al., "Evaluation of Shiga toxin 2e-specific chicken egg yolk immunoglobulin: Production and neutralization activity," Microbiology and Immunology, Nov. 2014, 58(11):643-8.
Atanasov et al., "Protonation of the β-lactam nitrogen is the trigger event in the catalytic action of class A β-lactamases," Proceedings of the National Academy of Sciences, Mar. 28, 2000, 97(7):3160-5.
Berman et al., "The protein data Bank," Nucleic Acids Research, Jan. 2000, 28(1):235-42.
Bollen et al., "Immunoglobulin G in the developing oocytes of the domestic hen and immunospecific antibody response in serum and corresponding egg yolk," In Vivo, Sep. 1, 1997, 11(5):395-8.
Bouthers et al., "Role of residues 104, 164, 166, 238 and 240 in the substrate profile of PER-1 β-lactamase hydrolysing third-generation cephalosporins," Biochemical Journal, Mar. 15, 1998, 330(3):1443-9.
Bradford, "Extended-spectrum β-lactamases in the 21st century: characterization, epidemiology, and detection of this important resistance threat," Clinical Microbiology Reviews, Oct. 1, 2001, 14(4):933-51.
Brandt et al., "In silico serine β-lactamases analysis reveals a huge potential resistome in environmental and pathogenic species." Scientific Reports, Feb. 24, 2017, 7(1), 13 pages.
Brown et al., "Structural and biochemical evidence that a TEM-1 β-lactamase N170G active site mutant acts via substrate-assisted catalysis," Journal of Biological Chemistry, Nov. 27, 2009, 284(48):33703-12.
Bush et al., "Epidemiological expansion, structural studies, and clinical challenges of new β-lactamases from gram-negative bacteria," Annual Review of Microbiology, Oct. 13, 2011, 65:455-78.
Bush et al., "Updated functional classification of β-lactamases," Antimicrobial Agents and Chemotherapy, Mar. 2010, 54(3):969-76.
Calzado et al., "Human haemoclassification by use of specific yolk antibodies obtained after immunisation of chickens against human blood group antigens," Alternatives to Laboratory Animals, Nov. 2001, 29(6):717-26.
Casewell et al., "The European ban on growth-promoting antibiotics and emerging consequences for human and animal health," Journal of Antimicrobial Chemotherapy, Aug. 1, 2003, 52(2):159-61.
Chalghoumi et al., "Adhesion and growth inhibitory effect of chicken egg yolk antibody (IgY) on *Salmonella enterica* serovars Enteritidis and Typhimurium in vitro," Foodborne Pathogens and Disease, Jun. 1, 2009, 6(5):593-604.

(Continued)

*Primary Examiner* — Jennifer E Graser
(74) *Attorney, Agent, or Firm* — Fish & Richardson P.C.

(57) ABSTRACT

Provided herein are antibodies, such as immunoglobulins Y (IgY) antibodies that inhibit beta-lactamase activity, e.g., TEM-1 beta-lactamase, as well as related compositions and methods of use thereof to treat infections by lactam-based antibiotic bacteria that produce beta-lactamase that can degrade antibiotics.

5 Claims, 13 Drawing Sheets
(12 of 13 Drawing Sheet(s) Filed in Color)
Specification includes a Sequence Listing.

(56) References Cited

OTHER PUBLICATIONS

Chang et al., "Productivity and Some Properties of Immunoglobulin Specific against *Streptococcus mutans* Serotype c in Chicken Egg Yolk (IgY)," Journal of Agricultural and Food Chemistry, Jan. 18, 1999, 47(1):61-6.

Chen et al., "A 6× 6 drop plate method for simultaneous colony counting and MPN enumeration of Campylobacter jejuni, Listeria monocytogenes, and *Escherichia coli*," Journal of Microbiological Methods, Nov. 1, 2003, 55(2):475-9.

Chen et al., "Structure and kinetics of the B-lactamase mutants S70A and K73H from *Staphylococcus aureus* PC1," Biochemistry, Sep. 24, 1996, 35(38):12251-8.

Conrath et al., "β-Lactamase inhibitors derived from single-domain antibody fragments elicited in the camelidae," Antimicrobial Agents and Chemotherapy, Oct. 1, 2001, 45(10):2807-12.

Cook et al., "IgY-Immune component of eggs as a source of passive immunity for animals and humans," World's Poultry Science Journal, Jun. 2010, 66(2):215-26.

Damblon et al., "The catalytic mechanism of beta-lactamases: NMR titration of an active-site lysine residue of the TEM-I enzyme," Proceedings of the National Academy of Sciences, Mar. 5, 1996, 93(5):1747-52.

Datta et al., "Penicillinase synthesis controlled by infectious R factors in Enterobacteriaceae," Nature, Oct. 16, 1965, 208:239-41.

Economou et al., "Agriculture and food animals as a source of antimicrobial-resistant bacteria," Infection and Drug Resistance, Apr. 2015;8:49-61.

Erhard et al., "Adjuvant effects of various lipopeptides and interferon-γ on the humoral immune response of chickens," Poultry Science, Sep. 1, 2000, 79(9):1264-70.

Fertey et al., "Pathogens inactivated by low-energy-electron irradiation maintain antigenic properties and induce protective immune responses," Viruses, Nov. 23, 2016, 8(11):319, 14 pages.

Fisette et al., "TEM-1 backbone dynamics—insights from combined molecular dynamics and nuclear magnetic resonance," Biophysical Journal, Feb. 17, 2010, 98(4):637-45.

Furnham et al., "The Catalytic Site Atlas 2.0: cataloging catalytic sites and residues identified in enzymes," Nucleic Acids Research, Jan. 1, 2014, 42(DI):D485-9.

Golemi-Kotra et al., "The importance of a critical protonation state and the fate of the catalytic steps in class A β-lactamases and penicillin-binding proteins," Journal of Biological Chemistry, Aug. 13, 2004. 279(33):34665-73.

Goossens et al., "Outpatient antibiotic use in Europe and association with resistance: a cross-national database study, " The Lancet, Feb. 12, 2005, 365(9459):579-87.

Guimarães et al., "Growth inhibition of *Staphylococcus aureus* by chicken egg yolk antibodies." Archivum Immunologiae et Therapiae Experimentalis, Oct. 2009, 57(5):377-82.

Gürtler et al., "Effect of orally administered egg yolk antibodies on *Salmonella enteritidis* contamination of hen's eggs," Journal of Veterinary Medicine, Series B, Apr. 2004, 51(3):129-34.

Hart et al., "Modelling proteins' hidden conformations to predict antibiotic resistance," Nature Communications, Oct. 6, 2016, 7(1):1-0.

Hatta et al., "Passive immunization against dental plaque formation in humans: effect of a mouth rinse containing egg yolk antibodies (IgY) specific to *Streptococcus mutans*," Caries Research, 1997, 31(4):268-74.

Hedlund et al., "Oral immunisation of chickens using cholera toxin B subunit and Softigen (R) as adjuvants results in high antibody titre in the egg yolk, " In Vivo, 2001; 15(5):381-4.

Holliger et al., "Diabodies": small bivalent and bispecific antibody fragments, Proceedings of the National Academy of Sciences, Jul. 15, 1993, 90(14):6444-8.

Horie et al., "Suppressive effect of functional drinking yogurt containing specific egg yolk immunoglobulin on Helicobacter pylori in humans," Journal of Dairy Science, Dec. 1, 2004, 87(12):4073-9.

Hsieh et al., "Recombinant outer membrane protein A fragments protect against *Escherichia coli* meningitis," Journal of Microbiology, Immunology and Infection, Jun. 1, 2016, 49(3):329-34.

Huston et al., "Protein engineering of antibody binding sites: recovery of specific activity in an anti-digoxin single-chain Fv analogue produced in *Escherichia coli*," Proceedings of the National Academy of Sciences, Aug. 1988, 85(16):5879-83.

Imberechts et al., "Chicken egg yolk antibodies against F18ab fimbriae of *Escherichia coli* inhibit shedding of F18 positive *E. coli* by experimentally infected pigs," Veterinary Microbiology, Mar. 1, 1997, 54(3-4):329-41.

Jacoby et al., "More extended-spectrum beta-lactamases," Antimicrobial Agents and Chemotherapy, Sep. 1991, 35(9):1697-704.

Jacoby, "Extrachromosomal resistance in Gram-negative organisms: the evolution of β-lactamase," Trends in Microbiology, Oct. 1, 1994, 2(10):357-60.

Jelsch et al., "Crystal structure of *Escherichia coli* TEMI β-lactamase at 1,8 Å resolution," Proteins: Structure, Function, and Bioinformatics, Aug. 1993, 16(4):364-83.

Jin et al., "In vitro inhibition of adhesion of enterotoxigenic *Escherichia coli* K88 to piglet intestinal mucus by egg-yolk antibodies," FEMS Immunology & Medical Microbiology, Aug. 1, 1998, 21(4):313-21.

Jones et al., "Replacing the complementarity-determining regions in a human antibody with those from a mouse," Nature, May 1986, 321(6069):522-5.

Kijanka et al., "Nanobody-based cancer therapy of solid tumors," Nanomedicine, Jan. 2015, 10(1):161-74.

Kink et al., "Antibodies to recombinant Clostridium difficile toxins A and B are an effective treatment and prevent relapse of C. difficile-associated disease in a hamster model of infection," Infection and Immunity, May 1, 1998, 66(5):2018-25.

Köhler et al., "Continuous cultures of fused cells secreting antibody of predefined specificity," Nature, Aug. 1975, 256(5517):495-7.

Kollberg et al., "Oral administration of specific yolk antibodies (IgY) may prevent Pseudomonas aeruginosa infections in patients with cystic fibrosis: a phase I feasibility study," Pediatric Pulmonology, Jun. 2003, 35(6):433-40.

Kovacs-Nolan et al., "Egg yolk antibodies for passive immunity," Annual Review of Food Science and Technology, Apr. 2012, 3:163-82.

Kovacs-Nolan et al., "Microencapsulation for the gastric passage and controlled intestinal release of immunoglobulin Y," Journal of Immunological Methods, Jan. 2005, 296(1-2):199-209.

Kovaleva et al., "Shark variable new antigen receptor biologics—a novel technology platform for therapeutic drug development," Expert Opinion on Biological Therapy, Oct. 1, 2014, 14(10):1527-39.

Kozbor et al., "The production of monoclonal antibodies from human lymphocytes," Immunology Today, Mar. 1, 1983, 4(3):72-9.

Krüger et al., "The effects of egg-derived antibodies to glucosyltransferases on dental caries in rats," Caries Research, Jan. 2004, 38(1):9-14.

Lamotte-Brasseur et al., "Mechanism of acyl transfer by the class A serine β-lactamase of Streptomyces albus G," Biochemical Journal, Oct. 1, 1991, 279(1):213-21.

Lee et al., "Acid Stability of Anti-Helicobacter pyroli IgY in in Aqueous Polyol Solution," BMB Reports, 2002, 35(5):488-93.

Lee et al., "Evaluation of the heat inactivation of *Escherichia coli* and Lactobacillus plantarum by differential scanning calorimetry," Applied and Environmental Microbiology, Nov. 2002, 68(11):5379-86.

Leslie et al., "Phylogeny of immunoglobulin structure and function: III. Immunoglobulins of the chicken," The Journal of Experimental Medicine, Dec. 1, 1969, 130(6):1337-52.

Leung et al., "Site-directed mutagenesis of β-lactamase I: role of Glu-166," Biochemical Journal, May 1, 1994, 299(3):671-8.

Li et al., "Chitosan-Alginate Microcapsules for Oral Delivery of Egg Yolk Immunoglobulin (IgY): Effects of Chitosan Concentration," Applied Biochemistry and Biotechnology, Dec. 2009, 159(3):778-87.

Mackey et al., "Thermal denaturation of whole cells and cell components of *Escherichia coli* examined by differential scanning calorimetry," Microbiology, Oct. 1, 1991, 137(10):2361-74.

(56) References Cited

OTHER PUBLICATIONS

Malekshahi et al., "Treatment of Helicobacter pylori infection in mice with oral administration of egg yolk-driven anti-UreC immunoglobulin," Microbial Pathogenesis, Nov. 1, 2011, 51(5):366-72.
Marquardt et al., "Passive protective effect of egg-yolk antibodies against enterotoxigenic *Escherichia coli* K88+ infection in neonatal and early-weaned piglets," FEMS Immunology & Medical Microbiology, Apr. 1, 1999, 23(4):283-8.
Marshall et al., "Food animals and antimicrobials: impacts on human health," Clinical Microbiology Reviews, Oct. 2011, 24(4):718-33.
Medeiros, "Cooperative evolution of mechanisms of β-lactam resistance," Clinical Microbiology and Infection, Jan. 1, 2000, 6:27-33.
Meneksedag et al., "Communication between the active site and the allosteric site in class A beta-lactamases," Computational Biology and Chemistry, Apr. 1, 2013, 43:1-0.
Merouch et al., "Ab initio QM/MM study of class A β-lactamase acylation: dual participation of Glu166 and Lys73 in a concerted base promotion of Ser70," Journal of the American Chemical Society, Nov. 9, 2005, 127(44):15397-407.
Minasov et al., "An ultrahigh resolution structure of TEM-1 β-lactamase suggests a role for Glu166 as the general base in acylation," Journal of the American Chemical Society, May 15, 2002, 124(19):5333-40.
Mine et al., "Chicken egg yolk antibodies as therapeutics in enteric infectious disease: a review," Journal of Medicinal Food, Sep. 1, 2002, 5(3):159-69.
Morin et al., "Monoclonal antibodies to TEM-1 plasmid-mediated beta-lactamase," Antimicrobial Agents and Chemotherapy, Nov. 1987. 31(11):1761-7.
Motoi et al., "Production of rabies neutralizing antibody in hen's eggs using a part of the G protein expressed in *Escherichia coli*," Vaccine, Apr. 27, 2005, 23(23):3026-32.
Müller et al., "IgY antibodies in human nutrition for disease prevention," Nutrition Journal, Dec. 2015, 14(1):1-7.
Naas et al., "Beta-lactamase database (BLDB)—structure and function," Journal of Enzyme Inhibition and Medicinal Chemistry, Jan. 1, 2017, 32(1):917-9.
Nguyen et al., "Anti-cell-associated glucosyltransferase immunoglobulin Y suppression of salivary mutans streptococci in healthy young adults," The Journal of the American Dental Association, Aug. 1, 2011, 142(8):943-9.
Orlandi et al., "Cloning immunoglobulin variable domains for expression by the polymerase chain reaction," Proceedings of the National Academy of Sciences, May 1989, 86(10):3833-7.
Pavelka et al., "HotSpot Wizard: a web server for identification of hot spots in protein engineering," Nucleic Acids Research, Jul. 1, 2009, 37(suppl 2):W376-83.
PCT International Preliminary Report on Patentability in International Appln. No. PCT/IB2019/055189, dated Dec. 21, 2021 8 pages.
PCT International Search Report and Written Opinion in International Appln. No. PCT/IB2019/055189, dated Mar. 9, 2020.
Petrosino et al., "Systematic mutagenesis of the active site omega loop of TEM-1 beta-lactamase," Journal of Bacteriology, Apr. 1996, 178(7):1821-8.
Pettersen et al., "UCSF Chimera—a visualization system for exploratory research and analysis," Journal of Computational Chemistry, Oct. 2004, 25(13):1605-12.
Pimenta et al., "Evolution of drug resistance: insight on TEM β-lactamases structure and activity and β-lactam antibiotics," Mini Reviews in Medicinal Chemistry, Feb. 1, 2014, 14(2):111-22.
Poyart et al., "A novel extended-spectrum TEM-type β-lactamase (TEM-52) associated with decreased susceptibility to moxalactam in Klebsiella pneumoniae," Antimicrobial Agents and Chemotherapy, Jan. 1, 1998, 42(1):108-13.
Queen et al., "A humanized antibody that binds to the interleukin 2 receptor," Proceedings of the National Academy of Sciences, Dec. 1989, 86(24):10029-33.

Rahman et al., "Oral passive IgY-based immunotherapeutics: a novel solution for prevention and treatment of alimentary tract diseases," Human Vaccines & Immunotherapeutics, May 14, 2013, 9(5):1039-48.
Rousseaux et al., "Optimal conditions for the preparation of proteolytic fragments from monoclonal IgG of different rat IgG subclasses," Methods in Enzymology, Jan. 1986, 121, 663-9.
Salverda et al., "Natural evolution of TEM-1 β-lactamase: experimental reconstruction and clinical relevance," FEMS Microbiology Reviews, Nov. 1, 2010, 34(6):1015-36.
Schade et al., "Chicken egg yolk antibodies (IgY-technology): a review of progress in production and use in research and human and veterinary medicine," Alternatives to Laboratory Animals, Apr. 2005, 33(2):129-54.
Schade et al., "Polyclonal IgY antibodies from chicken egg yolk—an alternative to the production of mammalian IgG type antibodies in rabbits," Alternatives to Laboratory Animals, Oct. 1991, 19(4):403-19.
Schade et al., "Production of Avian (Egg Yolk) Antibodies: IgY: The Report and Recommendations of ECVAM Workshop 211, 2," Alternatives to Laboratory Animals, Dec. 1996, 24(6):925-34.
Schade et al., "Specificity of chicken (IgY) versus rabbit (IgG) antibodies raised against cholecystokinin octapeptide (CCK-8)," ALTEX-Alternatives to Animal Experimentation, Jan. 1, 1996, 13(Suppl):80-5.
Shallcross et al., "Antibiotic overuse: a key driver of antimicrobial resistance," British Journal of General Practice, Dec. 1, 2014, 64(629):604-5.
Shin et al., "Production of anti-Helicobacter pylori urease-specific immunoglobulin in egg yolk using an antigenic epitope of H. pylori urease," Journal of Medical Microbiology, Jan. 1, 2004, 53(1):31-4.
Shin et al., "Use of egg yolk-derived immunoglobulin as an alternative to antibiotic treatment for control of Helicobacter pylori infection," Clinical and Vaccine Immunology, Sep. 2002, 9(5):1061-6.
Song et al., "Growth inhibition of clostridium perfringens vegetative cells and spores using chicken immunoglobulin Y," Journal of Food Safety, Nov. 2009, 29(4):511-20.
Spillner et al., "Avian IgY antibodies and their recombinant equivalents in research, diagnostics and therapy," Biologicals, Sep. 1, 2012, 40(5):313-22.
Stojanoski et al., "A triple mutant in the Ω-loop of TEM-1 β-lactamase changes the substrate profile via a large conformational change and an altered general base for catalysis," Journal of Biological Chemistry, Apr. 17, 2015, 290(16):10382-94.
Strynadka et al., "Molecular structure of the acyl-enzyme intermediate in β-lactam hydrolysis at 1.7 Å resolution," Nature, Oct. 1992, 359(6397):700-5.
Sugita-Konishi et al., "Immune functions of immunoglobulin Y isolated from egg yolk of hens immunized with various infectious bacteria," Bioscience, Biotechnology, and Biochemistry, Jan. 1, 1996, 60(5):886-8.
Sun et al., "Effect of four adjuvants on immune response to F4 fimbriae in chickens," Veterinary Immunology and Immunopathology, Jan. 15, 2008, 121(1-2):107-12.
Sunwoo et al., "Growth inhibition of Escherichia coli 987P by neutralizing IgY antibodies," The Open Immunology Journal, Jan. 20, 2010, 3(1).
Suzuki et al., "Effect of dietary anti-Helicobacter pylori-urease immunoglobulin Y on Helicobacter pylori infection," Alimentary Pharmacology & Therapeutics, Jul. 2004, 20:185-92.
Timbrook et al., "Assessments of opportunities to improve antibiotic prescribing in an emergency department: a period prevalence survey," Infectious Diseases and Therapy, Dec. 2017, 6(4):497-505.
Tini et al., "Generation and application of chicken egg-yolk antibodies," Comparative Biochemistry and Physiology Part A: Molecular & Integrative Physiology, Mar. 1, 2002, 131(3):569-74.
Tobias et al., "Growth inhibition of *Staphylococcus aureus* and *Escherichia coli* strains by neutralizing IgY antibodies from ostrich egg yolk," Brazilian Journal of Microbiology, Jun. 2012, 43:544-51.
Trott et al., "Egg yolk antibodies for detection and neutralization of Clostridium botulinum type A neurotoxin," Journal of Food Protection, May 2009, 72(5):1005-11.

(56) References Cited

OTHER PUBLICATIONS

Vandavasi et al., "Active-site protonation states in an acyl-enzyme intermediate of a class A β-lactamase with a monobactam substrate," Antimicrobial Agents and Chemotherapy, Jan. 1, 2017, 61(1):e01636-16.

Vandavasi et al., "Exploring the mechanism of β-lactam ring protonation in the class A β-lactamase acylation mechanism using neutron and X-ray crystallography," Journal of Medicinal Chemistry, Jan. 14, 2016, 59(1):474-9.

Vincke et al., "Introduction to heavy chain antibodies and derived Nanobodies," Single Domain Antibodies, Jan. 2012, 15-26.

Wesolowski et al., "Single domain antibodies: promising experimental and therapeutic tools in infection and immunity," Medical Microbiology and Immunology, Aug. 2009, 198(3):157-74.

Wilhelmson et al., "Oral treatment with yolk antibodies for the prevention of C. albicans infections in chemotherapy treated children. A feasibility study," Food and Agricultural Immunology, Mar. 1, 2005, 16(1):41-5.

Xu et al., "Application of chicken egg yolk immunoglobulins in the control of terrestrial and aquatic animal diseases: a review," Biotechnology Advances, Nov. 1, 2011, 29(6):860-8.

Xun et al., "Protective effects of sucralfate on anti-H. pylori VacA IgY in vivo and in vitro," African Journal of Microbiology Research, Jun. 4, 2010, 4(11):1091-9.

Yokoyama et al., "Effects of egg yolk antibody against Porphyromonas gingivalis gingipains in periodontitis patients," Journal of Oral Science, 2007, 49(3):201-6.

Zajac et al., "IgY antibodies against bacterial infection—Development of candidate IgY antibodies against ESBL-producing gram-negative bacteria for oral therapy," Jun. 20, 2018, retrived from URL <https://ul.qucosa.de/api/qucosa%3A21529/attachment/ATT-0/> on Aug. 5, 2022, 137 pages.

Zajac et al., "IgY antibodies against bacterial infection," Publikationsserver der Universitat Leipzig, Jun. 20, 2018, retrieved from URL <https://nbn-resolving.org/urn:nbn:de:bsz:15-qucosa2-215293> on Aug. 5, 2022, 2 pages (English abstract).

Zhen et al., "Characterization of specific egg yolk immunoglobulin (IgY) against mastitis-causing *Escherichia coli*," Veterinary Microbiology, Jul. 27, 2008, 130(1-2):126-33.

Zhen et al., "Efficacy of specific egg yolk immunoglobulin (IgY) to bovine mastitis caused by *Staphylococcus aureus*," Veterinary Microbiology, Feb. 2, 2009, 133(4):317-22.

ANTIBODY-MEDIATED NEUTRALIZATION OF BETA-LACTAMASES

CLAIM OF PRIORITY

This application is a U.S. National Phase Application under 35 U.S.C. § 371 of International Patent Application No. PCT/IB2019/055189, filed on Jun. 19, 2019. The entire contents of the foregoing are hereby incorporated by reference.

SEQUENCE LISTING

The instant application contains a Sequence Listing which has been submitted electronically in ASCII format and is hereby incorporated by reference in its entirety. The ASCII text file, created on Apr. 21, 2022, is named Sequence_Listing.txt and is 10 kilobytes in size.

TECHNICAL FIELD

The present disclosure relates generally to the fields of enzyme inhibition and treatment of infectious diseases. More specifically, the present disclosure relates to the use of antibodies and antigen-binding fragments to neutralize beta-lactamase to treat infections by antibiotic-resistant bacteria.

BACKGROUND

Antibiotics play a very important role in agriculture and are widely used in livestock for growth control, disease prevention and treatment (Economou et al., *Infect. Drug Resist.* 2015, 8:49-61; and Marshall et al., *Clin. Microbiol. Rev.* 2011, 24:718-733). Even though the use of antibiotic growth promoters is banned in the European Union and its use in the United States has been relatively minimalized, antibiotics are still extensively used in other regions of the world (Casewell et al., *J. Antinicrob. Chemother.* 2003, 52:159-161). Up to 90% of antibiotics are prescribed as a standard of care, even against common, non-serious infections, such as, for example, sore throat (Goossens et al., *Lancet* 2005, 265:579-587; and Shallcross et al., *Br. J. Gen. Pract.* 2014, 64:604-605). According to recent statistics, 30% of antibiotic treatments are prescribed to patients inappropriately (Timbrook et al., *Infect. Dis. Ther.* 2017, 6:497-505). As a result, the increasing use of antimicrobials, including antibiotics, has led to bacterial resistance becoming a major threat to public health.

Extended Spectrum Beta-Lactamases (ESBL) are a group of antibiotic-resistant bacteria that are strongly related to Gama Proteobacteria class, especially to Enterobacteriaceae family including species such as *E. coli* and *Klebsiella* (Brandt et al., *Sci. Rep.* 2017, 7:43232). Among gram-negative bacteria, the mostly identified types of ESBLs are TEM/SHV or CTX-M, which are constitutively synthesized and secreted in the periplasmic space.

With the ever-growing development of new resistant-bacterial strains, the perspective of establishing a universal antibody-based immunotherapeutic targeting ESBL-producing bacteria is a very promising alternative to current antibiotic treatments.

SUMMARY

The disclosure is based, at least in part, on the discovery that antibodies (e.g., IgY) directed against the active site omega loop of beta-lactamase enzymes (e.g., TEM (e.g., TEM-1) and antibodies (e.g., IgY) directed against inactivated (e.g., by e-beam) bacteria that produce beta-lactamase (e.g., beta-lactamase producing *E. coli* (e.g., TEM-1-producing *E. coli*)) can be used alone or in combination with at least one antibiotic (e.g., any beta-lactam antibiotics) to treat bacterial infections (e.g., infections by beta-lactamase-producing bacteria (e.g., infections by TEM-1-producing bacteria (e.g., infections by TEM-1-producing *E. coli*)) in (e.g., an avian subject, a mammalian subject (e.g., a human subject)).

In one aspect, the disclosure features antigen compositions including a peptide conjugated to an adjuvant, wherein the peptide comprises any one of:

| | |
|---|---|
| RFPMMSTFKVL | (SEQ ID NO: 1) |
| TRLDRWEPELN | (SEQ ID NO: 2) |
| FPMMSTFKVL | (SEQ ID NO: 3) |
| TRLDRWEPELN | (SEQ ID NO: 4) |
| TRLDSWEPELN | (SEQ ID NO: 5) |
| TRLDHWEPELN | (SEQ ID NO: 6) |
| RLDRWEPDLN | (SEQ ID NO: 7) |
| TRLDRWETELN | (SEQ ID NO: 8) |
| TRLDRYEPELN | (SEQ ID NO: 9) |
| TRLDRIEPDLN | (SEQ ID NO: 10) |
| SRLDRWETELN | (SEQ ID NO: 11) |
| RFPMMSTFKVM | (SEQ ID NO: 12) |
| RFPMMSTFKVI | (SEQ ID NO: 13) |
| RFPMMSTFKVV | (SEQ ID NO: 14) |
| RFPLMSTFKVL | (SEQ ID NO: 15) |
| RFPMMSTFKTL | (SEQ ID NO: 16) |
| RFPMLSTFKVL | (SEQ ID NO: 17) |
| RFPMISTFKVL | (SEQ ID NO: 18) |
| RFPMVSTFKVL | (SEQ ID NO: 19) |
| RFPIMSTFKVL | (SEQ ID NO: 20) |
| RFPMMNTFKVV | (SEQ ID NO: 21) |

-continued

RFPMLSTFKVV (SEQ ID NO: 22)

RFPMCSTFKVL (SEQ ID NO: 23)

RFPLMSTFKTL (SEQ ID NO: 24)

RFPLMSTFKAL (SEQ ID NO: 25)

RFPMVSTFKVV (SEQ ID NO: 26)

FPMMSTFKVV (SEQ ID NO: 27)

RFPVVSTFKVL (SEQ ID NO: 28)

RFPMCSTFKLL (SEQ ID NO: 29)

RFPMASTFKAL (SEQ ID NO: 30)

RFPMCSTFKTL (SEQ ID NO: 31)

RFPLCSTFKVM (SEQ ID NO: 32)

IADKSGAGERG (SEQ ID NO: 33)

IADKTGAGERG (SEQ ID NO: 34)

IADKSGTGERG (SEQ ID NO: 35)

IADKSGAGKRG (SEQ ID NO: 36)

IADKSGASERG (SEQ ID NO: 37)

IADKSGAGRRG (SEQ ID NO: 38)

IADKSGANERG (SEQ ID NO: 39)

IADKAGAGERG (SEQ ID NO: 40)

IADKSGADERG (SEQ ID NO: 41)

IADRTGAGERG (SEQ ID NO: 42)

IADKSGAGVRG (SEQ ID NO: 43)

IADKSGTGKRG (SEQ ID NO: 44)

IADKTGAGARG (SEQ ID NO: 45)

IADKTGAGKRG (SEQ ID NO: 46)

TRLGRWEPELN (SEQ ID NO: 47)

RLDRWEVELN (SEQ ID NO: 48)

RLDRWELELN (SEQ ID NO: 49)

TRLDRIEPDLN (SEQ ID NO: 50)

$X_1RLDX_2X_3EX_4X_5LN$, (SEQ ID NO: 51)

in which $X_1$ is T or S or omitted, $X_2$ is R, S, or I, $X_3$ is W, Y, or I, $X_4$ is P or T, and $X_5$ is E or D.

In some embodiment, the adjuvant or carrier includes one or more of bovine serum albumin (BSA), keyhole limpet hemocyanin (KLH), *Concholepas concholepas* hemocyanin (CCH), ovalbunin (OVA), Freund's complete adjuvant (FCA), Freund's incomplete adjuvant (FIA), specol, and lipopeptide Pam3Cys-Ser-(Lys)4 (PCSL).

In some embodiments, the peptide comprises RFPMMSTFKVL (SEQ ID NO: 1) or TRLDRWEPELN (SEQ ID NO: 2) or $X_1RLDX_2X_3EX_4X_5LN$ (SEQ ID NO: 51), in which $X_1$ is T or S or omitted, $X_2$ is R, S, or H $X_3$ is W, Y, or I, $X_4$ is P or T, and $X_5$ is E or D.

In another aspect, the disclosure provides antibodies or an antigen-binding fragments thereof, wherein the antibody or the antigen-binding fragment specifically binds to an omega loop of the active site of a beta-lactamase enzyme and inhibits the destruction of a beta-lactam antibiotic. For example, the antibody or the antigen-binding fragment specifically binds to an antigen corresponding to an omega loop of the active site of a beta-lactamase enzyme.

In some embodiments, the antibody or the antigen-binding fragment specifically binds to an antigen composition described herein. For example, the antibody or antigen-binding fragment can be selected from the group consisting of a polyclonal antibody, a monoclonal antibody, a chimeric antibody, a CDR-grafted antibody, a humanized antibody, a Fab fragment, a Fab' F (from') 2 fragment, an Fv fragment, a disulfide linked Fv fragment, an scFv fragment, a single domain antibody, a diabody, a multi-specific antibody, a dual-specific antibody, and a bispecific antibody.

In certain embodiments, the antibody or antigen-binding fragment is an IgY antibody or fragment. The antibody or antigen-binding fragment can be a monoclonal antibody, a chimeric antibody, or a humanized antibody.

In another aspect, the disclosure provides compositions including an antibody or antigen-binding fragment of any of the antibodies described herein and a pharmaceutically acceptable carrier. These compositions can be used in the treatment of pathogenic infections.

The disclosure also provides kits including the compositions and antigens described herein.

In another aspect, the disclosure provides uses the antibody compositions described herein for treating, and methods of treating, a beta-lactamase-producing, gram negative bacterial infection in a subject, the use or method comprising: orally administering to a subject in need of treatment a therapeutically effective amount of the antibody or an antigen-binding fragment or a composition as described herein; and administering to the subject a therapeutically effective amount of at least one antibiotic for a time sufficient to treat the beta-lactamase-producing, gram negative bacterial infection in the subject.

In some embodiments, the method further includes identifying the subject as having a beta-lactamase-producing, gram negative bacterial infection, e.g., an extended spectrum beta lactamase (ESBL)-producing bacterial infection, e.g., from a bacterial cell selected from the group consisting of: *E. coli, Klebsiella peumoniac, Acinetobacter baumannii* and *Pseudomonas aeruginosa*.

In some embodiments, the beta-lactamase-producing, gram negative bacterial infection is an infection by a TEM-producing bacteria, e.g., an infection by a TEM-1-producing bacteria, e.g., TEM-1-producing *E. coli*.

In certain embodiments, the at least one antibiotic is selected from the group consisting of pencillin, benzylpenicillin, ampicillin, cefaloridine, ceftazidime, cefazolin, cefotaxime, cephalotin, aztreonam, colistin, fosfomycin, and temocillin. The antibody can be orally administered prior to the at least one antibiotic, or simultaneously.

In another aspect, the disclosure provides methods of inducing an immune response against beta-lactamnase in an avian host, the method comprising: administering to the avian host the antigen compositions described herein, wherein the antigen composition is administered in an amount sufficient to induce an immune response against the beta-lactamase in the avian host. The methods can further include recovering an egg from the avian host, and isolating IgY antibodies from the avian host egg.

The term "a" and "an" refers to one or more (i.e., at least one) of the grammatical object of the article. By way of example, "a cell" encompasses one or more cells.

As used herein, the terms "about" and "approximately," when used to modify an amount specified in a numeric value or range, indicate that the numeric value as well as reasonable deviations from the value known to the skilled person in the art, for example ±20%, ±10%, or ±5% are within the intended meaning of the recited value.

Unless otherwise specified, a "nucleotide sequence encoding a protein" includes all nucleotide sequences that are degenerate versions of each other and thus encode the same amino acid sequence.

The term "exogenous" refers to any material introduced from or originating from outside a cell, a tissue, or an organism that is not produced by or does not originate from the same cell, tissue, or organism in which it is being introduced.

The term "nucleic acid" refers to a deoxyribonucleic acid (DNA) or ribonucleic acid (RNA), or a combination thereof, in either a single- or double-stranded form. Unless specifically limited, the term encompasses nucleic acids containing known analogues of natural nucleotides that have similar binding properties as the reference nucleotides. Unless otherwise indicated, particular nucleic acid sequences also implicitly encompass complementary sequences as well as the sequence explicitly indicated. In some embodiments of any of the nucleic acids described herein, the nucleic acid is RNA. In some embodiments of any of the nucleic acids described herein, the nucleic acid is DNA.

Modifications can be introduced into a nucleotide sequence by standard techniques known in the art, such as polymerase chain reaction (PCR)-mediated mutagenesis and site-directed mutagenesis. Conservative amino acid substitutions are ones in which the amino acid residue is replaced with an amino acid residue having a similar side chain. Families of amino acid residues having similar side chains have been defined in the art. For example, families include amino acids with acidic side chains (e.g., aspartic acid and glutamic acid), basic side chains (e.g., arginine, lysine and histidine), uncharged polar side chains (e.g., asparagine, cysteine, glutamine, glycine, serine, threonine, tyrosine, and tryptophan), nonpolar side chains (e.g., alanine, isoleucine, leucine, methionine, phenylalanine, proline, and valine), beta-branched side chains (e.g., isoleucine, threonine and valine), and aromatic side chains (e.g., histidine, phenylalanine, tryptophan and tyrosine).

The terms percent "identity" and "identical" in the context of two or more amino acid sequences, refer to two or more sequences or subsequences that are the same or have a specific percentage of amino acid residues, e.g., at least 60%, at least 65%, at least 70%, at least 75%, at least 80%, at least 85%, at least 90%, or at least 95% or greater, that are identical over a specified region when compared and aligned for maximum correspondence over a comparison window or designated region, as measured using a sequence comparison algorithm, by visual inspection, or by manual alignment.

For sequence comparison of amino acid sequences, typically one amino acid sequence is referred to as a reference sequence to which one or more candidate sequences are compared. Various methods of sequence alignment are known to one skilled in the art, e.g., using publicly available software using known algorithms to achieve maximal alignment (e.g., BLAST program, ALIGN, ALIGN-2 (Genentech, South San Francisco, California), or Megalign (DNASTAR)), or using visual alignment. One of skill in the art can determine the parameters to achieve maximal alignment. For sequence comparison of amino acid sequences described in this application, the BLASTP algorithm standard protein BLAST for aligning two amino acid sequences with the default parameters was used.

Percentage of "sequence identity" is determined by comparing two optimally aligned sequences over a comparison window, where the amino acid sequence in the comparison window may include additions or deletions (e.g., gaps or overhangs) as compared to the reference sequence, which does not include additions or deletions for optimal alignment of the two sequences. For example, the percentage is calculated by determining the number of positions at which the identical amino acid residue occurs in both the query sequence and the reference sequence to yield the number of matched positions, dividing the number of matched positions by the total number of positions in the window of comparison and multiplying the result by 100 to yield the percentage of sequence identity. The output is the percent identity of the subject sequence with respect to the query sequence. In some examples, a query amino acid sequence that aligns with a reference sequence can result in many different lengths, with each length having its own percent identity.

The term "affinity" refers to the strength of the sum of all non-covalent interactions between an antigen-binding site and its antigen or epitope. Unless otherwise indicated, "affinity" refers to intrinsic binding affinity, which reflects a 1:1 interaction between an antigen or epitope and an antigen-binding domain. Affinity can be measured, e.g., using enzyme linked immunosorbent assay (ELISA) biolayer interferometry (e.g., FORTEBIO®), or surface plasmon resonance (SPR) technology (e.g., BIACORE®). Additional methods for determining the affinity of an antigen-binding domain and its antigen are known in the art.

The term "subject" is intended to include any mammal. In some embodiments, the subject is a mammal, e.g., a human or domesticated animal, such as a dog, cat, rodent (e.g., a mouse, rat, or hamster), a non-human primate, pig, goat, cow, horse, or sheep. Domesticated fowl (e.g., chickens, ducks, or geese) can also be treated. In some embodiments, the subject has or is at risk of developing an infection by beta-lactamase-producing bacteria. In some embodiments, the subject has previously been identified or diagnosed as having a bacterial infection (e.g., an infection by ESBL bacteria, e.g., an infection by a TEM-1-producing bacterium (e.g., a TEM-1-producing *E. coli*)).

The term "treat" or "treatment" as used herein refers to inhibiting, delaying the onset of, alleviating the effects of, or prolonging the life of a subject suffering from a bacterial infection. The phrase "therapeutically effective amount" refers to an amount or concentration of an antibody, a composition, or treatment described herein (e.g., an antibiotic) utilized for a period of time (including acute or chronic administration, and periodic or continuous administration) that is effective within the context of its administration for causing an intended effect or physiological outcome.

The term "inhibit" or "inhibition" as used herein refer to suppressing, or delaying the onset of a disease or condition related to a bacterial infection (e.g., an infection by TEM-1-producing bacteria (e.g., TEMI-1-producing *E. coli*)).

The term "antibody" is used herein in its broadest sense and includes certain types of immunoglobulin molecules that include one or more antigen-binding domains that specifically bind to an antigen or epitope. The term "antibody" includes, e.g., intact antibodies (e.g., intact immunoglobulins), antibody fragments, and antigen-binding domains or fragments thereof. One example of an antigen-binding domain is an antigen-binding domain formed by a VH-VL dimer. Additional examples of antibodies are described herein. Additional examples of an antibody are known in the art.

The term "neutralizing" as used herein in relation to the antibodies of the invention refers to antibodies that inhibit a pathogen from replication, in vitro or in vivo, regardless of the mechanism by which neutralization is achieved, or assay that is used to measure the neutralization assay.

The terms "antibody fragment" or antigen-binding fragment", as used herein is a portion of an antibody such as F(ab')$_2$, F(ab)$_2$, Fab', Fab, Fv, or scFv. Regardless of structure, an antibody fragment that binds to the same antigen that is recognized by the intact antibody. The term "antibody fragment" includes aptamers, and diabodies. The term "antibody fragment" also includes any synthetic or genetically engineered protein that acts like an antibody by binding to a specific antigen to form a complex.

The phrase "binds specifically" as used herein means a direct association between an antibody and its antigen, due to, e.g., covalent, electrostatic, hydrophobic, ionic interactions, and/or hydrogen bond interactions wherein the antibody binds to the antigen (e.g., a peptide or epitope within a target sequence, e.g., a TEM-1 protein) in preference to any other antigen.

The term "monoclonal antibody" refers to a population of antibody molecules that contain only one species of an antigen-binding site capable of immune-reacting with a particular epitope of a protein. For example, monoclonal IgY can be produced using phage display library screening. Briefly, the antibody library is screened to identify and isolate phages that express an antibody that binds to a beta-lactamase (e.g., TEM-1) and/or to a beta-lactamase-producing bacteria (e.g., a TEM-1-producing bacteria, e.g., a TEM-1-producing *E. coli*). Following screening, the display phage is isolated and the nucleic acid encoding the selected antibody can be recovered from the display phage and sub-cloned into other expression vectors by recombinant DNA techniques known in the art. The nucleic acid can be further manipulated (e.g., linked to nucleic acid encoding additional immunoglobulin domains, such as additional constant regions) and/or expressed in a host cell. As another example, monoclonal IgYs can be produced using well-known molecular cloning and cell fusion techniques. For example, peptide of TEM-1 (e.g., any of the peptides described herein, Peptides 1-25) is administered, e.g., via intraperitoneal injection to an avian subject (e.g., a chicken) to induce an immune response (e.g., a humoral immune response). Immune cells are isolated from the thymus, bursa fabricius, bone marrow, spleen, or lymphoid nodules and fused with myeloma cells as previously described (see, e.g., Kohler and Milstein, *Nature* 1975, 256:495-497). The resulting hybrid cells are then subcloned using limited dilution to isolate individual hybrid cells producing the desired monoclonal IgYs.

The term "humanized antibody" refers to an antibody that has been engineered to comprise one or more human framework regions in the variable region together with non-human (e.g., chicken or mouse) complementarity-determining regions (CDRs) of the heavy and/or light chain. In some embodiments, a humanized antibody comprises sequences that are entirely human except for the CDR regions. Humanized antibodies are typically less immunogenic to humans, relative to non-humanized antibodies, and thus offer therapeutic benefits in certain situations.

As used herein, "full human antibodies" are antibodies or antigen-binding fragments of antibodies that contain only human-derived amino acid sequences. For example, a fully human antibody can be produced from a human B-cell or a human hybridoma cell.

The term "chimeric antibody" refers to an antibody that has been engineered to comprise at least one human constant region. For example, one or all (e.g., one, two or three) of the variable regions of the light chain(s) and/or one or all (e.g., one, two or three) of the variable regions of the heavy chain(s) of an avian antibody (e.g., a monoclonal IgY) can each be joined to a human constant region, such as, e.g., to an IgG1 human constant region.

A $V_HH$ domain is a single monomeric variable antibody domain that can be found in camelids. A $V_{NAR}$ domain is a single monomeric variable domain that can be found in cartilaginous fish. Non-limiting examples of $V_HH$ domains and $V_{NAR}$ domains are described in, e.g., Kijanka et al., *Nanomedicine* 10:161-1674, 2015; Kovaleva et al., *Expert. Opin. Biol. Ther.* 14:1527-1539, 2014; Vincke et al., *Methods Mol. Biol.* 911:15-26, 2012 and Wesolowski et al., *Med. Microbiol. Immunol.* 198:157-174, 2009.

A "Fv" fragment includes a non-covalently-linked dimer of one heavy chain variable domain and one light chain variable domain.

A "Fab" fragment includes the constant domain of the light chain and the first constant domain (Cm) of the heavy chain, in addition to the heavy and light chain variable domains of the Fv fragment.

A "F(ab')2" fragment includes two Fab fragments joined near the hinge region by disulfide bonds.

As used herein, the term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in the complementarity determining regions (CDRs) to interact with the antigen.

The phrase "cytotoxic to a bacterial cell" refers to the inducement, indirectly or directly, in bacterial cell death (e.g., necrosis or apoptosis).

The phrase "cytostatic to a bacterial cell" refers to an agent that causes a direct or indirect decrease in proliferation (e.g., bacterial cell division) in vivo or in vitro. When an agent is cytostatic to a bacterial cell, the agent can, e.g., directly or indirectly result in bacterial cell cycle arrest. In some embodiments, an agent that is cytostatic to a bacterial cell can reduce the number of bacterial cells in a population of bacterial cells that are in S phase (as compared to the number of bacterial cells in a population of the bacterial cells that are in S phase prior to contact with the agent). In some examples, an agent that is cytostatic to a bacterial cell can reduce the percentage of bacterial cells in S phase by at least 20%, at least 40%, at least 60%, or at least 80% (e.g., as compared to the percentage of bacterial cells that are in S phase prior to contact with the agent).

The term "population" when used before a noun means two or more of the specific noun. For example, a "population of bacterial cells" means "two or more bacterial cells." Non-limiting examples of bacterial cells are described herein.

Unless otherwise defined, all technical and scientific terms used herein have the same meaning as commonly understood by one of ordinary skill in the art to which this invention belongs. Methods and materials are described herein for use in the present inventions; other suitable methods and materials known in the art can also be used. The materials, methods, and examples are illustrative only and not intended to be limiting. All publications, patent applications, patents, sequence, database entries, and other references mentioned herein are incorporated by reference in their entirety. In case of conflict, the present specification, including definitions will control.

Other features and advantages of the invention will be apparent from the following detailed description and figures, and from the claims.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
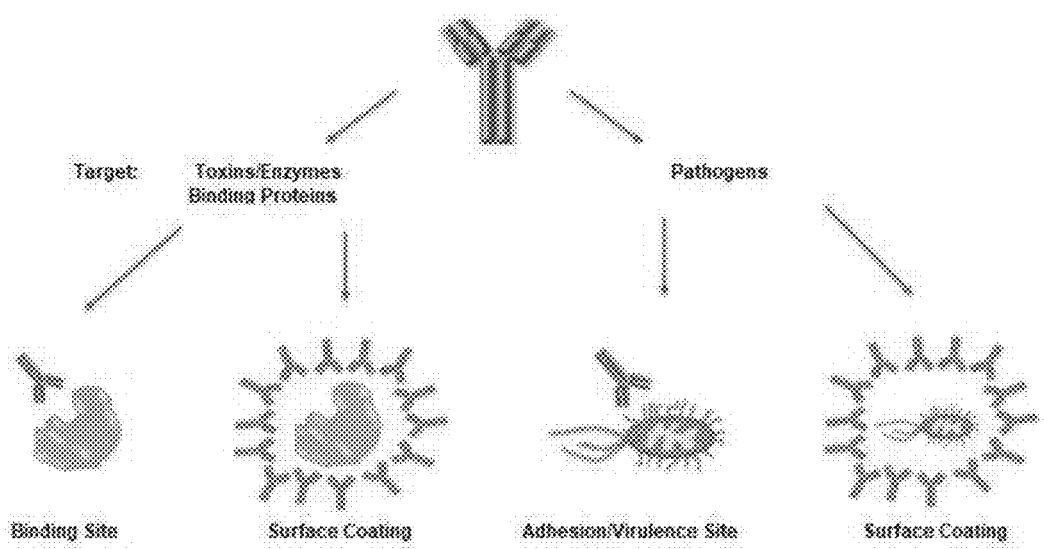
FIG. 1 is a schematic representation of exemplary antibody targeting beta-lactamase approaches.

This disclosure presents antibodies directed against different targets that can be used to treat infections by beta-lactamnase-producing bacteria, e.g., TEM-1 beta lactamase-producing bacteria, such as *E. coli*. This disclosure also provides model systems to develop such specific antibodies against these therapeutic targets. In general, different types of antibodies can be generated against the entire beta-lactamase, or against the active site omega loop of beta-lactamase, and this disclosure provides numerous examples of specific peptides that correspond to this active site that produce highly effective antibodies. Alternatively, antibodies can be directed against beta-lactamase-producing bacteria, such as *E. coli*, that are inactivated, e.g., by heat or an electron beam. Either way, these targets produce highly specific antibodies that can inhibit the growth of ß-lactamase-producing bacteria, such as L col.

Two strategies are used to target the beta-lactamase-producing *E. coli* with antibodies such as IgYs. First, as a complement to antibiotics, antibodies are generated against the enzyme beta lactamase, e.g., TEM1 beta lactamase, to be used in combination with an antibiotic, e.g., an antibiotic that is typically inhibited by beta lactamase, e.g., ampicillin. Second, as an alternative to antibiotics, antibodies, e.g., IgYs, are generated against beta lactamase-producing bacteria, e.g., TEM1 beta lactamase-producing bacteria, such as *E. coli*, without the need to use an antibiotic (of course, an antibiotic can also be used with these IgY antibodies).

In the first strategy, antibodies are developed against either the whole beta lactamase, e.g., TEM-1 (TIgY and aTIgY), or only the active site omega loop of beta lacatamase, e.g., TEM-1 (pIgY, p2IgY, ap1IgY and ap2IgY). When this strategy is used to develop IgY antibodies, fowl, such as chickens, are immunized with beta-lactamase, e.g., TEM-1, or in silico designed short peptides that mimic the active site. As described in the Examples below, among seven identified catalytic and conservative residues for TEM-group ß-lactamases, 2 pairs of residues were chosen as a base for two 11-amino-acid peptides synthesized to mimic the active site of TEM-1: Ser70 and Lys73 (Peptide 1: RFPMMSTFKVL (SEQ ID NO: 1), located on a 1H2 helix), and Glu166 and Asn170 (Peptide 2: TRLDRWEPELN (SEQ ID NO: 2), located on the Q-loop).

In the second strategy, antibodies, such as IgYs, are developed against beta lactamase-producing bacteria, e.g., TEM-1-producing bacteria, such as *E. coli*. In this case, poultry, such as chickens, are immunized with whole bacterial, e.g., *E. coli*, cells that are inactivated by one of two methods: e-beam and heat treatment.

Antibodies Against Beta-Lactamase or Pathogenic Bacteria
Antibodies Against Beta-Lactamase Antibodies can be generated against the entire beta-lactamase enzyme or preferably against the active site omega loop. An example of beta-lactamase is TEM-1, which is a plasmid encoded, 29 kDa atomic mass enzyme, representing the predominant group of TEM type beta-lactamases providing antibiotic resistance within the Enterobacteriaceae family. Its hydrolytic profile indicates activity against penicillins, first generation cephalosporins—cephaloridine, cefazolin, second generation cephalosporins—cephalotin, but not against the third generation of cephalosporins (cefotaxime, ceftazidime) and mnonobactam aztreonam, and it is inhibited by clavulanic acid (CLA) and tazobactam (TZB) (Bush et al., *Annu. Rev. Microbiol.* 2011, 65:455-478; and Bouthors et al., *Biochein. J* 1998, 330:1443-1449).

TEM-1 is a member of the class A beta-lactamases, which includes a broad spectrum of beta-lactamases that hydrolyze penicillins and cephalosporins (Naas et al., *J. Enzyme Inhib. Med. Chem.* 2017, 32:917-919). TEM and SHV subtypes are the most prevalent class A beta-lactamases. In fact, TEM-1 and SHV-1 share 68% sequence identity. CTX-M is another class A subtype that is clinically important as a source of ESBL mutants (Brandt et al., tends *Microbiol.* 1994, 2:357-360; Bush et al., *Annu. Rev. Microbiol.* 2011, 65:455-478; and Meneksedag et al., *Comput. Rio. Chem.* 2013, 43, 1-10). In general, known beta-lactamases are found in Naas, T. et al., Beta-Lactamase DataBase (BLDB)—Structure and Function, *J. Enzyme Inhib. Med. Chem.* 2017, 32, 917-919 and the database is available online.

As a member of class A enzymes, TEM-1 has two domains α and α/β, with the active site placed between them. Two of the most important and conserved catalytic residues Lys73 and Ser70 are located on helix H2. Together with Glu166 and catalytic water molecule participate in an acylation step in reaction of the ß-lactam hydrolysis (Meroub et al., *J. Am. Chem. Soc.* 2005, 127:15397-15407; and Golemi-Kotra et al., *J. Biol. Chem.* 2004, 279:34665-34673).

Figure 2:
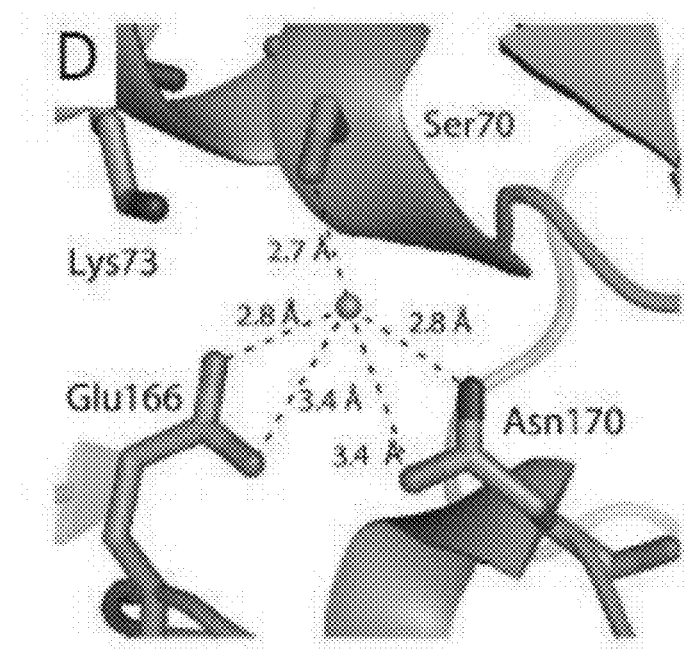
FIG. 2 is a schematic representation of the conserved amino acids within the TEM-1 active site.

Other important non-mutable residues are situated in a Q-loop: Glu166 and Assn170. Asn170 helps in positioning the catalytic water molecule by forming the hydrogen bond through the side chain of the residue. Then, it enables the Glu166 to activate the water molecule in the deacylation step (Jelsch et al., *Proteins* 1993, 16:364-383; Strynadka et al., *Nature* 1992, 359:700-705; Minasov et al., *J. Am. Chem. Soc.* 2002, 124:5333-5340; Stojanoski et al., *J Biol. Chem.* 2015, 290:10382-10394; Adachi et al., *J. Biol. Chem.* 1991, 266:3186-3191; and Leung et al., *Biochem. J.* 1994, 299:671-678). A visualization of ß-lactamase TEM-1 can be found in FIG. 2.

Figure 3:
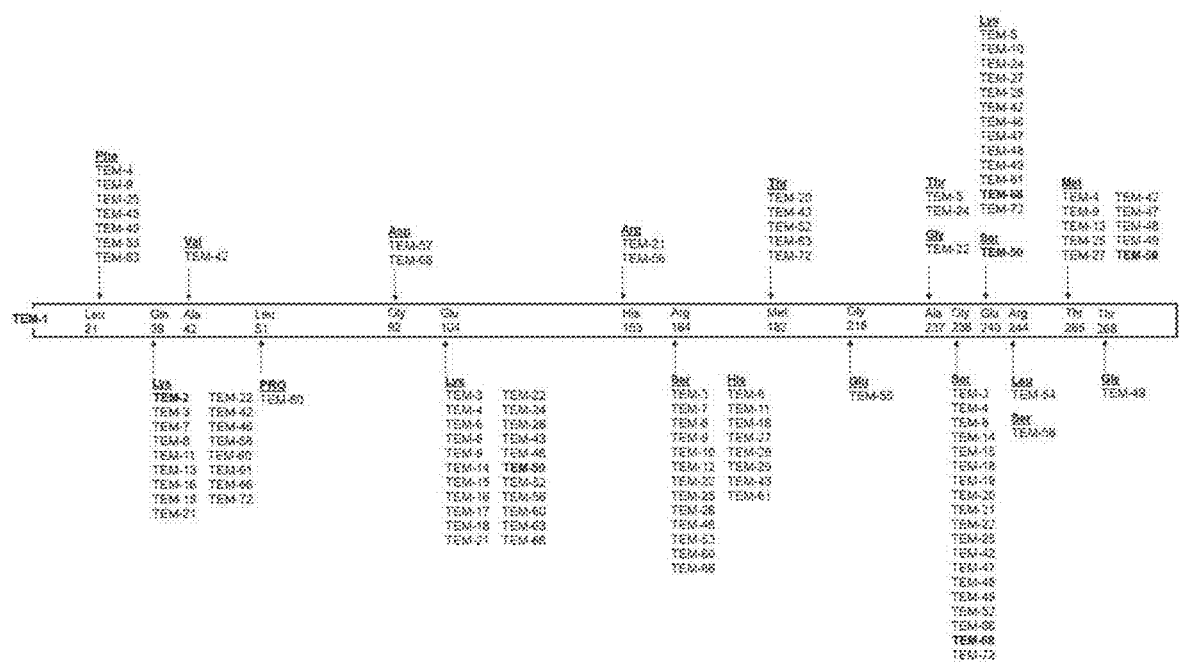
FIG. 3 is a schematic representation of amino acid substitutions found in related TEM beta-lactamases as compared to a TEM-1 amino acid sequence.

The f-loop forms a rim over the active pocket of TEM-1 and it has a huge impact on the structure and function of the enzyme. It is directly involved in substrate interaction, water coordination necessary for catalysis, and is mutation-sensitive (Strynadka et al., *Nature* 1992, 359:700-705Salverda et al., *FEMS Microbiol. Rev.* 2010, 34:1015-1036; and Petrosino et al., *J. Bacteriol.* 1996, 178:1821-1828). Beta-lactamases are highly mutable enzymes, and single substitutions of amino acids can change their interaction with a substrate leading to the development of new mutants with an enlarged antibiotic hydrolysis profile—so called Extended Spectrum Beta Lactamases (ESBLs). Apart from possessing a standard beta-lactamase functionality, they are able to hydrolyze the third generation of cephalosporins and aztreonam. TEM-type derivatives have been developed as a consequence of mutations in blaTEM-1 gene resulting in amino acids substitutions, which mainly occur within or near the active site, alone or combined and mostly appear as follow: Glu104→Lys, Arg164→Ser/His, Gly238→Ser, Glu240→Lys (Jacoby et al., *Antimicrob. Agents Chemother.* 1991, 35:1697-1704; and Bradford et al., *Clin. Microbiol. Rev.* 2001, 14:933-951). Some examples of TEM-1 mutants with ESBL profile are shown in FIG. 3.

These amino acids mutations can change the flexibility of the Q-loop, the size of a space around the active pocket where the substrate is bound, or stabilize the conformation of the enzyme (Bouthors et al., *Biochem. J.* 1998, 330:1443-1449; and Stojanoski et al., *J. Biol Chem.* 2015, 290:10382-10394). These changes enable ESBLs to hydrolyze new generations of antibiotics. As an example of a TEM-1 mutant can be a clinically found ESBL TEM-52, which is able to hydrolyze additionally the third generation cephalosporin (cefotaxime). Even though mutations did not cover the active site residues of the enzyme, the set of important functional substitutions E104K/G238S/M182T changed the conformation of the loops near the active site (Fart et al., *Nat. Commun.* 2016, 7:12965). It resulted in a change of pI value for TEM-52 and its kinetic parameters in the interaction with penicillins, first- and third-generation of cephalosporins. TEM-52 shows smaller values of Km in reaction with penicillins and I-generation of cephalosporins (benzylpenicillin: KM TEM-52 of 5.3 µM TEM-52 vs. KM TEM-1 of 26 µM; ampicillin: KM TEM-52 4.1 µM vs. KM TEM-1 40 µM; I-generation cephalosporin (cefaloridine): KM TEM-52 13 µM vs. KM TEM-1 244 µM), this means the affinity between substrate and enzyme is stronger than with TEM-1, and as a result the efficiency of antibiotic hydrolysis is higher. Moreover TEM-52 as an ESBL hydrolyses III-gen cephalosporins (KM of 30 µM), while the Km of TEM-1 ß-lactamase in reaction with this group of antibiotics could not be determined (Poyart et al., *Antimicrob. Agents Chemother.* 1998, 42:108-113).

This mechanism shows how efficiently ß-lactamases can provide resistance to newly introduced antibiotics through fast genetic evolution. The outbreak of ESBLs can be explained by selective pressure coming from the mass scale introduction of aminopenicillins, III-generation of cephalosporin and aztreonam (Bush et al., *Annu. Rev. Microbiol.* 2011, 65:455-478; and Medeiros, *Clin. Microbiol. Infect.* 2000, 6:27-33). On the other hand, it can be supported by naturally occurred mutants, which exchange resistance encoded genes with clinical strains. Due to the fact that penicillins and cephalosporins have their origin in microbiological organisms, resistance against them could have been developed by bacteria in parallel. Nowadays more than 200 TEM type variants were identified and 86 of them have ESBL phenotype (Bush et al., *Antimicrob. Agents Chemother.* 2010, 54:969-976; Salverda et al., *EMS Microbiol. Rev.* 2010, 34:1015-1036; and Pimenta et al., *Mini Rev. Med Chem.* 2014, 14:111-122).

The structure of TEM-1, the firstly discovered beta lactamase, is well studied and described (Datta et al., *Nature* 1965, 208:239-241; and Lahey Clinic). It is also classified as a parental enzyme for a TEM group of ß-lactamases of more than 200 members, of which more than 86 were characterized as ESBLs (Bush et al., *Antimicrob. Agents Chemother.* 2010, 54:969-976; Salverda et al., *FEMS Microbiol. Rev.* 2010, 34:1015-1036; and Pimenta et al., *Mini Rev. Med. Chem.* 2014, 14:111-122).

Antibodies Against Beta-Lactamase-Producing Bacteria

The choice of an whole bacteria as an antigen depends on the characteristics of the pathogen and therapy strategy. Antibodies can be generated against colonization factors (outer membrane proteins, fimbriae/pili and lipopolysaccharides), flagella, mucosal receptors, enzymes, and toxins important for bacterial survival (Malekshahi et al., *Microb. Pathog.* 2011, 51:366-372; and Jin et al., *FFMS Immunol. Med. Microbiol.* 1998, 21:313-321).

Several strategies for using antibodies in host protection can be distinguished: 1) agglutination of bacteria, 2) inhibition of bacterial adhesion, 3) suppression of virulence factors, 4) toxin neutralization and 5) enzyme inactivation (Xu et al., *Biotechnol. Adv.* 29:860-868) (FIG. 1). The process of fowl, e.g., chicken immunization can be influenced by the following factors: antigenicity of the immunogen, type of adjuvant, route of antigen delivery, frequency of administration, avian properties (breed, age, egg lying capacity) (Schade et al., *Altern. Lab. Anim.* 2005, 33:129-154).

IgY technology is an effective way to provide immunity against a wide range of pathogens, which can reduce or possibly replace the use of antibiotics in clinics and industry, and provide successful prevention, treatment, or growth enhancement overtaking the problem of increasing antibiotic resistance. An increased number of reported IgYs against a wide range of bacteria can be observed.

IgYs can be used as well in farm animals for prevention and as an alternative treatment in the form of a food additive against common bacterial livestock diseases.

IgY Antibodies

IgY antibodies are polyclonal immunoglobulins produced by avian species against pathogens to provide an immune response in newly hatched eggs, e.g., chicken eggs, in which humoral immunity is still not developed. IgYs are mostly present in serum and egg yolk, which provides nutrition to embryos. IgYs are also the dominant class of immunoglobulin in fowl eggs (e.g., chicken eggs, duck eggs, pheasant eggs, quail eggs, goose eggs, turkey eggs) (see, e.g., Leslie et al., *J. Exp. Med* 1969, 6:1337-1352; and Schade et al., *Altern. Lab. Anim.* 2005, 33:129-153). Like other vertebrates, the avian immune system can be divided into an innate immune system and an adaptive immune system. The adaptive immune system is highly specific to pathogens and can be further divided into cellular and non-cellular responses. Both types of responses are carried by B lymphocytes and T lymphocytes, respectively. In the cellular response, T cells control the activity of macrophages, T-helper cells and B-cells that recognize the antigen as a foreign, pathogenic antigen. In the non-cellular response, also called humoral response, B-cells produce antibodies, which circulate in blood and plasma, and can protect host organisms (e.g., avian subjects (e.g., chickens, ducks, pheasants, quails, geese, or turkeys) from pathogens by: agglutination, activating opsonization, activating cell-mediated cytotoxity, or neutralization.

IgY technology is the production of specific polyclonal antibodies in birds (e.g., chickens, ducks, turkeys, geese, quails, or pheasants), and takes advantage of the natural maternal passive immunity protection to each of its offspring. As compared to other antibody development strategies, this approach is relatively cheap, effective, simple, and more ethical than antibody development strategies that use mammalian systems, such as rabbits, mice, rats, or horses. It is officially recognized as the alternative method for antibody production supporting animal welfare (Schade et al., *ATLA* 1996, 925-934). IgYs are widely used in commercial and research applications, including the fields of diagnostic and proteomics (Spillner et al., *Biologicals* 2012, 40:313-322).

There are many advantages to using avian IgY antibodies over other existing antibody technologies: 1) IgYs are easily purified (only one class of IgY antibodies are in the egg yolk and are present at high concentrations (e.g., about 100 mg to about 150 mg/egg), 2) IgYs are polyclonal antibodies, so its antigen specificity will not be dampened but antigenic variations of epitopes, 3) IgYs can be produced against conserved mammalian proteins, 4) IgYs do not recognize mammalian epitopes, 5) IgYs are produced using methods that are not harmful to animals (e.g., collecting eggs instead of drawing and collecting blood), 6) IgYs can be used in passive immunization (Müller et al., *Nutr. J.* 2015, 14: 109; Kovacs-Nolan et al., *Annu. Rev. Food Sci. Technol.* 2012, 3:163-182; Rahman et al., *Hum. Vaccin. Immunother.* 2013, 9:1039-1048; and Mine et al., *J. Med. Food* 2002, 5:159-169).

IgYs are accumulated in egg yolk in high concentrations—1 mL contains up to 25 mg of IgYs. IgYs also show high stability at temperatures ranging about 30° C. to about 70° C., and at a pH range of about 3.5 to about 11 (Rahman et al., *Hum. Vaccin. Immunother.* 2013, 9:1039-1048).

Poultry, such as chickens, ducks, or geese are immunized with the antigen of interest in the dose between 10 μg and 1 mg, starting usually with the initial immunization followed by three booster doses in time intervals to obtain higher antibody titers. There are different methods of an antigen introduction: subcutaneous, intramuscular, intravenous or oral. Intravenous rout can cause anaphylactic reaction, has to be introduced very slowly and should be used without adjuvants. Among all the methods, the highest antibody titers are achieved by intramuscular injections (Chang et al., *J. Agric. Food Chem.* 1999, 47:61-66; Gutierrez Calzado et al., *ATLA* 2001, 29:717-726; and Hedlund et al., *In Vivo (Brooklyn)* 2001, 15:381-384). First specific IgYs can be already found in serum after 6-7 days (Bollen et al., *In Vivo (Brooklyn)* 1997, 11:395-398).

An optimal dose of antigen depends on its size and type and has to be experimentally tested. For example, it is advised to use carriers or adjuvants, e.g., bovine serum albumin (BSA), keyhole limpet hemocyanin (KLH), *Concholepas concholepas* hemocyanin (CCH), or ovalbumin (OVA) to couple small antigens like short peptides below 10 kDa, to enhance the immune response. In some embodiments, an adjuvant is included. Non-limiting examples of adjuvants include: Freund's complete adjuvant (FCA), Freund's incomplete adjuvant (FIA), specol, and lipopeptide Pam3Cys-Ser-(Lys)4 (PCSL). When immunization is done with an antigen bigger than 50 kDa, obtaining 2-10% specific activity of IgYs can be expected. Unfortunately, a drop down of specificity to less than 1% can be observed, when antigen has lower molecular weight (Schade et al., *Altern. Lab. Anim.* 2005, 33:129-154).

Additionally to antigen, modulators stimulating B-cells can be used, which improve the immune response in chickens, e.g., Freund's complete adjuvant—mycobacterial antigens emulsified in mineral oil (FCA), Freund's incomplete adjuvant—water and oil emulsion (FIA), specol—water with purified mineral oil, keyhole limpet hemocyanin (KLH), or lipopeptide Pam3Cys-Ser-(Lys)4 (PCSL). FCA is the most popular and most effective one (Schade et al., *Altern. Lab. Anim.* 2005, 33:129-154; Erhard et al., *Poult. Sci.* 2000, 79:1264-1270; and Sun et al., *Vet. Immunol. Immunopathol.* 2008, 121:107-112).

One hen is able to produce up to 150 mg IgYs per egg. When this number is combined with average number of eggs hen can lay per year—325, it can give a result of 40 g of IgYs per year. As compared to with mammals—200 mg of IgGs per bleed giving 1.4 g of antibodies per year (Mine et al., *J. Med. Food* 2002, 5:159-169; Cook et al., *Poult. Sci. J.* 2010, 66:215-226; Schade et al., *ATLA* 1999, 403-419; and Tini et al., *Comp. Biochem. Physiol. A. Mol. Integr. Physiol.* 2002, 131:569-574).

There are different methods of IgY purification depends on scale, costs, effectiveness and technology. In some embodiments of any of the IgYs described herein, the IgY is purified by precipitation (e.g., ammonium sulfate precipitation, polyethylene glycol precipitation, salt, dextran precipitation, sodium precipitation, xanthan precipitation, ethanol precipitation), by affinity chromatography (e.g., ligand-affinity chromatography, ion exchange chromatography (anionic or cation)), or ultrafiltration, or any combination thereof. In some embodiments of any of the IgYs described herein, the IgY is purified by precipitation (e.g., any of the precipitation methods described herein), followed by affinity chromatography (e.g., any of the affinity chromatography methods described herein).

Immunoglobulin Y (IgY) Against Beta Lactamase Polypeptides

Provided herein are IgYs directed against beta-lactamase peptides (e.g., TEM-1 beta-lactamase proteins) and the beta-lactamase active site omega loop (e.g., a TEM active site, a TEM-1 active site). In some embodiments of any of the IgYs described herein, the IgY against beta-lactamase specifically binds to a sequence that is at least 80% (e.g., at least 82%, at least 84%, at least 85%, at least 86%, at least 88%, at least 90%, at least 92%, at least 94%, at least 95%, at least 96%, at least 97%, at least 98%, or at least 99%) identical to a contiguous sequence of any of the peptides disclosed herein, including:

```
                                      (SEQ ID NO: 1)
RFPMMSTFKVL (SEQ ID NO: 2)
TRLDRWEPELN (SEQ ID NO: 3)
FPMMSTFKVL (SEQ ID NO: 4)
TRLDRWEPELN (SEQ ID NO: 5)
TRLDSWEPELN (SEQ ID NO: 6)
TRLDHWEPELN (SEQ ID NO: 7)
RLDRWEPDLN (SEQ ID NO: 8)
TRLDRWETELN (SEQ ID NO: 9)
TRLDRYEPELN (SEQ ID NO: 10)
TRLDRIEPDLN (SEQ ID NO: 11)
SRLDRWETELN (SEQ ID NO: 12)
RFPMMSTFKVM
```

RFPMMSTFKVI (SEQ ID NO: 13)

RFPMMSTFKVV (SEQ ID NO: 14)

RFPLMSTFKVL (SEQ ID NO: 15)

RFPMMSTFKTL (SEQ ID NO: 16)

RFPMLSTFKVL (SEQ ID NO: 17)

RFPMISTFKVL (SEQ ID NO: 18)

RFPMVSTFKVL (SEQ ID NO: 19)

RFPIMSTFKVL (SEQ ID NO: 20)

RFPMMNTFKVV (SEQ ID NO: 21)

RFPMLSTFKVV (SEQ ID NO: 22)

RFPMCSTFKVL (SEQ ID NO: 23)

RFPLMSTFKTL (SEQ ID NO: 24)

RFPLMSTFKAL (SEQ ID NO: 25)

RFPMVSTFKVV (SEQ ID NO: 26)

FPMMSTFKVV (SEQ ID NO: 27)

RFPVVSTFKVL (SEQ ID NO: 28)

RFPMCSTFKLL (SEQ ID NO: 29)

RFPMASTFKAL (SEQ ID NO: 30)

RFPMCSTFKTL (SEQ ID NO: 31)

RFPLCSTFKVM (SEQ ID NO: 32)

IADKSGAGERG (SEQ ID NO: 33)

IADKTGAGERG (SEQ ID NO: 34)

IADKSGTGERG (SEQ ID NO: 35)

IADKSGAGKRG (SEQ ID NO: 36)

IADKSGASERG (SEQ ID NO: 37)

IADKSGAGRRG (SEQ ID NO: 38)

IADKSGANERG (SEQ ID NO: 39)

IADKAGAGERG (SEQ ID NO: 40)

IADKSGADERG (SEQ ID NO: 41)

IADRTGAGERG (SEQ ID NO: 42)

IADKSGAGVRG (SEQ ID NO: 43)

IADKSGTGKRG (SEQ ID NO: 44)

IADKTGAGARG (SEQ ID NO: 45)

IADKTGAGKRG (SEQ ID NO: 46)

TRLGRWEPELN (SEQ ID NO: 47)

RLDRWEVELN (SEQ ID NO: 48)

RLDRWELELN (SEQ ID NO: 49)

TRLDRIEPDLN (SEQ ID NO: 50)

$X_1$RLD$X_2$$X_3$E$X_4$$X_5$LN, (SEQ ID NO: 51)

in which $X_1$ is T or S or omitted, $X_2$ is R, S, or H, $X_3$ is W, Y, or I, $X_4$ is P or T, and $X_1$ is E or D.

One skilled in the art can appreciate that mutation of an amino acid that is not conserved between different species is less likely to negatively alter the activity of a protein (e.g., a TEM protein), mutation of an amino acid that is conserved between species is more likely to negatively alter the activity of a protein (e.g., a TEM protein). Methods of introducing one or more amino acid substitutions into a wildtype protein are known in the art.

TEM activity can be determined using a number of different assays, e.g., through the use of enzyme-linked immunosorbent assay (ELISA), a colorimetric assay (e.g., nitrocefin assay), or inhibition assay. Additional assays of determining TEM activity are known in the art.

Exemplary TEM peptides targeting the TEM active site can include a sequence that is at least 80% (e.g., at least 82%, at least 84%, at least 85%, at least 86%, at least 88%, at least 90%, at least 92%, at least 94%, at least 95%, at least 96%, at least 97%, at least 98%, or at least 99%) to SEQ ID NO: 1 or 2.

In some embodiments, the TEM peptide targeting the TEM active site can include a consensus sequence ((T/S)RLD(R/S/H)-(W/Y/I)-E(P/T)-(E/D)-LN: SEQ ID NO: 19), in which the first amino acid T is optional. Exemplary TEM peptides targeting the TEM active site are SEQ ID Nos. 20, 21, 22, 23, 24, 25, and 26.

To develop IgYs against TEM-1 active site, also with the perspective of targeting and inactivating TEM-1 mutants, the structure analysis was focused on the identification of low mutable amino acids residues playing important role in antibiotic hydrolysis process. Due to these requirements, Peptide 1 (SEQ ID NO: 1) and Peptide 2 (SEQ ID NO: 2), containing the critical amino acids for TEM-1 activity, were chosen as a base for the p1IgY and p2IgY/ap2IgY development.

In some embodiments of any of the IgYs described herein, the IgY is purified by precipitation (e.g., ammonium sulfate precipitation, polyethylene glycol precipitation, salt, dextran precipitation, sodium precipitation, xanthan precipitation, ethanol precipitation), by affinity chromatography (e.g., ligand-affinity chromatography, ion exchange chromatography (anionic or cation)), or by ultrafiltration. In some embodiments of any of the IgYs described herein, the IgY is purified by precipitation (e.g., any of the precipitation methods described herein), followed by affinity chromatography (e.g., any of the affinity chromatography methods described herein).

Immunoglobulin Y (IgY) Against Beta Lactamase-Producing Bacteria

Provided herein are IgYs against inactivated (e.g., e-beam-inactivated or heat-inactivated) beta-lactamase-producing bacteria (e.g., a TEM-1 beta-lactamase-producing bacteria (e.g., a TEM-1 beta-lactamase-producing *E. coli*).

In some embodiments of any of the IgYs against beta-lactamase-producing bacteria, the beta-lactamase-producing bacteria is an extended spectrum beta lactamase (ESBL)-producing bacteria. In some embodiments, the ESBL-producing bacterial is a bacterial cell selected from the group consisting of: an *E. coli* cell, a *Klebsiella pneumonia* cell, an *Acinetobacter baumannii* cell and a *Pseudomonas aeruginosa* cell.

In some embodiments of any of the IgYs against beta-lactamase-producing bacteria, the beta-lactamase-producing bacteria is a TEM, e.g., a TEM-1, beta-lactamase-producing bacteria. In some embodiments, the TEM beta-lactamase-producing bacteria is a TEM-1 beta-lactamase-producing *E. coli* cell, a TEM-1 beta-lactamase-producing *Klebsiella peumoniae* cell, a TEM-1 beta-lactamase-producing *Acinetobacter baumannii* cell or a TEM-1 beta-lactamase-producing *Pseudomonas aeruginosa* cell.

In some embodiments of any of the IgYs against beta-lactamase-producing bacteria, the beta-lactamase-producing bacteria is inactivated by heat at temperature of about 50° C. to about 80° C. (e.g., about 50° C. to about 75° C., about 50° C. to about 70° C., about 50° C. to about 65° C., about 50° C. to about 60° C., about 60° C. to about 80° C., about 60° C. to about 70° C., about 70° C. to about 80° C., about 50° C., about 55° C., about 60° C., about 65° C., about 70° C., about 75° C., or about 80° C.).

In some embodiments of any of the IgYs against beta-lactamase-producing bacteria, the beta-lactamase-producing bacteria is inactivated by low energy electron irradiation. In some embodiments, the beta-lactamase-producing bacteria is inactivated by low energy electron irradiation at a range of about 1 to about 10 kGy (e.g., at about 1 to about 8 kGy, about 1 to about 6 kGy, about 1 to about 5 kGy, about 1 to about 4 kGy, about 1 to about 2 kGy, about 1 kGy, about 2 kGy, about 3 kGy, about 4 kGy, about 5 kGy, about 6 kGy, about 7 kGy, about 8 kGy, about 9 kGy, or about 10 kGy).

In some embodiments of any of the IgYs described herein, the IgY is purified by precipitation (e.g., ammonium sulfate precipitation, polyethylene glycol precipitation, salt, dextran precipitation, sodium precipitation, xanthan precipitation, ethanol precipitation), by affinity chromatography (e.g., ligand-affinity chromatography, ion exchange chromatography (anionic or cation)), or by ultrafiltration. In some embodiments of any of the IgYs described herein, the IgY is purified by precipitation (e.g., any of the precipitation methods described herein), followed by affinity chromatography (e.g., any of the affinity chromatography methods described herein).

Additional Aspects of IgYs Against Beta Lactamase-Producing Bacteria and TEM-1 Beta Lactamase Polypeptides Any of the IgYs against beta-lactamase-producing bacteria or any of the IgYs against TEM-1 beta-lactamase described herein can be a monoclonal antibody, or a polyclonal antibody, or an antigen-binding fragment thereof. See, e.g., Morin et al., *Antimicrob. Agents Chemother.* 1987, 1761-1767 for examples of monoclonal TEM-1 antibodies.

In some embodiments of any of the IgYs described herein, the IgY is a monoclonal antibody or an antigen-binding fragment thereof. In some embodiments of any of the IgYs described herein, the IgY is a polyclonal antibody or an antigen-binding fragment thereof. In some embodiments of any of the IgYs described herein, the IgY against beta-lactamase is a humanized antibody, or an antigen-binding fragment thereof. In some embodiments of any of the IgYs described herein, the IgY is a chimeric antibody, or an antigen-binding fragment thereof. In some embodiments, the IgY can be a humanized antibody, a chimeric antibody, or a multivalent antibody.

In some embodiments, the antigen-binding fragment can be a Fab fragment, a Fab' fragment, a F(ab')2 fragment, a Fv fragment, a scFv fragment, a sc(Fv)$_2$ diabody, a scFv-Fc, a $V_H$H domain, a $V_{NAR}$ domain or a combination thereof. Such fragments can be produced from the antibody using techniques well established in the art (see, e.g., Rousseaux et al., in Methods Enzymol., 121:663-669 Academic Press, (1986)). For example the (F(ab')2 fragments can be produced by reducing the disulfide bridges of the F(ab')2 fragments.

The term "diabody" refers to a bivalent antibody fragment construct by gene fusion (see, e.g., Holliger et al., *Proc. Natl. Accad. Sci. U.S.A.* 1993, 90:6444-6448. Diabodies are dimers composed of two polypeptide chains. In each of the polypeptide chains forming a dimer, a $V_L$ and a $V_H$ are generally linked by a linker in the same chain. In some examples, a linker in a diabody is short enough such that the $V_L$ and $V_H$ cannot bind to each other. Specifically, the number of amino acid residues constituting the linker is, for example, about 5 amino acid residues. Therefore, the $V_L$ and $V_H$ encoded on the same polypeptide cannot form a single-chain variable region fragment and will form a dimer with another single-chain variable region fragment. As a result, the diabody has two antigen-binding sites.

ScFv antibodies are single-chain polypeptides producing by linking $V_H$ and $V_L$ via a linker or such (e.g., Huston et al., *Proc. Natl. Acad. Sci. U.S.A.* 85:5879-5883, 1988. The H-chain V region and L-chain V region of scFv may be derived from any antibody described herein. The peptide linker for linking the V regions is not particularly limited. In some examples, an single chain peptide containing about 3 to about 5 amino acid residues can be used as a linker.

Additional types of antibody fragments include, for example, monospecific or multispecific antibody fragments, such as bispecific, trispecific, and multispecific (e.g., diabodies, triabodies, or tetrabodies), minibodies, chelating recombinant antibodies, tribodies or bibodies, intrabodies, nanobodies, camelized antibodies, and $V_H$H-containing antibodies.

Examples of camelized antibodies targeting beta-lactamase are known in the art. See, e.g., Conrath et al., *Antimicrob. Agents Chemother.* 2001, 2807-2812.

Additional examples of antigen-binding antibody fragments include an antigen-binding antigen fragment of an IgG (e.g., an antigen-binding fragment of IgG1, IgG2, IgG3, or IgG4)) (e.g., an antigen-binding fragment of a human or humanized IgG, (e.g., human or humanized IgG1, IgG2, IgG3, or IgG4)); an antigen-binding fragment of an IgA (e.g., an antigen-binding fragment of IgA1 or IgA2 (e.g., an antigen-binding fragment of a human or humanized IgA (e.g., a human or humanized IgA1 or IgA2)); an antigen-binding fragment of an IgD (e.g., an antigen-binding fragment of a human or humanized IgD); an antigen-binding fragment of an IgE (e.g., an antigen-binding fragment of a human or humanized IgE); or an antigen-binding fragment of an IgM (e.g., an antigen-binding fragment of a human or humanized IgM)). Additional examples of antigen-binding antibody fragments are known in the art.

The term "monoclonal antibody" refers to a population of antibody molecules that contain only one species of an antigen-binding site capable immune-reacting with a particular epitope of a protein.

For example, monoclonal IgY can be produced using phage display library screening. Briefly, the antibody library is screened to identify and isolate phages that express an antibody that binds to a beta-lactamase (e.g., TEM-1) and/or to a beta-lactamase-producing bacteria (e.g., a TEM-1-producing bacteria (e.g., a TEM-1-producing E. coli)). Following screening, the display phage is isolated and the nucleic acid encoding the selected antibody can be recovered from the display phage and sub-cloned into other expression vectors by recombinant DNA techniques known in the art. The nucleic acid can be further manipulated (e.g., linked to nucleic acid encoding additional immunoglobulin domains, such as additional constant regions) and/or expressed in a host cell. As another example, monoclonal IgYs can be produced using well-known molecular cloning and cell fusion techniques.

For example, peptide of TEM-1 (e.g., any of the peptides described herein, Peptides 1-25) is administered, e.g., via intraperitoneal injection to an avian subject (e.g., a chicken) to induce an immune response (e.g., a humoral immune response). Immune cells are isolated from the thymus, bursa fabricius, bone marrow, spleen, or lymphoid nodules and fused with myeloma cells as previously described (see, e.g., Kohler and Milstein, Nature 1975, 256:495-497). The resulting hybrid cells are then subcloned using limited dilution to isolate individual hybrid cells producing the desired monoclonal IgYs. As noted above, the polyclonal IgYs described herein can be modified to generate monoclonal antibodies, humanized antibodies, or human antibodies using methods known in the art, such as the hybridoma technique as originally developed by Kohler and Milstein, Nature 256: 495-497, 1975, the human B cell hybridoma technique (see, e.g., Kozbar et al., Immunology Today 4:72, 1983), and the EBV-hybridoma technique to produce monoclonal antibodies (see, e.g., Cole et al., Monoclonal Antibodies and Cancer Therapy, Alan R. Liss, pp. 77-96, 1985).

Monoclonal antibodies can also be made by harvesting antibody-producing cells, e.g., splenocytes from transgenic mice expressing human immunoglobulin genes, and which have been immunized with inactivated beta-lactamase-producing bacteria (e.g., any of the inactivated beta-lactamase-producing bacteria described herein (e.g., TEM-1-producing bacteria (e.g., TEM-1-producing E. coli))) or a beta-lactamase (e.g., any of the beta-lactamases described herein (e.g., TEM (e.g., TEM-1))). The splenocytes can be immortalized through fusion with human myelomas, or through the transformation with Epstein-Barr virus (EBV) (see, e.g., EP 614984). Hybridoma cells producing monoclonal antibodies that bind to inactivated beta-lactamase-producing bacteria (e.g., any of the inactivated beta-lactamase-producing bacteria described herein (e.g., TEM-1-producing bacteria (e.g., TEM-1-producing E. coli))) or a beta-lactamase (e.g., any of the beta-lactamases described herein (e.g., TEM (e.g., TEM-1))) are detected by screening the hybridoma culture supernatants, e.g., using enzyme linked immunosorbent assays (ELISA). Hybridoma cells that test positively in the screening assays described herein can be cultured in culture medium under conditions and for a time sufficient to allow the hybridoma cells to secrete the desired monoclonal antibodies. The desired monoclonal antibodies can be collected and purified using any of the purification methods described herein or known in the art.

In some embodiments of any of the methods described herein, combinations of two or more of the monoclonal antibodies, or antigen-binding fragments thereof can be used.

The term "humanized antibody" refers to an antibody that has been engineered to comprises one or more human framework regions in the variable region together with non-human (e.g., chicken, mouse) complementarity-determining regions (CDRs) of the heavy and/or light chain. In some embodiments, a humanized antibody comprises sequences that are entirely human except for the CDR regions. Humanized antibodies are typically less immunogenic to humans, relative to non-humanized antibodies, and thus offer therapeutic benefits in certain situations. However, IgYs are already known to be less immunogenic than other types of antibodies. Humanized antibodies are known in the art, and techniques for generating humanized antibodies are also known. See, e.g., Queen et al., Proc. Natl. Acad. Sci. U.S.A. 86:10029-10033, 1989; Jones et al., Nature 321:522-525, 1986; Orlandi et al., Proc. Natl. Acad Sci. U.S.A. 86:3833-3837, 1989.

In some embodiments, humanized versions of any of the IgYs described herein can be made by replacing one or more (e.g., one, two, three, four, five, or six) amino acids of the framework region.

Epitope imprinting can also be used to produce a "human" antibody polypeptide dimer that retains the binding specificity of the antibodies disclosed herein. Briefly, a gene encoding a non-human variable region ($V_H$) with specific binding to an antigen and a human constant region (CH1), is expressed in E. coli and infected with a phage library of human VλCλ genes. Phages displaying antibody fragments are then screened for binding to any of the beta-lactamase-producing bacteria described herein (e.g., any of the TEM-1-producing bacteria described herein) or any of the beta-lactamases described herein (e.g., TEM-1). Selected human V % genes are re-cloned for expression of VλCλ chains and E. coli bacteria harboring these chains are infected with a phage library of human VHCH1 genes and the library is subject to rounds of screening with antigen-coated tubes (See Hoogenboom et al., PCT publication WO 93/06213).

As used herein, "full human antibodies" are antibodies or antigen-binding fragments of antibodies that contain only human-derived amino acid sequences. For example, a fully human antibody can be produced from a human B-cell or a human hybridoma cell.

The term "chimeric antibody" refers to an antibody that has been engineered to comprise at least one human constant region. For example, one or all (e.g., one, two or three) of the variable regions of the light chain(s) and/or one or all (e.g., one, two or three) of the variable regions of the heavy chain(s) of an avian antibody (e.g., a monoclonal IgY) can each be joined to a human constant region, such as, e.g., to an IgG1 human constant region.

Chimeric monoclonal antibodies can be produced by recombinant DNA techniques known in the art. See, e.g., U.S. Pat. Nos. 4,816,567; 4,978,775; 4,975,369; and 4,816,397.

In some embodiments of any of the IgY described herein, the antigen-binding domain binds with a $K_D$ of about $1\times10^{-1}$ M to about $1\times10^{-11}$ M (e.g., about $1\times10^{-1}$ M to about $1\times10^{-8}$ M, about $1\times10^{-6}$ M to about $1\times10^{-11}$ M, or about $1\times10^{-8}$ M to about $1\times10^{-4}$ M) to the antigen.

A variety of different methods known in the art can be used to determine the $K_D$ values of any of the IgYs or antigen-binding fragments described herein (e.g., an electrophoretic mobility shift assay, a filter binding assay, surface plasmon resonance, a biomolecular binding kinetics assay, etc.).

Methods of Making IgY Against TEM-1 and Against TEM-1-Producing Bacteria

Provided herein are methods of making a IgY against a TEM-1 beta-lactamase or a TEM-1 antigen in an avian subject that include: administering to the avian subject: (i) a polypeptide composition comprising an amino acid sequence including an amino acid sequence that is at least 80% (e.g., at least 82%, at least 84%, at least 85%, at least 86%, at least 88%, at least 90%, at least 92%, at least 94%, at least 95%, at least 96%, at least 97%, at least 98%, or at least 99%) identical to SEQ ID NO: 1, SEQ ID NO: 2, and/or SEQ ID NO: 3; or (ii) an inactivated whole cell of a TEM-1 beta-lactamase-producing bacterial cell, wherein (i) and/or (ii) are administered in an amount sufficient to produce an IgY against the TEM-1 beta-lactamase or the TEM-1 antigen in the avian subject.

In some embodiments of any of the methods described herein, the whole-cell of a TEM-1-producing bacteria is inactivated by heat at temperature of about 50° C. to about 80° C. (e.g., about 50° C. to about 75° C., about 50° C. to about 70° C., about 50° C. to about 65° C., about 50° C. to about 60° C., about 60° C. to about 80° C., about 60° C. to about 70° C., about 70° C. to about 80° C., about 50° C., about 55° C., about 60° C., about 65° C., about 70° C., about 75° C., or about 80° C.).

In some embodiments of any of the methods described herein, the whole-cell of a TEM-1-producing bacterial cell is inactivated by low energy electron beam irradiation. In some embodiments of any of the methods described herein, the inactivated whole-cell of a TEM-1-producing bacterial cell is inactivated by low energy electron irradiation at a range of about 1 to about 10 kGy (e.g., at about 1 to about 8 kGy, about 1 to about 6 kGy, about 1 to about 5 kGy, about 1 to about 4 kGy, about 1 to about 2 kGy, about 1 kGy, about 2 kGy, about 3 kGy, about 4 kGy, about 5 kGy, about 6 kGy, about 7 kGy, about 8 kGy, about 9 kGy, or about 10 kGy).

In some embodiments of any of the methods described herein, the avian subject is a chicken, a turkey, a goose, a quail, a pheasant, or a duck.

In some embodiments of any of the methods described herein, (i) or (ii) are administered intramuscularly to the subject.

In some embodiments of any of the methods described herein, the methods further include administering to the avian subject an adjuvant (e.g., any of the exemplary adjuvants described herein) and/or a pharmaceutically acceptable carrier (e.g., any of the pharmaceutically acceptable carriers described herein).

In some embodiments of any of the methods described herein, the amino acid sequence including a sequence that is at least 80% identical to SEQ ID NO: 1, SEQ ID NO: 2, SEQ ID NO: 19, SEQ ID NO: 20, SEQ ID NO: 21, SEQ ID NO: 22, SEQ ID NO: 23, SEQ ID NO: 24, SEQ ID NO: 25, and/or SEQ ID NO: 26 is conjugated via a linker (e.g., KLH, CCH, OVA, or BSA).

In some embodiments of any of the methods described herein, the method further includes administering an additional dose (e.g., one, two, three, or four doses) of (i) or (ii) to the avian subject.

In some embodiments of any of the methods described herein, the method further includes recovering a fowl egg from the avian subject including immunoglobulins Y (IgY) against (i) or (ii).

In some embodiments of any of the methods described herein, the method further includes isolating IgY from the fowl egg.

In some embodiments of any of the methods described herein, the method further includes isolating IgY by affinity chromatography (e.g., any of the affinity chromatography methods described herein).

In some embodiments of any of the methods described herein, the method further includes purifying IgY by precipitation (e.g., any of the precipitation methods described herein).

In some embodiments of any of the methods described herein, the method further includes purifying IgY by ultrafiltration.

In some embodiments of any of the methods described herein, the method further includes purifying the IgY by precipitation (e.g., any of the precipitation methods described herein), followed by affinity chromatography (e.g., any of the affinity chromatography methods described herein). In some embodiments of any of the methods described herein, the method further includes purifying the IgY by precipitation (e.g., any of the precipitation methods described herein), affinity chromatography (e.g., any of the affinity chromatography methods described herein), ultrafiltration, or any combination thereof.

Methods of Inducing Bacterial Death

Provided herein are methods of inducing bacterial cell death that include: contacting a gram negative bacteria (e.g., any of the gram negative bacteria described herein) with any of the IgYs described herein (e.g., any of the exemplary IgYs described herein against TEM-1 producing bacteria, or any of the exemplary IgYs described herein against TEM-1 (e.g., whole TEM-1 or peptide of a TEM-1 active site), wherein contacting results in inducing bacterial cell death (e.g., necrosis or apoptosis).

Antibodies (e.g., IgY antibodies) as described herein can be used as a broad-spectrum treatment against a variety of ESBL-producing bacteria, such as *E. coli*. Antibodies directed against the specific peptide antigen compositions described herein, such as aTIgY and ap2IgY, which was developed against TEM-1 should also target other TEM derivatives (e.g., TEM-59, TEM-76, CMT-3, TEM-211, TEM-193, TEM-5, TEM-24, TEM-86, TEM-114, TEM-121, TEM-130, TEM-131, TEM-136, TEM-177 and TEM-22), as they have similar 3D structure with single amino acids mutations in the sequence. For example, ap2IgY was generated against catalytic and conservative residues, which are characteristic of the whole class A of beta-lactamases.

In some embodiments of any of the methods described herein, the IgY is cytotoxic to TEM-1-producing bacteria (e.g., TEM-1 producing *E. coli*).

In some embodiments of any of the methods described herein, the IgY is cytostatic to TEM-1-producing bacteria (e.g., TEM-1 producing *E. coli*), and in conjunction with contacting with the at least one antibiotic (e.g., any of the exemplary antibiotics described herein) results in bacterial cell death (e.g., necrosis or apoptosis).

In some embodiments of any of the methods described herein, the gram negative bacteria are an extended spectrum beta lactamase (ESBL)-producing bacteria. In some embodiments, the ESBL-producing bacteria are bacteria selected from the group consisting of: *E. coli, Klebsiella pneumonia, Acinetobacter baumannii*, and *Pseudomonas aeruginosa.*

In some embodiments of any of the methods described herein, the gram negative bacteria are TEM, e.g., TEM-1, beta-lactamase-producing bacteria. In some embodiments, the TEM beta-lactamase-producing bacteria is a TEM-1 beta-lactamase-producing *E. coli*, a TEM-1 beta-lactamase-producing *Klebsiella peumoniae*, a TEM-1 beta-lactamase-producing *Acinetobacter baumannii* or a TEM-1 beta-lactamase-producing *Pseudomonas aeruginosa.*

In some embodiments of any of the methods described herein, contacting further includes contacting the gram negative bacterial cell with at least one antibiotic is selected from the group consisting of pencillin, benzylpenicillin, ampicillin, cefaloridine, ceftazidime, cefazolin, cefotaxime, cephalotin, aztreonam, colistin, fosfomycin, and temocillin.

The number of bacterial cells in a sample can be determined using a number of different assays, e.g., growth curves, standard plate count, or turbidimetric measurement. Additional assays of determining bacterial cell death are known in the art.

Methods of Treating a Bacterial Infection

Provided herein are methods of treating a beta-lactamase-producing, gram negative bacterial infection in a subject that include: orally administering to a subject in need of treatment a therapeutically effective amount of an immunoglobulin Y (IgY) against beta-lactamase (e.g., any of the IgYs against beta-lactamase described herein); and administering to the subject a therapeutically effective amount of at least one (e.g., two, three, four, or five) antibiotic(s) for a time sufficient to treat the beta-lactamase-producing, gram negative bacterial infection in the subject.

Also provided herein are methods of inhibiting a beta-lactamase-producing, gram negative bacterial infection in a subject that include: orally administering to a subject in need of treatment a therapeutically effective amount of an immunoglobulin Y (IgY) against beta-lactamase (e.g., any of the IgYs against beta-lactamase described herein); and administering to the subject a therapeutically effective amount of at least one (e.g., two, three, four or five) antibiotic(s).

In some embodiments of any of the methods described herein, any of the IgYs described herein are used for an oral passive immunization against beta lactamase, e.g., TEM-1, producing bacteria, such as *E. coli.*

In some embodiments of any of the methods described herein, any of the IgYs described herein are orally administered in combination with at least one antibiotic, e.g., an antibiotic normally inhibited by beta lactamase. In some embodiments of any of the methods described herein, any of the IgYs described herein are orally administered as a replacement for an existing antibiotic treatment.

In some embodiments of any of the methods described herein, the method further includes identifying the subject as being at risk of having or developing a beta-lactamase-producing, gram negative bacterial infection.

In some embodiments of any of the methods described herein, the bacterial infection is a bacterial infection of the colon, or a bacterial infection within the lumen of the intestinal tract.

In some embodiments of any of the methods described herein, the bacterial infection is caused by bacteria that are resistant to an antibiotic (e.g., third generation cephalosporins).

In some embodiments of any of the methods described herein, the bacterial infection is a nosocomial infection (e.g., hospital-acquired infection).

In some embodiments of any of the methods described herein, the administration of any of the IgYs described herein, e.g., any of the IgYs against beta-lactamase described herein, any of the IgYs against beta-lactamase-producing bacteria described herein, e.g., any of the IgYs against TEM-1-producing bacteria described herein, e.g., any of the IgYs against TEM-1-producing *E. coli* described herein, is stopped before the administration of the at least one (e.g., two, three, four or five) antibiotic(s).

In some embodiments of any of the methods described herein, orally administering occurs at least 1×, 2×, 3×, 4×, 5×, 6×, 7×, 8×, 10×, or more per week.

In some embodiments of any of the methods described herein, the IgY and the at least one antibiotic are administered in conjunction with another treatment.

In some embodiments of any of the methods described herein, treating includes:

reducing the number of beta-lactamase-producing bacteria (e.g., any of the beta-lactamase-producing bacteria described herein (e.g., any of the TEM-1-producing bacteria described herein (e.g., TEM-1 producing *E. coli*))) in a tissue and/or organ (e.g., colon, intestines) of the subject;

delaying progression of the bacterial infection (e.g., any of the infections by beta-lactamase-producing bacteria described herein);

decreasing the risk of developing antibiotic resistance to the at least one antibiotic administered to the subject; or decreasing the rate of and/or delaying pathogenic bacterial growth (e.g., bacterial growth of any of the beta-lactamase-producing bacteria described herein (e.g., any of the TEM-1-producing bacteria described herein (e.g., TEM-1-producing *E. coli*))) in the subject.

As used herein, treating includes "prophylactic treatment," which means reducing the incidence of or inhibiting (or reducing the risk of) a potential pathogenic bacterial infection (e.g., infections by any of the beta-lactamase-producing bacteria described herein (e.g., any of the TEM-1-producing bacteria described herein (e.g., TEM-1-producing *E. coli*))) in a subject (e.g., any subject described herein, an avian subject, a mammalian subject, or a human subject).

The term "therapeutic treatment" refers to reducing symptoms or effects of an existing pathogenic bacterial infection ((e.g., infections by any of the beta-lactamase-producing bacteria described herein (e.g., any of the TEM-1-producing bacteria described herein (e.g., TEM-1-producing *E. coli*))), reducing progression of a pathogenic bacterial infection ((e.g., infections by any of the beta-lactamase-producing bacteria described herein (e.g., any of the TEM-1-producing bacteria described herein (e.g., TEM-1-producing *E. coli*))), reducing the severity of a pathogenic bacterial infection (e.g., (e.g., infections by any of the beta-lactamase-producing bacteria described herein (e.g., any of the TEM-1-producing bacteria described herein (e.g., TEM-1-producing *E. coli*))), and/or reducing re-occurrence in a subject.

The idea of oral administration of IgYs specific to pathogens would be definitely an attractive approach, especially against pathogens infecting the gastrointestinal track. There are several human studies on IgY-based therapies, e.g., against *S. mutans, P. gingivalis, H. pylori, P. aeruginosa* and *C. albicans*.

Eggs as an everyday food product do not cause the risk of toxic side effects. Concerns about allergy reactions are not necessary, as typical egg white allergens like ovomucoid, lysozyme, ovalbumin and ovotransferrin, as well as egg yolk allergens like livetin, phosvitin and apovitillin are not present in an extracted and affinity purified IgYs batch. An IgY itself does not activate the mammalian complement system, does not interact with rheumatoid factors, proteins A and G, nor with mammalian Fc receptors (Schade et al., *Altern. Lab. Anim.* 2005, 33:129-154). As an egg's component, IgYs are consider as save and non-toxic. An allergy to eggs can be overtaken by affinity purification, separating IgYs from other proteins. Additionally, immunotherapy does not cause bacterial resistance.

The stability of IgYs in harsh conditions can be increased by additives and different encapsulation methods. For example, added sorbitol can suppress the inactivation of IgY in low a pH (Lee et al., *J. Biochem. Mol. Biol.* 2002, 35:488-493). Similar effects can be observed in the presence of sucralfate and sucrose (Xun et al., *Afr. J. Microbiol. Res.* 2010, 4:1091-1099; and Akita et al., *Egg Nutrition and Biotechnology* CABI Pub 2000). Encapsulation using gelatin or chitosan-alginate capsules, methacrylic acid copolymer also prevent from proteolytic digestion and denaturation, keeping preserving IgY activity (Li et al., *Appl. Biochem. Biotechnol.* 2009, 159:778-787; Akita et al., *Egg Nutrition and Biotechnol CABI Pub* 2000; Kovacs-Nolan et al., *J. Immunol. Methods* 2005, 296:199-209; and Li et al., *Vet. Immunol. Immunopathol.* 2009, 129:132-136).

Compositions and Diagnostic Kits, Research Kits and Therapy Kits

Also provided herein are compositions (e.g., pharmaceutical compositions) that include any of the antibodies described herein. In some embodiments, the compositions (e.g., pharmaceutical compositions) that include any of the antibodies described herein can be contained in a sterile vial or a pre-loaded syringe. In some embodiments, the disclosure includes specific antibodies combined with a secondary material: antibody, fragment hooked to solid phase, fragment with label such as a chromophore. The antibodies and/or kits can be used for purification, detection, cell killing, or bound to a polymer to allow for ease of elimination from the body.

In some embodiments, the compositions (e.g., pharmaceutical compositions) that include any of the antibodies, e.g., IgYs, described herein are formulated for oral administration. In some embodiments, the compositions (e.g., pharmaceutical compositions) that include any of the IgYs described herein are formulated as a liquid, a solid, or a semi-solid. In some embodiments of any of the compositions (e.g., pharmaceutical compositions) that include any of the IgYs described herein, the composition (e.g., pharmaceutical composition) is a gel, a capsule, a gel-capsule, a tablet (e.g., a fast disintegrating tablet), an ointment, a freeze-dried powder, a lyophilized powder, a solution, a lozenge, a spray, a drop, a strip, or a film (e.g., a thin film, a fast-dissolving film). In some embodiments of any of the compositions (e.g., pharmaceutical composition) that include any of the IgYs described herein, the composition (e.g., pharmaceutical composition) is in the form of a salve, a paste, a solution, a powder, or any combination thereof. In some embodiments of any of the compositions (e.g., pharmaceutical compositions) that include any of the IgYs described herein, the composition (e.g., pharmaceutical composition) includes a binding agent (e.g., gelatin), a sweetener (e.g., dextrose, *stevia*, aspartame, fructose, glucose, mannitol, sorbitol, sugar, or sucrose), a flavoring agent (e.g., menthol, cherry flavor, orange flavor, berry flavor, pineapple flavor), a coloring agent, a wetting agent, an emulsifying agent, a perfuming agent, an antibacterial agent, a dispensing agent, or proteinase inhibitors.

As described herein, compositions (e.g., pharmaceutical compositions) including any of the IgYs described herein are formulated for oral administration, such that the composition (e.g., pharmaceutical composition) is not deactivated at low pH values (e.g., pH 1 to about pH 5).

In some embodiments of any of the compositions (e.g., pharmaceutical compositions) that include any of the IgYs described herein, the composition (e.g., pharmaceutical composition) is released in a controlled- or sustained-release formulation.

In some embodiments of any of the compositions (e.g., pharmaceutical compositions) that include any of the IgYs described herein, the composition (e.g., pharmaceutical composition) is a food additive. In some embodiments of any of the compositions (e.g., pharmaceutical composition) that include any of the IgYs described herein, the composition (e.g., pharmaceutical composition) is added to a yogurt beverage (e.g., a probiotic yogurt beverage). Probiotics are defined as live micro-organisms that improve the homeostasis of intestinal micro flora, such as *Lactobacillus* species (e.g., *Lactobacillus acidophilus, Lactobacillus brevis, Lactobacillus bulgaricus, Laclobacillus casei, Lactobacillus cellobiosus, Lactobacillus crispatus, Lactobacillus curvalus, Lactobacillus fermentum, Lactobacillus gasseri, Lactobacillus plantarum, Lactobacillus salivarus*), *Bifidobacterium* species (e.g., lactic acid bacteria, *Bifidobaclerium bifidum, Bifidobacterium animalis, Bifidobacterium thermophilun, Bifidobacterium longum, Bifidobacteriun infantis, Bifidobacterium lactis*) and yeasts (e.g., *Saccharomyces boulardii, Saccharomyces cerevisiae*).

In some embodiments, the compositions (e.g., pharmaceutical compositions) that include at least one (e.g., two, three, four, or more) antibiotic (e.g., any of the antibiotics described herein) are formulated for different routes of administration (e.g., intravenous, subcutaneous, or intramuscular).

Also provided herein are compositions (e.g., pharmaceutical compositions) that include at least one (e.g., two, three, four or more) of any of the IgYs described herein and at least one (e.g., two, three, four or more) of any of the antibiotics described herein.

In some embodiments of any of the compositions described herein, the compositions (e.g., pharmaceutical compositions) that include any of the IgYs described herein can include a pharmaceutically acceptable carrier (e.g., phosphate buffered saline). In some embodiments, any of the pharmaceutical compositions described herein can include one or more buffers (e.g., a neutral-buffered saline, a phosphate-buffered saline (PBS)), one or more carbohydrates (e.g., glucose, manose, sucrose, dextran, or mannitol), one or more antioxidants, one or more chelating agents (e.g., glutathione or EDTA), one or more preservatives, and/or a pharmaceutically acceptable carrier (e.g., PBS, saline, or bacteriostatic water).

As used herein, the term "pharmaceutically acceptable carrier" includes solvents, dispersion media, antifungal agents, coatings, isotonic and absorption delaying agents, and the like, compatible with pharmaceutical administration.

Single or multiple administrations of any of the pharmaceutical compositions described herein can be given to a subject depending on, for example, the dosage and frequency as required and tolerated by the subject. A dosage of the pharmaceutical composition including any of the IgYs described herein should provide a sufficient quantity of the IgY to effectively ameliorate or treat symptoms, conditions or diseases (e.g., about 1 µg/kg to about 100 mg/kg per day). Toxicity and therapeutic efficacy of compositions can be determined using conventional procedures in cell cultures, pre-clinical models (e.g., birds, mice, rats or monkeys), and humans. Data obtained from in vitro assays and pre-clinical studies can be used to formulate the appropriate dosage of any of the compositions described herein (e.g., any of the pharmaceutical compositions described herein).

Also provided herein are kits that include at least one (e.g., two, three, four or more) of any of the IgYs described herein. Also provided herein are kits that include at least one (e.g., two, three, four or more) of any of the IgYs described herein or at least one (e.g., two, three, four or more) of any of the antibiotics described herein. In some embodiments, the kits can include instructions for performing any of the methods described herein. In some embodiments, the kits can include at least one dose of any of the compositions (e.g., antibody compositions) described herein including any of the IgYs described herein. In some embodiments, the kits can provide a syringe for administering any of the pharmaceutical compositions described herein.

One of the embodiments herein is a therapeutic, a diagnostic, or a research reagent using modified immunoglobulins and their variants as described herein. These can combine a second antibody with the antibodies described herein for use in the production of research tools or therapeutic antibody heavy-chain or light-chain scaffolds. As with any new material, there can be a need to develop a custom method for analysis. Such analysis might require creating partner materials, possibly using antibodies or antigen-binding fragments. The peptide antigens, the antibodies and the antigen-binding fragments can be bound to a substrate, either through a non-covalent bond or molecular interactions, such that it can capture the other half of it's binding pair.

The antibody compositions can be used for point-of-care diagnostic tools: Earlier detection. Detect extremely low level of beta-lactamase to know sooner when to start treatment with a different antibiotic or with an appropriate neutralizing antibody adjunct. Therapy selection: Adjunctive treatment selection: point-of-care diagnostic test. Grid of specific antibodies/antigen-binding fragments to determine which specific antibody should be prescribed for treatment.

A diagnostic kit based on the lateral flow test or lateral immunochromatographic assays for the detection of the antibiotic resistance of the infective factor characterized in that said kit is a diagnostic assay contains a set of antibodies, preferably monoclonal antibodies, for detection of antibiotic resistance by detection of the presence of lack of the given antibiotic wherein said antibiotics are betalactams in biological fluids.

Without further description, it is believed that one of ordinary skill in the art can, using the preceding description and the following illustrative examples, make and utilize the IgY proteins of the present invention and practice the claimed methods. The following working examples specifically point out various aspects of the present invention, and are not to be construed as limiting in any way the remainder of the disclosure.

Without further description, it is believed that one of ordinary skill in the art can, using the preceding description and the following illustrative examples, make and utilize the IgY proteins of the present invention and practice the claimed methods. The following working examples specifically point out various aspects of the present invention, and are not to be construed as limiting in any way the remainder of the disclosure.

EXAMPLES

Example 1. Catalytic Site and Conservative Residues in TEM-1 Structure Identified as Potential Targets for IgYs Amino acid sequence analysis of TEM-1 protein was performed using UniProt (*Nucleic Acids Res.* 2017, 45:D158-D169) (access id P62593) and RCBS PDB (Berman et al., *Nucleic Acids Res.* 2000, 28:235-242) (access id 1axb and 1btl). The catalytic sites and conservative residues were identified using Hydrolases Catalytic Sites database (enzyme.chem.msu.ru), Catalytic Site Atlas (Furnham et al., *Nucleic Acids Res.* 2014, 42:D485-489) and HotSpot Wizard (Pavelka et al., *Nucleic Acids Res.* 2009, 37:W376-W383), additionally complemented by analysis of Lahey ß-lactamase database (Lahey Clinic). Protein visualization was performed by using Chimera software (Pettersen et al., *J. Comput. Chem.* 2004, 25:1605-1612).

Within the 263 amino acids of TEM-1, 7 amino acids are identified as important residues in catalytic site: S70, Lys73, Ser130, Lys234, Glu166, Asn170 and Ala237. These residues have been associated with a specific role in the hydrolysis of beta-lactam antibiotics.

Ser70 acts as a nucleophile in the attack on ß-lactam substrate carbonyl group, interacts with Glu166, stabilizes the tetrahedral intermediate during the process of acylation and deacylation and interacts with Lys73 by forming an ion pair together.

Lys73 is involved in deprotonation of Ser70 actin as a general base in the acylation reaction and directs the hydroxyl group of S70 for the effective catalytic reaction, it also interacts with residue Glu166 through a hydrogen bond.

Ser130 belongs to the hydrogen bonding network mediating protonation of the beta-lactam ring nitrogen and interacts with Lys234 and oxygen 12 from the carboxylate group of ß-lactam.

Glu166 acts as a catalytic base towards the water molecule, what leads to deprotonation of Ser70 in the reaction of acylation and to the attack of the water molecule on the carbon of beta-lactam linked to the oxygen gamma of the residue S70 in the reaction of deacylation.

Asn170 coordinates the water molecule by forming a hydrogen bond through its side chain and takes part in a proton transport from Ser70 to Lys73 in the acylation reaction.

Lys234 recognizes beta-lactams at the initial step, electrostatically interacts with their carboxylate group and stabilizes transition states of the Michaelis-Menten complex. Lys234 also takes part in the protonation of beta-lactam nitrogen in the acylation reaction and interacts with S130 via a hydrogen bond.

Ala237 stabilizes a tetrahedral intermediate through the oxyanion hole which forms together with residue S70 (Brown et al., *J. Biol. Chem.* 2009, 284:33703-33712; Chen et al., *Biochemistry* 1996, 35:12251-12258; Vandavasi et al., *J. Med Chem.* 2016, 59:474-479; Lamotte-Brasseur et al., *Biochem. J.* 1991, 279:213-221; Atanasov et al., *Proc. Natl. Acad. Sci. U.S.A.* 2000, 97:3160-3165; Hart et al., *Nat. Commun.* 2016, 7:12965; Furnham et al., *Nucleic Acids Res.* 2014, 42: D485-489; Damblon et al., *Proc. Natl. Acad. Sci.*

U.S.A. 1996, 93:1747-1752; Vandavasi et al., *Antimicrob. Agents Chemother.* 2017, 61:e01636-01646).

The Hot Spot Wizard analysis showed that in the crystal structure of TEM-1 9 pockets can be found and the residues S70, S130, Lys234 and Ala237 all belong to the pocket 3, which is characterized as a catalytic pocket. The active site is situated between two domains of TEM-1 and consist of four important structural elements: 1) helix H2 which forms a bottom of an active site, the residues S70 and K73 are located here; 2) the SDN loop which is between helix H4 and helix 5, containing the residue S130; 3) the strand S5 with the residues Lys234 and Ala237; and 4) 0-loop between amino acids 164-179 which forms a rim over the active site and contains residues Glu166 and Asn170. The location of seven residues in the different types of secondary structures was also analyzed: Ser70 and Asn170 are located on the 3(10) type of helix, Lys73 and Glu166 on the alpha helix, and Ser130, Lys234 and Ala237 on the hydrogen-bonded beta strands (Pavelka et al., *Nucleic Acids Res.* 2009, 37:W376-W383; and Fisette et al., *Biophys.* 2010, 98:637-645).

Figure 4:
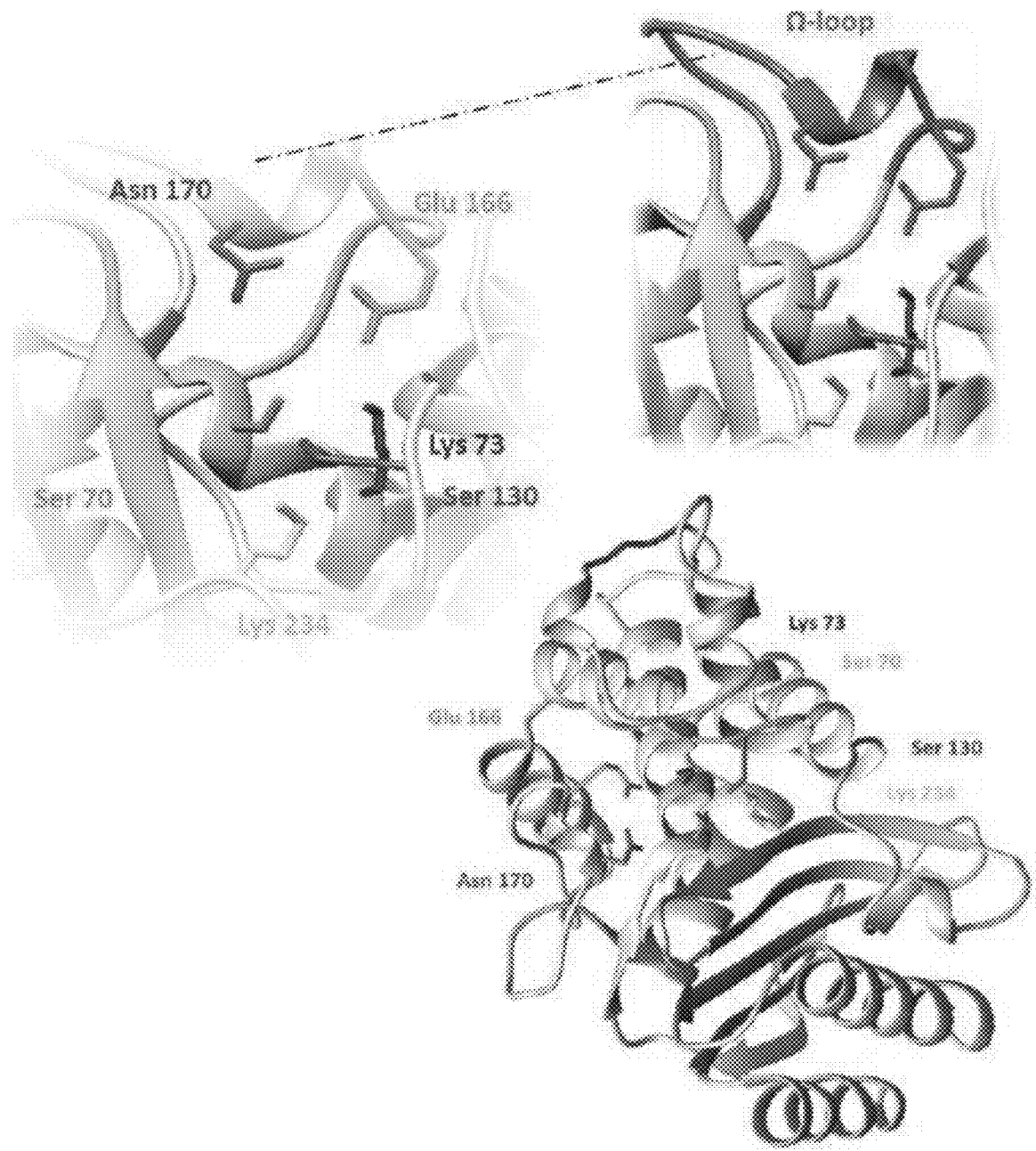
FIG. 4 is a schematic representation of the three-dimensional structure of TEM-1 showing the conserved catalytic amino acids: Ser70, Lys73, Ser130, Glu166, Asn170, and Lys234. The omega (Ω)-loop including Glu166 and Asn170 is also depicted.

Another important parameter taken into account was the mutability score of the 7 chosen catalytic residues in order to find the ones with the lower probability of mutations and therefore developing new TEM mutants. The analysis with Hot Spot Wizard program showed that 6 out of 7 residues were identified as conservative (low mutability): Ser70 (score 2), Lys73 (score 2), Ser130 (score 2), Glu166 (score 3), Asn170 (score 2), Lys234 (score 3) (FIG. 4).
The mutability of the residue Ala237 was predicted at the level of 5, which is defined as moderate.

When compared with the Lahey database, the mutability of these residues among 223 of TEM-1 derivatives was as follows: Ser130- was substituted by Gly residue in derivatives TEM-59 (gene bank accession AF062386), TEM-76 (AF190694), CMT-3 (AY039040) and by Thr in TEM-211 (KF513179); Glu166-residue was replaced by Gly in TEM-193 (JN935135); Asn170 no substitutions were reported; Ala237—substituted by Thr in derivatives: TEM-5 (no accession code), TEM-24 (X65253), TEM-86 (AJ277415), TEM-114 (AY589495), TEM-121 (AY271264), TEM-130 (AJ866988), TEM-131 (AY436361), TEM-136 (AY826417), TEM-177 (FN652295) and by Gly in TEM-22 (Y17583).

For the residues: Ser70 and Lys73 data was not available, it might be due to their critical role and presence in the whole class A of 8-lactamases. Data was also not available for Lys234.

This data was consistent with Brown et al., *J. Biol. Chem.* 2009, 284:33703-33712. Brown aligned the amino acid sequences of the Ω-loop of different representatives of beta-lactamases types from class A and it was established that more than 96% of beta-lactamases class A had the residue Asn at the position 170 and all of them had the Glu at the position 166.

Based on the summary of this data analysis, the following optimal candidate target residues for the IgY development against the active site of TEM-1 were chosen: Ser70, Lys73, Glu166 and Asn170. All of them show low mutability tendency and they play a crucial role in beta-lactams hydrolysis. Moreover, they are situated in strategically good locations in TEM-1 structure (bottom of the active site and Ω-loop above the active site) and they could be paired, which was convenient for choosing the sequences for short peptides synthesis (e.g., Peptide 1, Peptide 2) mimicking the active site.

Figure 5A:
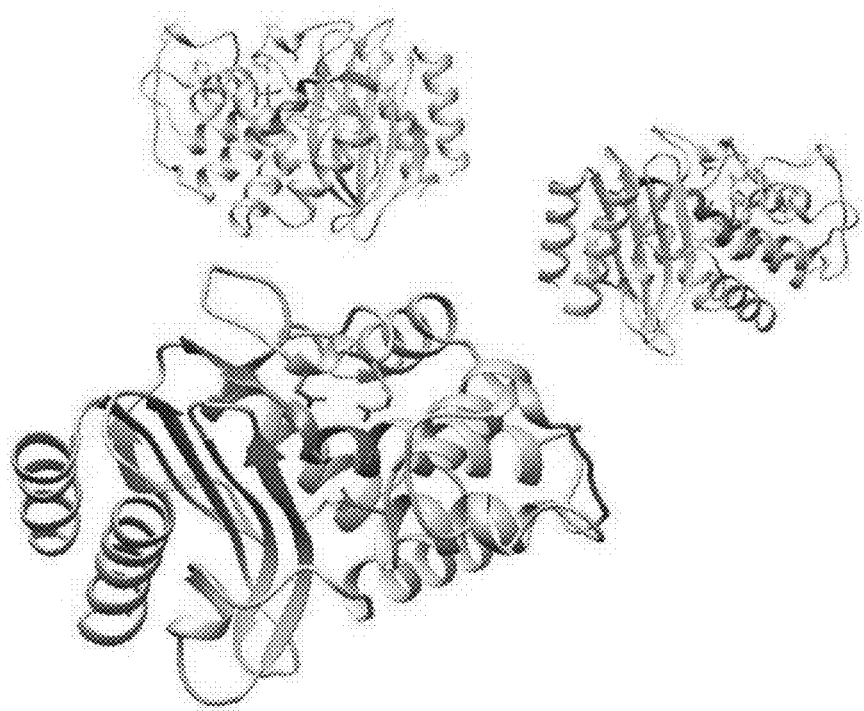
FIG. 5A is a set of three views of schematic representations of Peptide 1 (RFPMMSTFKVL; SEQ ID NO: 1) within the TEM-1 protein.
Figure 5B:
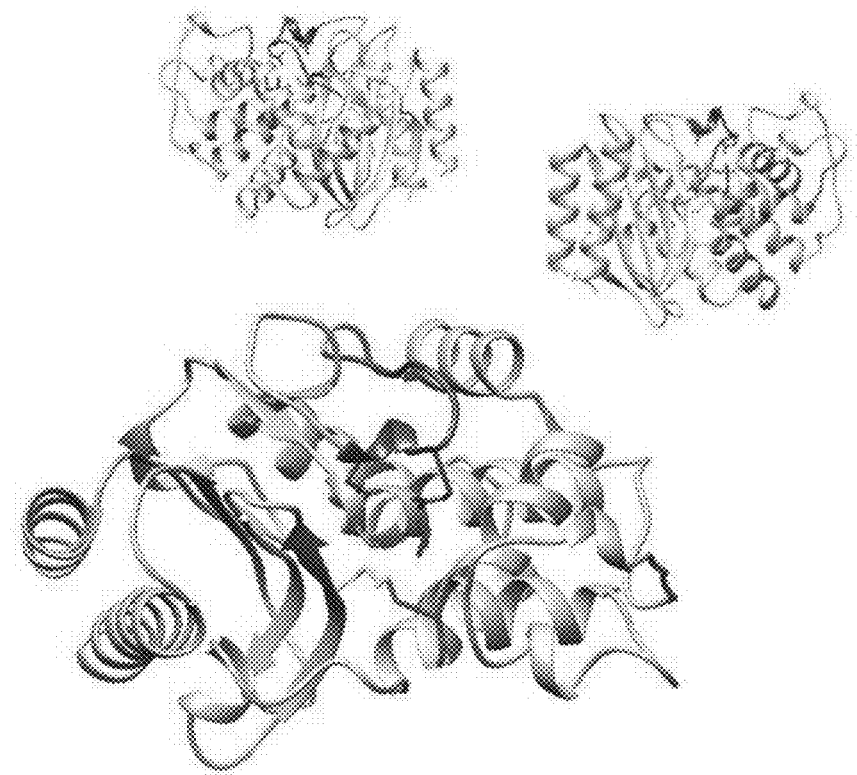
FIG. 5B is a set of three views of schematic representations of Peptide 2 (TRLDRWEPELN; SEQ ID NO: 2) within the TEM-1 protein.
Figure 6:
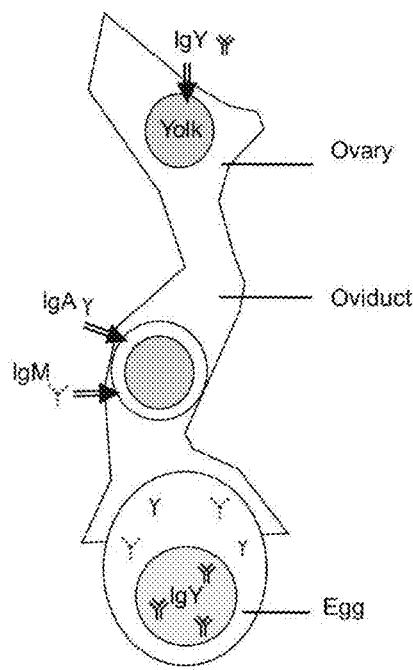
FIG. 6 is a schematic representation of avian immunoglobulin distribution during egg development.
Figure 7A:
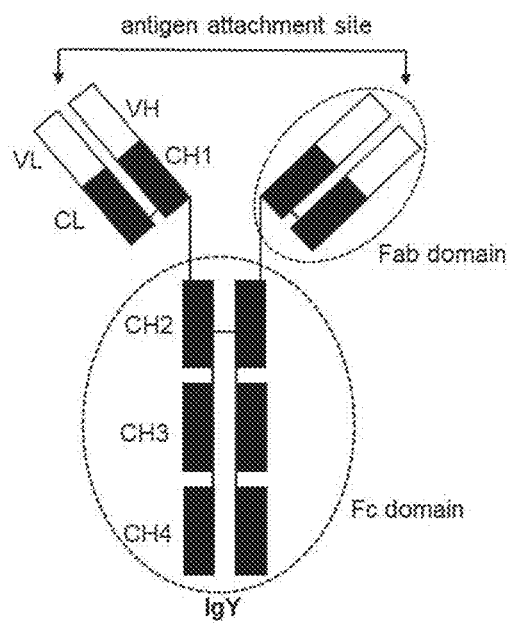
FIG. 7A is a schematic representation of an IgY antibody.
Figure 7B:
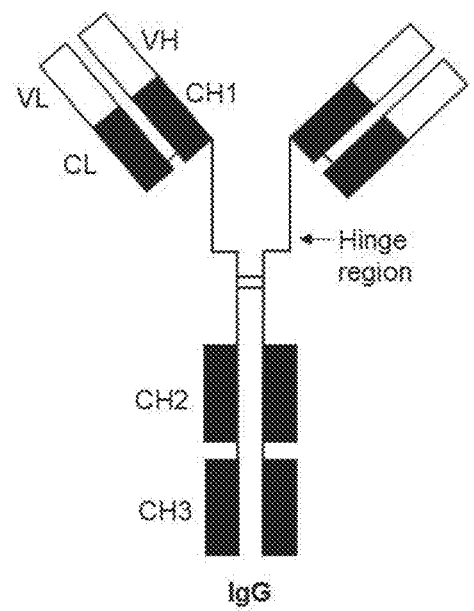
FIG. 7B is a schematic representation of an IgG antibody.

Example 2. Peptide 1 and Peptide 2 Mimic the Functionally Important Structures of the TEM-1 Active Site Based on the bioinformatic analysis of the TEM-1 active site, two sequences of 11 amino acids in length containing specific conservative catalytic residues were selected for peptide synthesis in order to mimic the active site as antigens for specific IgYs development: Peptide 1 (RFPMMSTFKVL; SEQ ID NO: 1) and Peptide 2 (TRLDRWEPELN; SEQ ID NO: 2). Visualization of Peptide 1 and Peptide 2 within TEM-1 as well as visualization of catalytic residues was performed by using Chimera software (Pettersen et al., J. Comput. Chem. 2004, 25:1605-1612) (FIG. 5A and FIG. 5B). Antigenic properties of the selected sequences were determined by Antigen Profiler Peptide Tool.

Peptide 1 (RFPMMSTFKVL; SEQ ID NO: 1) is placed between amino acids 65-75 from the H2 helix and includes residues Ser70 and Lys73 (FIG. 5A). Peptide 2 (TRLDRWEPELN; SEQ ID NO: 2) is located between amino acids 160-170 from the Ω-loop and includes residues Glu166 and Asn170 (FIG. 5B).

The length of both sequences was dictated by general requirements for the generation of IgYs. Sequences of 10-20 amino acids minimalize technical problems with the peptide synthesis. In contrast, antibodies targeting short peptide sequences are very antigen specific, antibodies produced targeting sequences longer than 10 amino acids have higher chances to recognize the native structure of protein. Furthermore, longer sequences recognize a greater number of epitopes. There are several studies on specific IgYs against pathogens, more specifically, IgYs developed against virulent protein fragments or linear short peptides mimicking those where their therapeutical properties were presented. Shin et al. reported effectivity of IgYs against *H. pylori* that were developed against a 15 amino-acids-short peptide mimicking Urease B (Shin et al., *Clin. Diagn. Lab. Immunol.* 2002, 9:1061-1066. Schade et al. 1996 demonstrated the development of specific IgYs against 8 amino-acids cholecystokinin octapeptide for immunohistochemistry assays (Schade et al., *ATLEX* 1996, 13:80-85 Hsieh et al., *J. Microbiol. Immunol. Infect.* 2016, 49:329-334; Shin et al., *J. Med. Microbiol.* 2004, 53:31-34; and Motoi et al., *Vaccine* 2005, 23:3026-3032). Based on these studies the length of 11 amino acids was chosen as the optimal sequence length.

A very important parameter in generating specific antibodies is the antigenicity of the synthesized short peptides. It should be high enough to boost the immune response in immunized chickens in order to produce the required IgYs. To predict the antigenicity of Peptide 1 and Peptide 2, the algorithm-based Antigen Profiler Peptide Tool—provided online by Thermofisher—was used. For Peptide 1 and Peptide 2, the score for theoretical antigenicity was 3 and 4.1 respectively, which described their properties as 'excellent antigens'. Furthermore, a 3D visualization of the sequence 1 and the sequence 2 location in TEM-1 structure was generated (FIG. 5A and FIG. 5B). It was necessary to show if the developed p1IgYs and p2IgY target these sequences in the 3D conformation of TEM-1. Peptide 2 was in the Ω-loop is more exposed than the hidden Peptide 1, which potentially made it an easier target.

Example 3. Generation of IgYs Against the TEM-1 Active Site (p1IgY and p2IgY) and Full-Length TEM-1 (TIgY)

To develop an antigen for TIgY and aTIgY against TEM-1 produced by *E. coli*, a recombinant beta-lactamase TEM protein was used (Ab67672, Abcam plc, Cambridge, UK). For the development of p1IgY and p2IgY, Peptide 1 and Peptide 2 were synthesized de novo using standard techniques and were used as antigens. Peptide 1 and Peptide 2 were conjugated with KLH carrier through the thiol group of an additional Cys residue on the C-terminus of the peptide to increase the immunogenicity of peptides. Peptides were purified on HPLC (p1—96.8%, p2—95.7% purity), tested on MS (Mw p1=1459.86 g/mol; p2=1531.72 g/mol) and lyophilized. Peptide 2 was synthesized using standard techniques and was conjugated with KLH carrier through the thiol group of an additional Cys residue on -C end of the peptide. The peptide was purified on HPLC (95% purity), tested on MS (Mw p2'=1531.72 g/mol) and lyophilized.

Figure 8A:
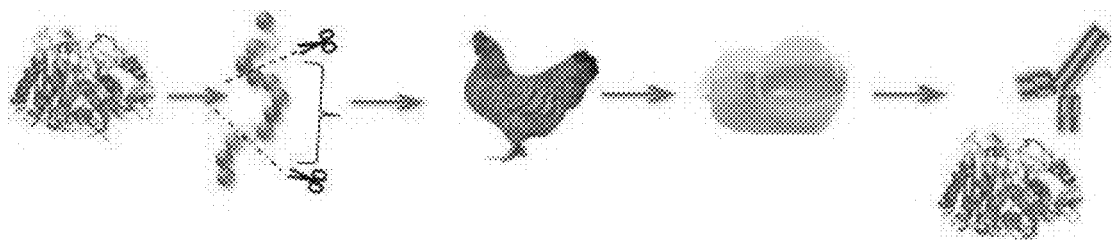
FIG. 8A is a schematic representation of an embodiment of a method described herein.
Figure 8B:
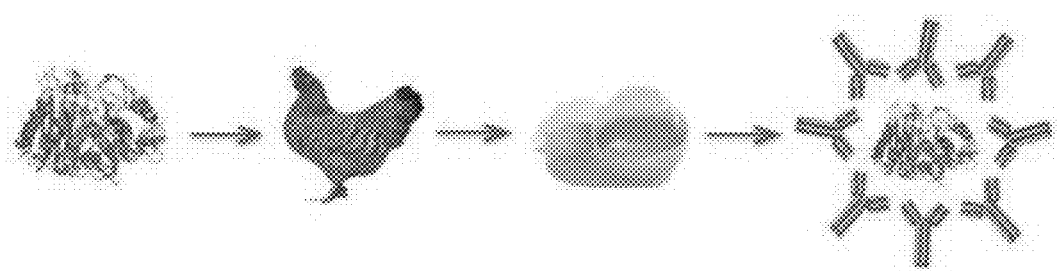
FIG. 8B is a schematic representation of an embodiment of a method described herein.

Chickens were immunized separately with purified Peptide 1 and Peptide 2 and TEM protein (FIGS. 8A and 8B) in four 2-week-long intervals, starting with a primary immunization (1 mg of Peptide 1, Peptide 2, or TEM protein in Freud's complete Adjuvant) and three boosters (three times 0.33 mg Peptide 1, Peptide 2, or TEMprotein in Freud's complete Adjuvant). After 2 weeks eggs were collected and IgYs were purified from egg yolk by a two-step precipitation, then diluted in PBS pH 7.3 containing 0.075% sodium azide. Three IgY fractions were obtained: p1IgY (28.4 mg/ml), p2IgY (30.8 mg/ml) and TIgY (27 mg/ml).

Random non-specific IgYs were used as a control. They were purified from non- or pre-immunized chickens and were as follows: rIIgY (LOT16IgY014E-pi, Gallus Immunotech), rIIIgY (LOT161gY015E-pi), rIIIgY (P075.05, Davids Biotechnologie), rIVIgY (16IgY014K-pi, Gallus Immunotech).

Figure 9A:
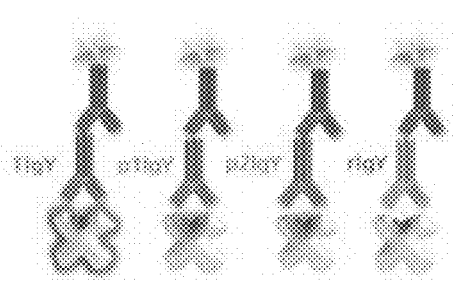
FIG. 9A is a schematic representation of an indirect enzyme-linked immunosorbent assay (ELISA) set-up of precipitation-purified IgY against whole enzyme TEM-1 (TIgY), an IgY against Peptide 1 (p1IgY), an IgY against Peptide 2 (p2IgY) and random non-specific IgY (rIgY) binding specificity to a beta-lactamase TEM-1 protein. Anti-chicken IgG conjugated with horse radish peroxidase were used as secondary antibody.

Example 4. Binding Activity of TIgY, p1IgY, p2IgY and rIgY to Beta-Lactamase TEM-1 Protein To determine the specific activity of TIgY, p1IgY, and p2IgY against beta-lactamase TEM protein and to determine which peptide targeting IgY (p1IgY or p2IgY) bound better to the TEM-1 active site, an indirect ELISA assay was performed as shown in FIG. 9A. Briefly, a 96-well plate was coated with 100 µl of 1 µg/ml beta-lactamase TEM protein diluted in coating buffer carbonate-bicarbonate buffer (prepared according to manufacturer, pH 9,6, BUF030A, Bio-Rad AbD Serotec GmbH, Puchheim, Germany) and was incubated overnight at 4° C. The plate was washed three times with washing buffer (PBS buffer containing 0.05% (vol/vol) Tween®-20 (P9416, Sigma Aldrich Chemie GmbH, Taufkirchen, Germany) and was blocked for 2 hours at room temperature with 200 µl of blocking buffer-PBS buffer containing 0.05% (vol/vol) Tween®-20 and 2% (w/vol) non-fat milk powder (T145.2, Carl Roth, Germany). The plate was then washed three times with washing buffer.

Next, specific IgYs (TIgY, p1IgY, p2IgY) and non-specific rIVIgY were diluted to 200 µg/ml with diluent buffer-PBS buffer containing 0.05% (vol/vol) Tween®-20 and 0.3% (w/vol) non-fat milk powder, and were loaded by multichannel pipette with three technical replicates per sample on the 96 well plate in serial 2-fold dilutions, and mixed 10 times. The plate was then incubated for 2 hours at room temperature and washed again three times with washing buffer. 100 µl of secondary antibody anti-chicken IgY Rabbit IgG with horse radish peroxidase conjugate (SA1-9509, Thermo Fisher) diluted 1:5000 (vol/vol) with diluent buffer and was added to each well and incubated for 1 hour at 37° C.

The plate was washed again three times with washing buffer, then 100 µl of the substrate solution TMB Core+ (BUF062a, Bio-Rad AbD Serotec GmbH, Puchheim, Germany) for HRP-conjugated antibodies was added to each well and incubated for 10 minutes at room temperature in the dark. The reaction was stopped by adding 50 µl of 0.2M Sulfuric acid (diluted with MiliQ, 1,09072.1000, Sigma-Aldrich, Taufkirchen, Germany) to each well and absorbance of samples was measured at 450 nm. ELISA assay was repeated three times (n=3) and values were plotted.

Figure 9B:
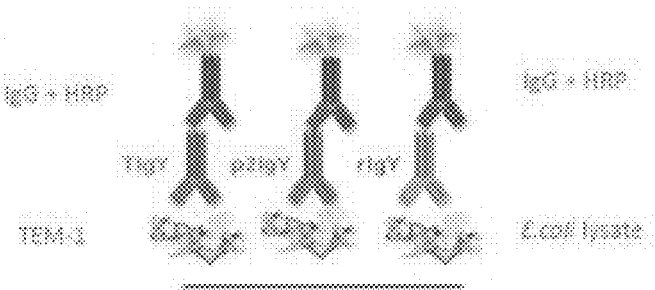
FIG. 9B is a schematic representation of an indirect enzyme-linked immunosorbent assay (ELISA) set-up of TIgY, p2IgY and rIgY binding specificity to TEM-1 in $E.$ $coli$ cell lysate. Anti-chicken IgG conjugated with horseradish peroxidase were used as secondary antibody.

IgYs against TEM-1 beta lactamase p1IgY, p2IgY and TIgY were purified by precipitation, which is the fastest and cheapest method for obtaining high amounts of IgYs (Schade et al., *Altern. Lab. Anim.* 2005, 33:129-154). These IgYs were analyzed via indirect ELISA using a twofold dilution series starting from a concentration of 200 µg/ml, to determine their binding activity against the beta-lactamase TEM protein (purified TEM-1), and to determine their activity against TEM-1-producing *E. coli* lysate (FIGS. 9A and 9B).

Figure 10A:
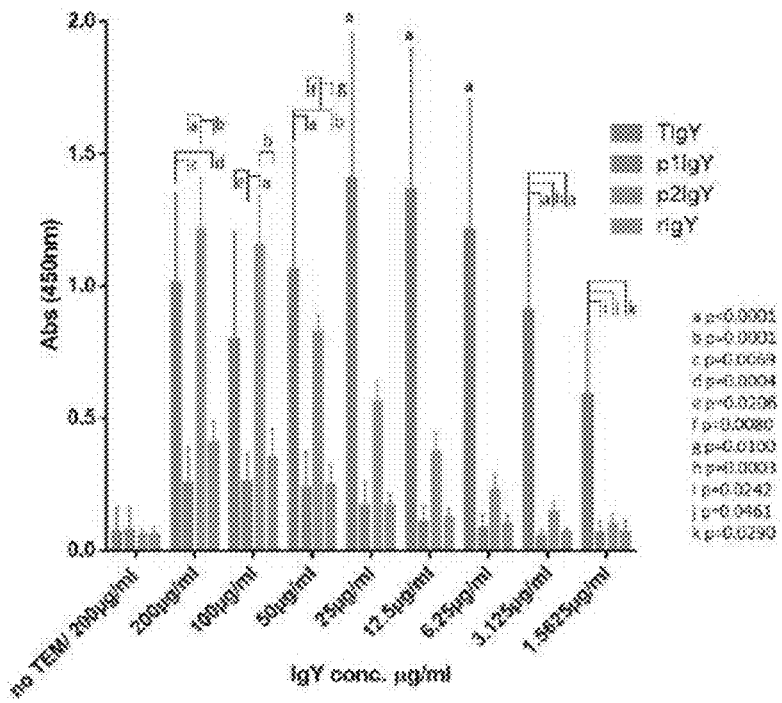
FIG. 10A is a bar graph showing binding activity of precipitation-purified IgYs against TEM-1 (TIgY, p1IgY, p2IgY and rIgY) (n=3, performed in triplicate) a, p<0.0001; b, p=0.0001; c, p=0.0069; d, p=0.0004; e, p=0.0206; f, p=0.0080; g, p=0.0100; h, p=0.0003; I, p=0.0242; j, p=0.0461; k, p=0.0290
Figure 10B:
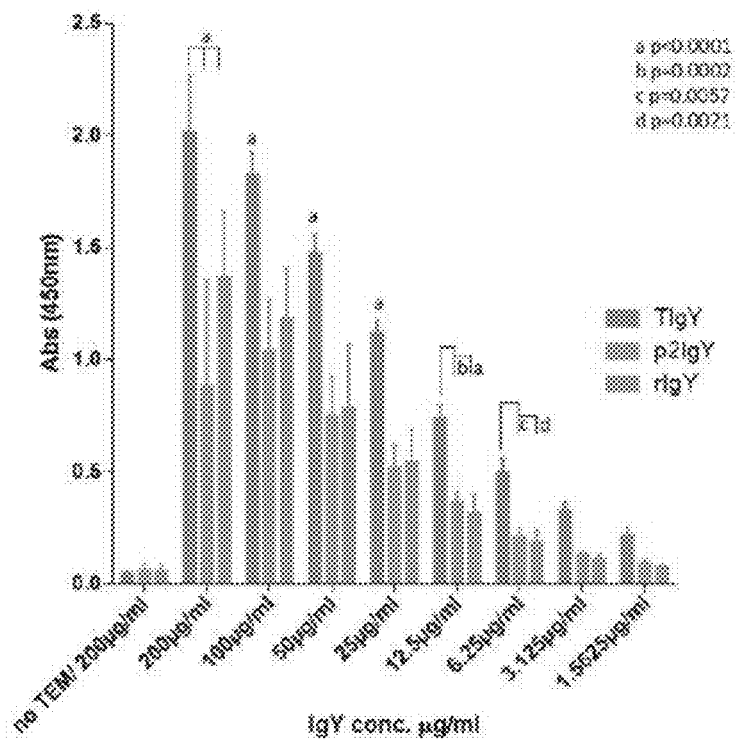
FIG. 10B is a bar graph showing binding activity of precipitation-purified IgYs against cell lysate of TEM-1 producing $E.$ $coli$ (TIgY, p2IgY and rIgY) (n=2, performed in duplicate)

As shown in FIG. 10A, at concentrations of 50-200 µg/ml, the ELISA results revealed a better binding ability of p2IgY and TIgY to purified TEM-1 as compared to p1IgY and rIgY (a negative control)(<0.05). At concentrations less than 50 µg/ml, TIgY showed the best binding capacity to purified TEM-1 amongst all tested antibody types (FIG. 10B). A signal for TIgY was detected even at a concentration as low as 1.56 µg/ml. p1IgY was not able to bind to TEM-1. rIgY showed no non-specific binding. p1IgY was excluded from further experiments in this study because it did not show improved binding as compared to the negative control. However, it is believed that p1IgY did not bind to TEM-1 in this particular study, because of steric hindrances surrounding the H2 helix, which made peptide 1 inaccessible for the specific p1IgY. We believe that appropriate conjugation of Peptide 1 (e.g., by KLH) would most likely allow Peptide 1 to reach the active site and potentially result in inactivation.

Taken together, ELISA tests revealed that among the precipitation-purified short peptides based IgYs, only p2IgY had a binding activity towards the active site of beta-lactamase TEM protein. Moreover, TIgY showed the highest binding activity towards beta-lactamase TEM protein among all precipitation-purified IgYs.

After the first selection of IgYs to recombinant beta-lactamase TEM protein, the next step was to determine the specific activity of TIgY and p2IgY against TEM-1 beta-lactamase produced by *E. coli* in cell culture. An indirect ELISA assay was performed using *E. coli* cell lysate as shown in FIG. 9B.

To prepare *E. coli* cell lysates, aliquots of cell suspension were sonicated on ice after two cycles at 1 minute, applying 70% of power. Cell lysates were diluted with coating buffer 1:32 (vol:vol), which corresponded to ~1.2×10$^6$ CFU/ml, and used to coat a 96-well plate, by loading 100 µl per well. The plate was then incubated overnight at 4° C. Plate was washed three times with washing buffer and blocked for 2 hours at room temperature with 200 µl of blocking buffer. Next, the plate was washed again three times with washing buffer. Specific IgYs (TIgY and p2IgY) and non-specific rIVIgY were diluted to 200 µg/ml with diluent buffer. The ELISA assay was repeated two times (n=2) and values were plotted.

The results of the TEM-1-producing *E. coli* cell lysate ELISA showed that TIgY had the highest binding activity to TEM-1 present in the lysate (FIG. 10B). It was detected starting form the highest concentration of 200 µg/ml until the concentration 6.25 µg/ml (p<0.05). The reason why p2IgY binding was not detected in this set up might be that the concentration of TEM-1 secreted by *E. coli* was much lower than the concentration of purified TEM-1 applied in the previous setting (1 µg/ml). No significant difference was showed between values for p2IgY and rIgY.

Example 5. In Vitro Combination Treatment of Antibiotics and IgYs Against TEM-1 Beta-Lactamase Reduces the Growth of TEM-1 Producing E. coli In this study, the IgYs described herein were used to determine whether TEM-1 beta-lactamase inactivation would sensitize ampicillin-resistant TEM-1-producing bacteria (e.g., TEM-1 producing E. coli) to ampicillin, and facilitate bacterial cell death.

The experiments described herein use a strain of the TEM-1 expressing E. coli BW25113 ΔbamBΔtolC where TEM-1 gene was integrated behind the bla promoter. Bacteria were cultured in Luria Bertani Broth (LB) medium (28713, Sigma Aldrich Chemie GmbH, Taufkirchen, Germany) with 0.1 mg/ml ampicillin (11593027, Life Technologies GmbH, Darmstadt, Germany) for 18 h, at 37° C. and with 150 rpm. Streak plates were prepared by spreading the bacteria on LB-agar plate (19344, Sigma Aldrich Chemie GmbH) containing 0.1 mg/ml ampicillin by sterile loop. Plates were incubated for 16 h, at 37° C. and then kept at 4° C. A single colony was picked to inoculate 5 ml of LB medium (with 0.1 mg/ml ampicillin). The inoculation was incubated overnight on a shaker (37° C., 150 rpm), transferred to a sterile conical flask containing 200 ml of LB medium pre-warmed to 37° C. (with 0.1 mg/ml ampicillin) and kept on a shaker until bacteria reached OD600 ~0.4. Glycerol stocks were prepared by mixing liquid bacteria culture 1:1 (vol/vol) with 50% Glycerol (G5516, Sigma Aldrich Chemie GmbH, Taufkirchen, Germany) solution diluted with MiliQ water, and kept at −80° C. The quantitative analysis of E. coli was done using a spread-plate method and establishing a bacterial growth curve.

E. coli cell suspension was adjusted to OD600 0.05 corresponding to a cell density of $2 \times 10^6$ cfu/ml. Specific IgYs solutions: p2IgY and TIgY were diluted with LB medium containing 0.1 mg/ml ampicillin, to 10 mg/ml. As a negative control, a non-specific 10 mg/ml rIIgY solution was used, and LB medium with 0.1 mg/ml ampicillin without IgY was used as a blank. All the IgY solutions were mechanically sterilized using 0.22-µm membrane syringe filters. Each IgY solution and control were mixed 1:1 with a prepared E. coli suspension. Mixtures were incubated for 24 hours at 37° C. and 150 rpm. At the time points 0 hour, 3 hours, 6 hours and 24 hours of incubation OD600 values of each mixture were measured, aliquots were taken and drop plates were prepared (n=6) as previously described. Colony-forming units for each sample at all incubation time points were counted, total number of bacteria colony-forming units per ml for each incubation time point was calculated and plotted.

To detect TEM-1 in E. coli cell cultures, E. coli was transferred into tubes and kept on ice. Half of the samples were sonicated (2× cycles, 1 min, power 70%), while the other half was left untreated. Next, the treated and untreated bacteria culture samples were diluted 1:2.5 (vol/vol) with PBS (P4417, Sigma Aldrich GmbH, Taufkirchen, Germany) transferred in triplicates to 96 well plate and mixed 8:1 (vol/vol) with 0.5 mg/ml Nitrocefin (2388-5, BioVision Inc. Milpitas, CA, USA) dissolved before in 0,1M PBS and DMSO (D4540, Sigma Aldrich GmbH, Taufkirchen, Germany) 200:1 (vol/vol). As controls, LB medium with 0.1 mg/ml ampicillin and PBS were used, also mixed with Nitrocefin solution. Samples were incubated in room temperature for 30 minutes, then photographed and measured for absorption in a plate reader at 486 nm.

The inhibition assay where a TEM-1-producing E. coli liquid cell culture was incubated for 24 hours with 5 mg/ml of p2IgY, TIgY and rIgY, in LB medium in the presence of ampicillin revealed that all of IgYs showed an inhibitory effect on the growth of TEM-1-producing E. coli. Other studies described specific precipitation-purified IgYs used in vitro in a range of 1-10 mg/ml against different pathogens and a decreased growth of bacteria was observed even after the treatment with unspecific IgYs (Sugita-Konishi et al. Biosci. Biotechnol. Biochem. 1996, 60:886-888; Tobias et al., Brazilian J. Microbiol. 2012, 43:544-551; and Shin et al., Clin. Diagn. Lab Immunol. 2002, 9:1061-1066). It might be due to the purification method: in a non-affinity purified population of IgYs, even up to ~98% of IgYs might be unspecific and it can increase over 99% when the chicken was immunized with a short peptide conjugated to KLH.

Example 6. Binding Activity of Affinity Purified IgYs Against TEM-1

To increase the specificity of IgYs to the TEM-1 beta-lactamase and to decrease the high unspecific binding, IgYs targeting Peptide 2 of the TEM-1 active site and targeting the whole enzyme TEM-1 were affinity purified, named ap2IgY and aTIgy, respectively.

Figure 11:
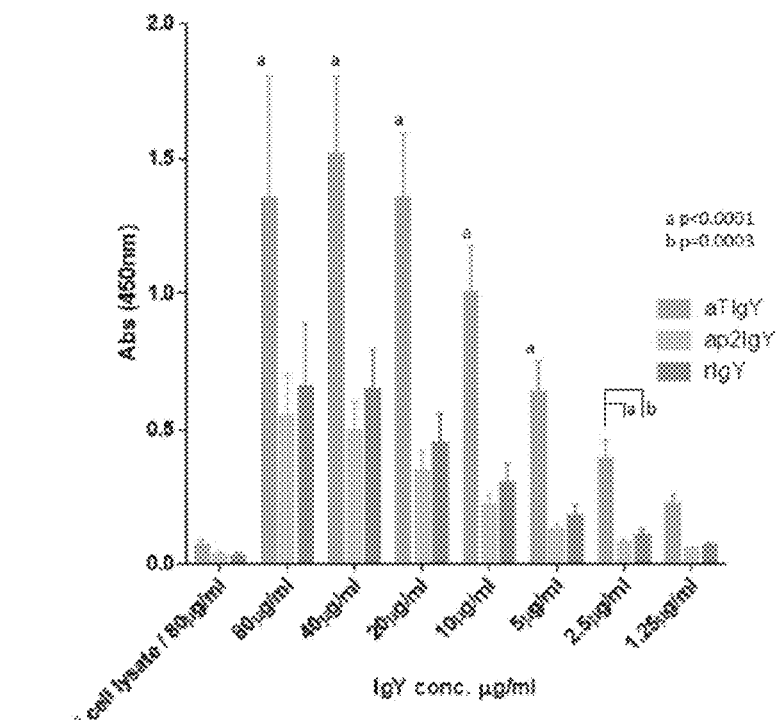
FIG. 11 is a bar graph showing binding activity of precipitation-purified IgYs against TEM/1-1 (aTIgY, ap2IgY and rIgY) against the lysate of TEM-1 producing K coil (n=3, performed in triplicate) a, p<0.0001; b, p=0.0003

In a two-fold dilution series ELISA of the cell lysate of TEM-1-producing E. coli, starting from 80 µg/ml as the highest concentration, among ap2IgY, rIgY and aTIgY, aTIgY showed the highest binding activity to TEM-1, ($p<0.05$) (FIG. 11). The data using aTIgY was similar to the data using precipitation-purified TIgY. aTIgY showed binding specificity at a concentration of 2.5 µg/ml, while TIgY showed binding signal at the minimal concentration of 6.25 µg/ml.

Figure 9C:
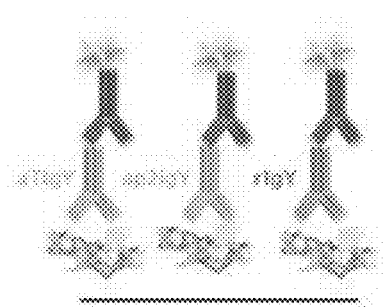
FIG. 9C is a schematic representation of an indirect enzyme-linked immunosorbent assay (ELISA) set-up of affinity-purified IgY against whole enzyme TEM-1 (aTIgY), affinity-purified IgY against Peptide 2 (ap2IgY) and affinity-purified random IgY (arIgY) binding specificity to TEM-1 in $E.$ $coli$ cell lysate. Anti-chicken IgG conjugated with horseradish peroxidase were used as secondary antibody.

To determine the specific activity of affinity-purified aTIgY and ap2IgY against beta-lactamase TEM-1 produced by E. coli in a cell culture, an indirect ELISA assay was performed using E. coli cell lysate as shown in FIG. 9C. To prepare E. coli cell lysate, aliquots of cell suspension were sonicated on ice in two cycles, for 1 minute, applying 70% of power. The cell lysate was diluted with coating buffer 1:25 (vol:vol), which corresponded to ~$1.5 \times 10^6$ CFU/ml, and was used to coat the 96 well plate, by loading 100 µl per well. The plate was then incubated overnight at 4° C.

The plate was washed three times with washing buffer and blocked for 2 hours at room temperature with 200 µl of blocking buffer. Next, the plate was washed again three times with washing buffer. Specific IgYs (TIgY and p2IgY) and non-specific rIIIIgY were diluted to 80 µg/ml with diluent buffer. ELISA assay was repeated three times (n=3) and values were plotted.

ELISA tests using TEM-1-producing E. coli lysates, only TIgY and affinity-purified aTIgY showed binding activity compared to the other IgYs in their respective groups. Interestingly, not only TIgY (against TEM-1), but also p2IgY (against Peptide 2) showed an inhibitory effect on the growth of TEM-1-producing E. coli in vitro in the presence of ampicillin. Similar results were obtained with their affinity-purified counterparts (aTIgY and ap2IgY), however, using only a fraction of the concentration (5 mg/mL vs 0.1 mg/mL). These results suggested that ap2IgY and aTIgY inactivate the TEM-1 by targeting the active site and building an antibody coat around the enzyme, respectively, and thereby preserve the antimicrobial activity of ampicillin. In addition, these results indicated that the Ω-loop is potentially a good target for IgYs against TEM-1.

Example 7. IgYs Against β-Lactamase TEM-1-Producing *E. coli* Cells Used as Alternative to Antibiotic Treatment Reduced the Growth of *E. coli* In Vitro The aim of this strategy was to target and inhibit the growth of TEM-1-producing *E. coli* by specific IgYs developed against their cell surface in the absence of an antibiotic. Several studies reported positive results in the treatment against bacteria with specific IgYs obtained after immunizing chickens with inactivated bacterial cells (Song et al., J. Food Saf. 2009, 29:511-520; Tobias et al., Brazilian J. Microbiol. 2012, 43:544-551; Sunwoo et al., Open Immol. J. 2010, 3:1-8; and Guimaries et al., Arch. Immunol. Ther. Exp. (Warsz) 2009, 57:377-382). IgYs produced by this method showed not only bacteria growth inhibitory potential but also prevented bacterial colonization by inhibiting their adhesion to epithelium cells (Chalghoumi et al., Foodborne Pathog. Dis. 2009, 6:593-604).

To obtain highly specific IgYs towards the TEM-1-producing *E. coli* cell surface, two types of *E. coli* inactivation methods for IgY development were assessed. Heat-inactivation is an effective method of killing bacteria and the temperature used ranges between 6° and 80° C. The high temperature causes denaturation of cellular components, such as DNA and ribosomes, and melts membrane lipids, which results in death of bacteria. Some studies suggest heat-inactivation might negatively influence the preservation of antigens on the cell surface (Lee et al., Appl. Environ. Microbiol. 2002, 68:5379-5386; and Macke et al., J. Gen. Microbiol. 1991, 137:2361-2374).

Electron beam irradiation (E-beam) is based on low energy electron irradiation (LEEI) and is a new method of inactivating pathogens. Since E-beam preserves cell integrity and antigenic structures, it has a big potential in vaccine development (Fertey et al., Viruses 2016, 8). eIgY and hIgY were developed by immunization of chickens with either e-beam-inactivated or heat-treated (65° C.) whole cells of TEM-1 producing *E. coli*, respectively. Both types of antibodies were affinity-purified. To the best of the present inventors knowledge this is the first study using E-beam for whole bacterial cell antigens preparation for the development of specific IgYs.

E-beam inactivation of E. cob samples was performed as described by Fertey et al. using ionizing radiation dose of 5kGy (EBLab 200, Comet, Flamatt, Switzerland) (Fertey et al., Viruses 2016, 8). For the heat inactivation, bacteria suspensions were incubated for 1 hour at 65° C. Viability tests were performed by applying inactivated samples and control sample (untreated) on LB agar plates, subsequently incubated overnight at 37° C. To fix and preserve cell membrane structures for subsequent immunization procedures, the heat and e-beam inactivated samples were treated with the Membrane Structure Conservation kit (K105, Davids Biotechnologie GmbH, Regensburg, Germany) according to manufacturer's instruction. Each sample with different whole bacteria cell antigens contained ~8×10⁸ CFU.

*E. coli* cell suspension was adjusted to OD600 0.05 corresponding to a cell density of $2\times10^6$ cfu/ml. Specific IgYs solutions: h2IgY and eTIgY were diluted with LB medium without ampicillin, to 0.2 mg/ml. As a negative control a non-specific 0.2 mg/ml rIVIgY solution was used, and LB medium without ampicillin and without IgY was used as a blank. All IgY solutions were mechanically sterilized using 0.22-μm membrane syringe filters. Each IgY solution and control were mixed 1:1 (vol/vol) with prepared *E. coli* suspension. Mixtures were incubated for 24 hours at 37° C. and 150 rpm. At the time points 0 hour, 3 hours, 6 hours and 24 hours of incubation OD600 values of each mixture were measured, aliquots were taken and drop plates were prepared (n=3) as previously described. Colony-forming units for each sample at all incubation time points were counted, total number of bacteria colony-forming units per ml for each incubation time point was calculated and plotted.

To generate affinity-purified IgY against heat-inactivated TEM-1 producing *E. coli* (hTIgY), affinity-purified IgY against e-beam-inactivated TEM-1 producing *E. coli* (eIgY), immunization and affinity purification of eIgY and hTIgY was performed using standard techniques. Chickens were immunized separately with prepared whole bacterial cell antigens: *E. coli* inactivated by e-beam and heat in 42-week-long intervals. Eggs were collected 10-15 days after the last immunization. The egg yolk was then separated, IgYs were precipitated and specific IgYs were affinity purified using the antigen immobilized on the resin (each type of inactivated bacteria cells). IgY fractions were diluted with PBS containing 0.02% sodium azide to the final concentration of: eIgY (0.51 mg/ml) and hIgY (0.48 mg/ml).

After inactivation of TEM-1-producing *E. coli* by E-beam at 5kGy or heat-inactivation at 65° C. for 1 hour, cells were tested for viability and compared with a positive control (TEM-1-producing *E. coli* cultivated in LB). Both inactivation methods were successful and no bacteria cell growth was observed, opposite to the positive control (data not shown).

Figure 9D:
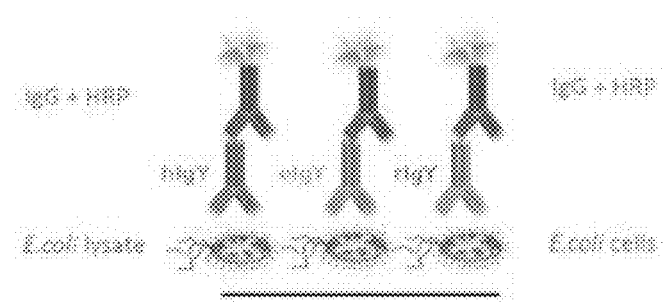
FIG. 9D is a schematic representation of an indirect enzyme-linked immunosorbent assay (ELISA) set-up of affinity-purified IgY against heat-inactivated TEM-1 producing $E.$ $coli$ (hTIgY), affinity-purified IgY against e-beam-inactivated TEM-1 producing $E.$ $coli$ (eIgY), and rIgY binding specificity to bacteria cell surface of $E.$ $coli$. Anti-chicken IgG conjugated with horseradish peroxidase were used as secondary antibody.

To determine the specific activity of affinity-purified IgYs against heat-inactivated and e-beam TEM-1 producing *E. coli*, such as hIgY and eIgY respectively, an indirect bacterial ELISA assay was performed as shown in FIG. 9D. *E. coli* cells were harvested by centrifugation at 4° C., for 10 minutes, at 4000 g, washed twice with 1×PBS and incubated in 4% (vol/vol) formaldehyde in 1×PBS at room temperature for 20 minutes. Next, the cells were washed three times with PBS. Thereafter, *E. coli* cells were diluted with coating buffer 1:25 (vol:vol) to ~$1.5\times10^6$ CFU/ml, and suspension was used to coat a 96 well plate, loaded 100 μl per well. The plate was incubated overnight at 4° C.

As the next step, the plate was washed three times with washing buffer and blocked for 2 hours at room temperature with 200 μl of blocking buffer. Then, the plate was washed three times with washing buffer. Specific IgYs (hIgY and eIgY) and non-specific rIIIIgY were diluted to 80 μg/ml with diluent buffer. ELISA assay was repeated three times (n=3) and values were plotted.

Figure 12:
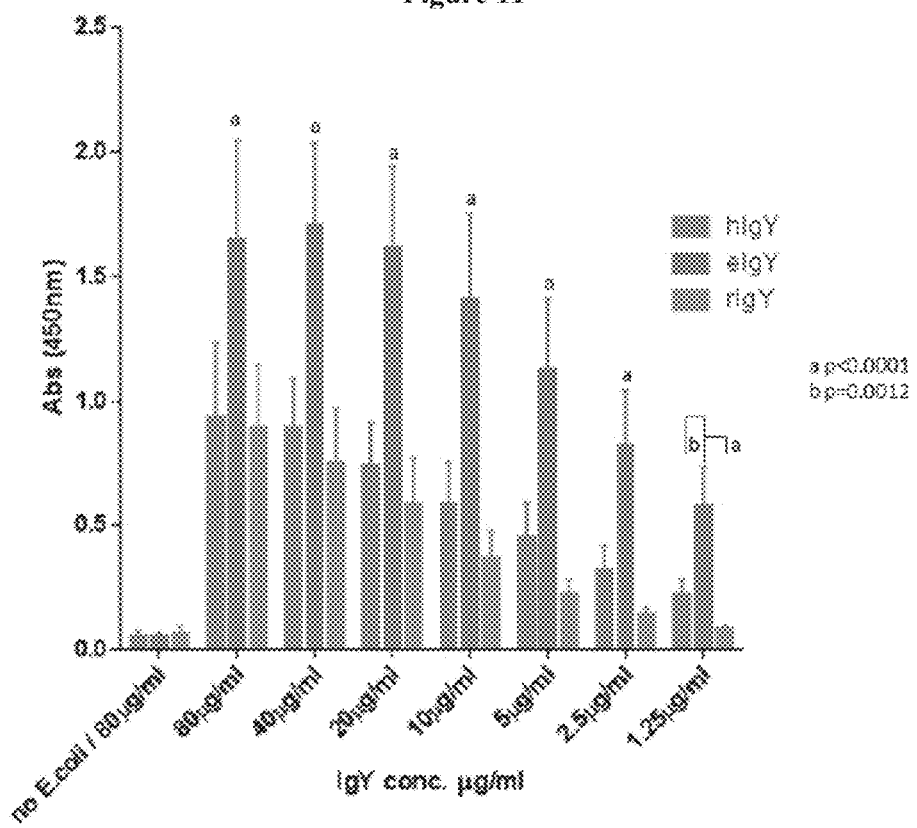
FIG. 12 is a bar graph showing binding activity of affinity-purified IgYs against TEM-1 producing $E.$ $coli$ cells (n=3) a, p<0.0001; b, p=0.0012

The results of ELISA against TEM-1-producing *E. coli* fixed by 4% formaldehyde solution, revealed that eIgY bound better to *E. coli* cells than hIgY and rIgY (used as a negative control) (FIG. 12). In the two-fold dilution series using 80 μg/ml as the highest IgY concentration, eIgY showed binding specificity as low as 1.25 μg/ml and significantly differed from ap2IgY and rIgY ($p<0.05$). No significant difference was observed between values obtained with hIgY and rIgY.

These results suggested that eIgYs more specifically recognized TEM-1-producing *E. coli* cells because E-beam-inactivation preserved cell integrity and antigenic epitopes better than heat-inactivation, which more likely disrupted the cell integrity and generated IgYs specific not only to the cell surface but also to cellular content.

Example 8. In Vitro Growth Inhibition of TEM-1 Producing *E. coli* by Affinity-Purified IgYs Specific to *E. coli*

Figure 13:
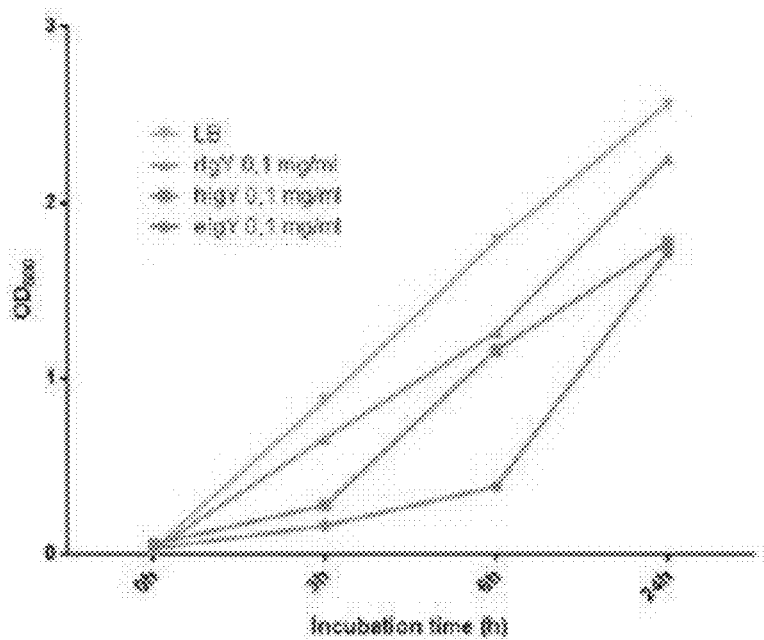
FIG. 13 is a graph showing growth of TEM-1-producing $E.$ $coli$ over 24 hours following incubation with affinity-purified IgYs against TEM-1 (rIgY, hIgY and eIgY) mixed with 0.1 mg/mL ampicillin. (n=1).

In the inhibition assay, TEM-1-producing *E. coli* liquid cell cultures were incubated for 24 h with 0.1 mg/ml of either eIgY, hIgY or rIgY, diluted in LB medium without ampicillin (FIG. 13). In contrast to the ELISA results, both eIgY and hIgY inhibited the growth of TEM-1-producing *E. coli* in vitro. LB and rIgY treatment did not inhibit the growth of TEM-1-producing *E. coli* in vitro.

Figure 14A:
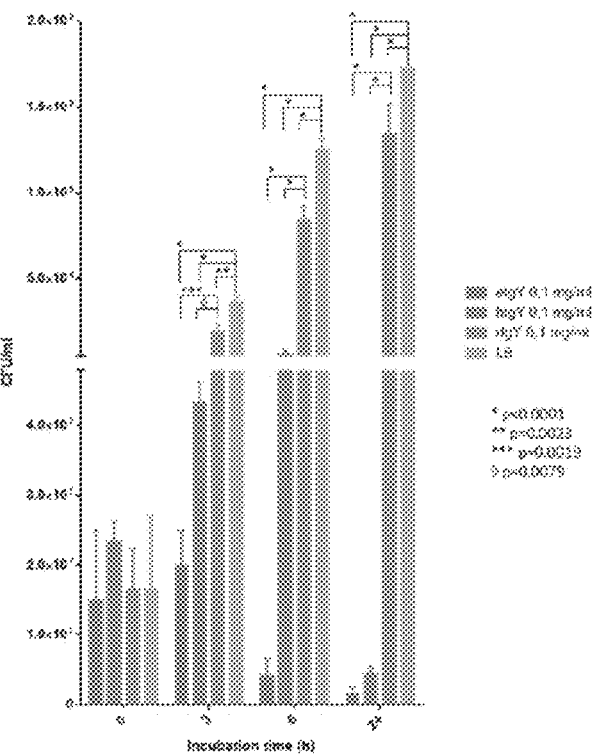
FIG. 14A is a bar graph showing the inhibitory effect of affinity-purified IgYs (eTIgY, hIgY, and rIgY) on the number of TEM-1-producing $E.$ $coli$ colony forming units over 24 hours. *, p<0.0001; , p=0.0023; *, p=0.0019; diamond, p=0.0079
Figure 14B:
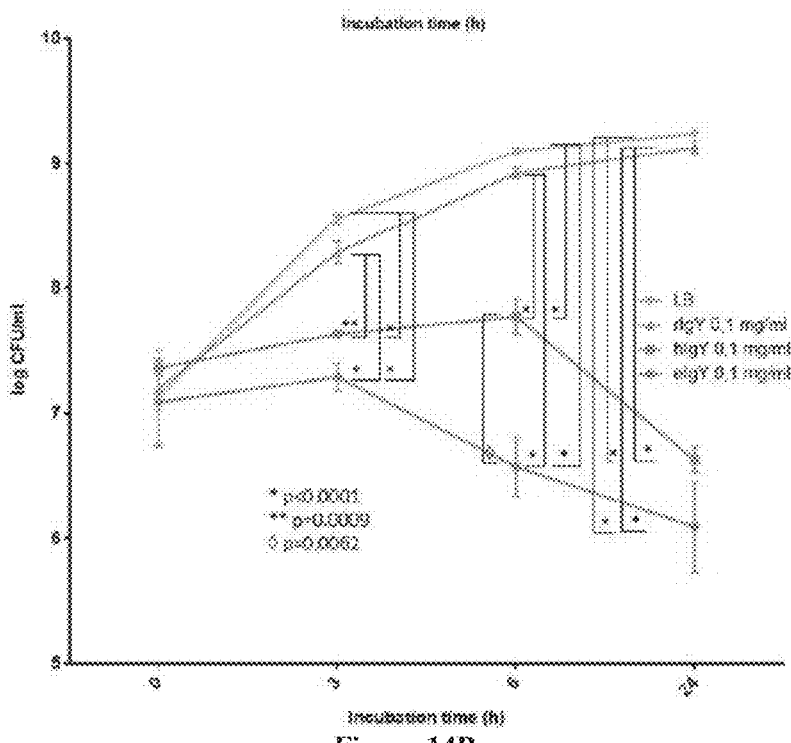
FIG. 14B is a growth curve of TEM-1 producing $E.$ $coli$ following incubation with 0.1 ng/mL rIgY, 0.1 mg/mL hIgY, 0.1 mg/mL eIgY, or LB-1-amp. 1 diamond, p=0.0009; 2 diamonds, p=0.00114; **, p=0.0327; *, p<0.0001

The data in FIG. 13 showed that *E. coli* density grew for all of tested samples. The bacteria cell count revealed that treatment with eIgY and hIgY significantly decreased the number of CFU/ml in samples treated with TEM-1-producing *E. coli* ($p<0.05$), while treatment with rIgY and LB did not (FIG. 14A). The growth curves with logarithmic values of TEM-1-producing *E. coli* showed a steady decline 6 hours after treatment with eIgY or hIgY. Both were significantly different from those after treatment with rIgY and LB ($p<0.05$) (FIG. 14B). These results indicated that specific and affinity-purified eIgY and hIgY developed against the surface of TEM-1-producing *E. coli* cell showed inhibitory effect on TEM-1-producing *E. coli* in vitro at concentrations as low as 0.1 mg/ml. These results were comparable to a study of Sunwoo et al., *Open Immunol. J.* 2010, 3:1-8, where specific IgYs were developed against ETEC 987P *E. coli* cell lysate, and not inactivated whole bacteria cell antigen. Although the mechanism of growth inhibition of bacteria by eIgY and hTIgY was not conclusively determined, that the data presented herein suggested that by targeting and adhering to the surface of *E. coli*, eIgY and hTIgY blocked biological functions of bacteria, overlapped surface virulence factors and blocked the signaling between cells.

Although only eIgY showed binding activity compared to controls in ELISA tests, both affinity-purified eIgY (e-beam) and hIgY (heat treatment) showed reactivity towards TEM-1-producing *E. coli* in the immunofluorescence assay (data not shown) and inhibited bacterial growth without the presence of ampicillin in vitro. The data suggested that IgYs developed against the bacterial cell surface, target bacterial cells by building an antibody coat around them and, thereby, inhibit their biological functions.

Example 9. In Vitro Growth Inhibition of TEM-Producing *E. coli* by Affinity- and Precipitation-Purified IgYs in the Presence of Ampicillin To investigate the influence of developed IgYs on growth of TEM-1 producing *E. coli*, an inhibition assay was performed, in which *E. coli* inoculates, were incubated for 24 hours in the presence of p2IgY, TIgY, ap2IgY, aTIgY, hIgY, and eIgY. As controls LB medium (no IgY) and non-specific IgYs were used (rIIgY or rIIIgY). To compare the growth of *E. coli* after incubation with different IgYs, the drop plate method for colony counting was used (adapted and modified from Chen et al., *J. Microbiol. Methods* 2003, 55:475-479).

From each mixture 3×200 µl of aliquots was taken using multichannel pipette to prepare drop plates (Agar+0.1 mg/ml ampicillin) at the time points of incubation: 0 hour, 3 hours, 6 hours and 24 hours. The 10-fold serial dilutions ($100-10^6$) were made by transferring by multichannel pipette 20 µl of mixtures to a well containing 180 µl of LB medium with 0.1 mg/ml ampicillin, and mixing 10 times. Three replicates of 20 µl from each of selected dilutions were plated onto agar plates. Plates with samples from each time point were first incubated for 3 hours at room temperature and then incubated for 16 hours at 37° C.

Colony-forming units were counted to calculate the total number of bacteria colony-forming units per ml of sample for each incubation time point and then were plotted. The growth of bacterial cells in mixtures was also monitored by bacterial density measurements at OD600 at each incubation time point and optically through visual changes.

Figure 15:
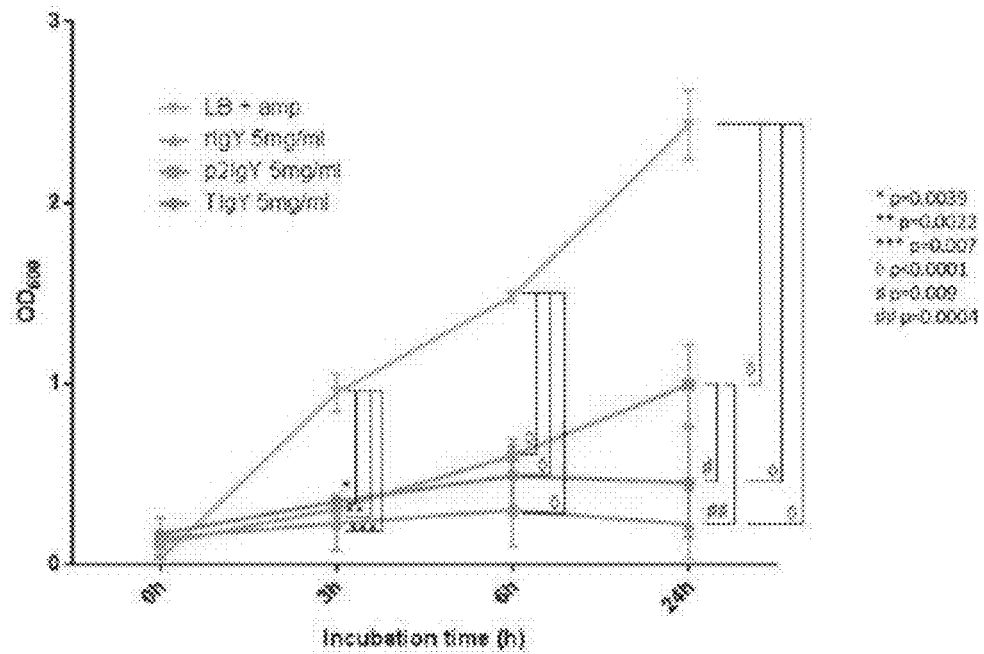
FIG. 15 is a graph showing growth of TEM-1-producing $E.$ $coli$ over 24 hours following incubation with 5 mg/mL rIgY, 5 mg/mL p2IgY, 5 mg/mL TIgY, or LB+ampicillin (LB+amp) *, p=0.039; , p=0.0022; , p=0.007; diamond, p<0.0001; #, p=0.09; ##4, p=0.0004.
Figure 16A:
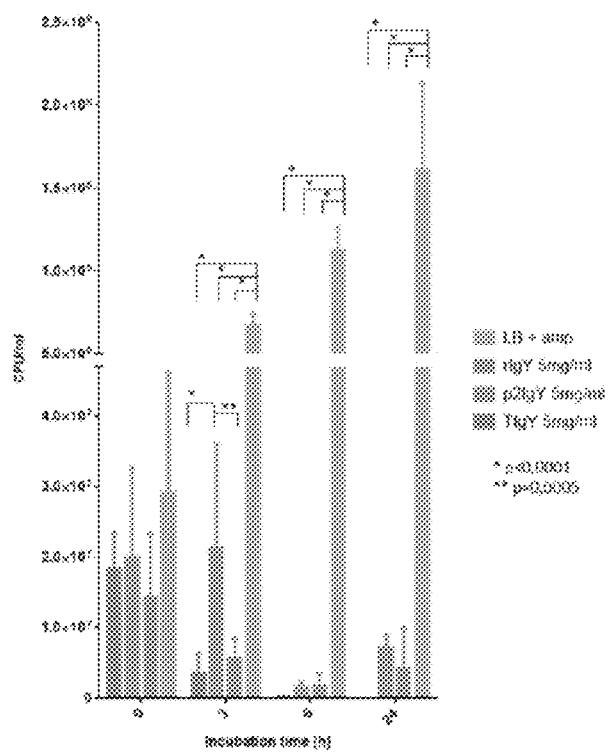
FIG. 16A is a bar graph showing the influence of different treatments on the number of TEM-1-producing $E.$ $coli$ colony forming units following incubation with 5 mg/mL rIgY, 5 mg/mL p2IgY, 5 mg/mL TIgY, or LB+amp. *, $p<0.0001$; * $p=0.0005$

The OD600 measurements of *E. coli* liquid cultures with different treatments in the presence of ampicillin showed a significant decrease of bacteria cell density when incubated with TIgY, p2IgY and, interestingly, with rIgY, in comparison to sample without the treatment—LB medium+ampicillin ($p<0.05$) (FIG. 15). Moreover, the inhibitory effect of TIgY and rIgY was greater than the one of p2IgY after 24 h of incubation and the decrease in cell density was significantly higher ($p<0.05$). At every specified time point of incubation (0 h, 3, 6 h and 24 h), samples from each condition were drop-plated in serial dilutions in order to count the number of living bacteria as a colony-forming unit. The CFU/ml in each liquid culture samples was calculated after the treatment with TEM-1-specific IgYs and controls. Treatment with p2IgY, TIgY, rIgY in the presence of ampicillin inhibited significantly the growth of TEM-1 producing *E. coli* when compared to sample without any treatment (LB+ampicillin) ($p<0.05$) (FIG. 16A).

Figure 16B:
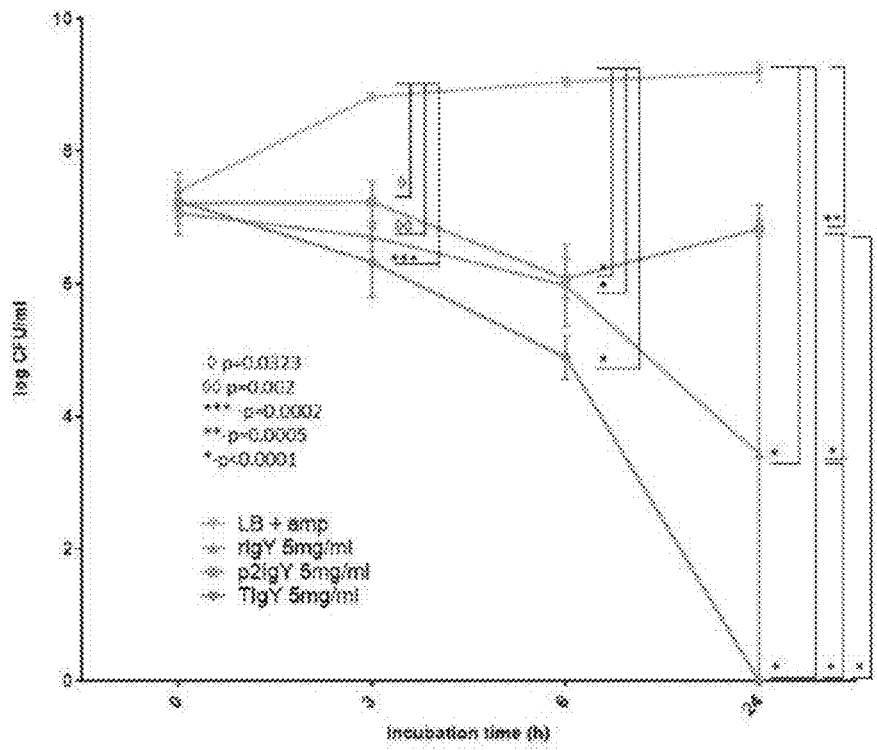
FIG. 16B is a growth curve of TEM-1 producing *E. coli* following incubation with 5 mg/mL rIgY, 5 mg/mi p2IgY, 5 mg/mL. TIgY, or LB+amp. 1 diamond, $p=0.0323$; 2 diamonds, $p=0.002$; *, $p=0.0002$; , $p=0.0005$; *, $p<0.0001$

Data were also plotted as logarithmic values to present how each of treatment influenced the grow curves of TEM-1-producing *E. coli* (FIG. 16B). The grow curve of *E. coli* incubated with TIgY dropped significantly in comparison to the rest of the samples. Treatment with rIgY decreased the growth of bacteria significantly. The data for p2IgY showed that the growth of *E. coli* was also inhibited, but not as strongly as in samples treated with either TIgY or rIgY.

To determine the effect of ap2IgY and TIgY on the growth of TEM-1-producing *E. coli*, *E. coli* cell suspension was adjusted to OD600 0.05 corresponding to a cell density of $2\times10^6$ cfu/ml. Specific IgYs solutions: ap2IgY and aTIgY were diluted with LB medium containing 0.1 mg/ml ampicillin, to 0.2 mg/ml. As a negative control a non-specific 0.2 mg/ml rIVIgY solution was used, and LB medium with 0.1 mg/ml ampicillin without IgY was used as a blank. All the IgY solutions were mechanically sterilized using 0.22-µm membrane syringe filters. Each IgY solution and control were mixed 1:1 (vol/vol) with prepared *E. coli* suspension. Mixtures were incubated for 24 hours at 37° C. and 150 rpm. At the time points 0 hour, 3 hours, 6 hours and 24 hours of incubation OD600 values of each mixture were measured, aliquots were taken and drop plates were prepared (n=3) as previously described. Colony-forming units for each sample at all incubation time points were counted, total number of bacteria colony-forming units per ml for each incubation time point was calculated and plotted.

Figure 17:
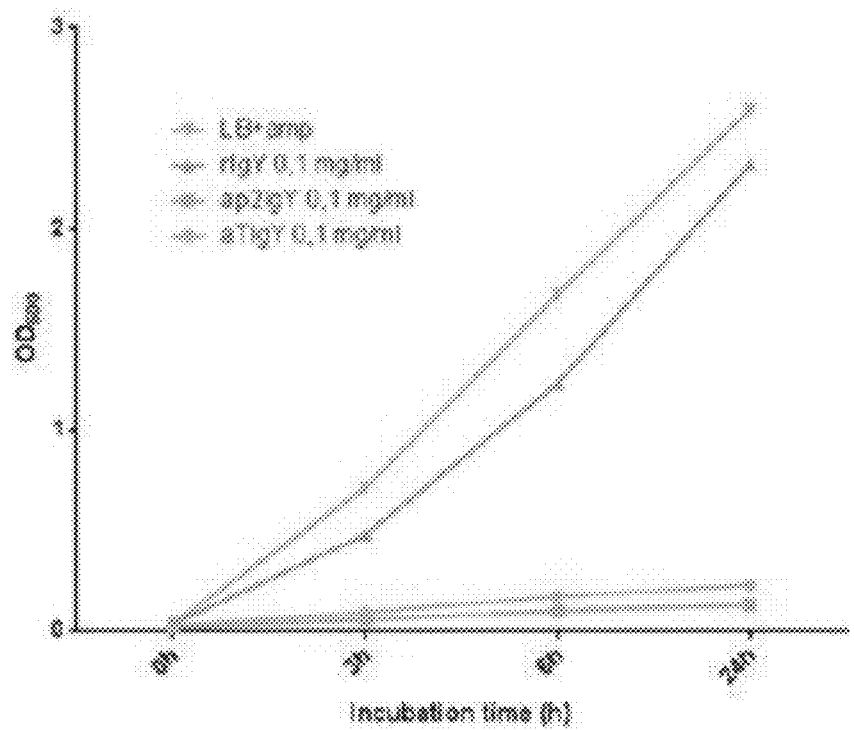
FIG. 17 is a graph showing growth of TEM-1-producing *E. coli* over 24 hours following incubation with affinity-purified IgYs against TEM-1 (rIgY, ap2IgY and aTIgY) mixed with 0.1 mg/mL ampicillin. (n=1)

An inhibition assay was performed by incubating TEM-producing *E. coli* liquid cell culture for 24 hours with 0.1 mg/ml of ap2IgY, aTIgY and rIgY in LB medium in the presence of ampicillin. ap2IgY and aTIgY inhibited the growth of TEM-1-producing *E. coli* in culture. A dramatic decrease of the *E. coli* cell density was observed after the ap2IgY and aTIgY treatment, while rIgY treatment had no effect on *E. coli* growth (FIG. 17).

Figure 18A:
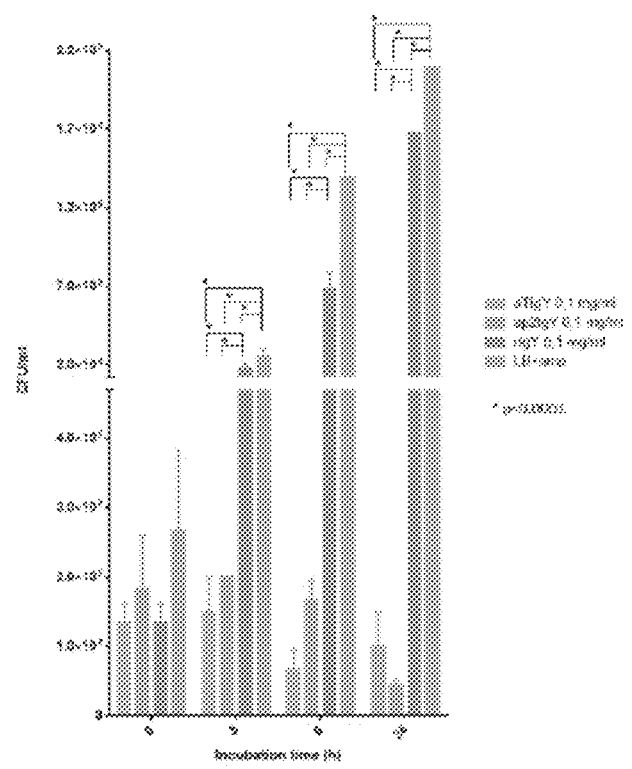
FIG. 18A is a bar graph showing the inhibitory effect of affinity-purified IgYs (aTIgY, ap2IgY, rIgY) on the number of TEM-1-producing *E. coli* colony forming units over 24 hours. *, $p<0.0001$
Figure 18B:
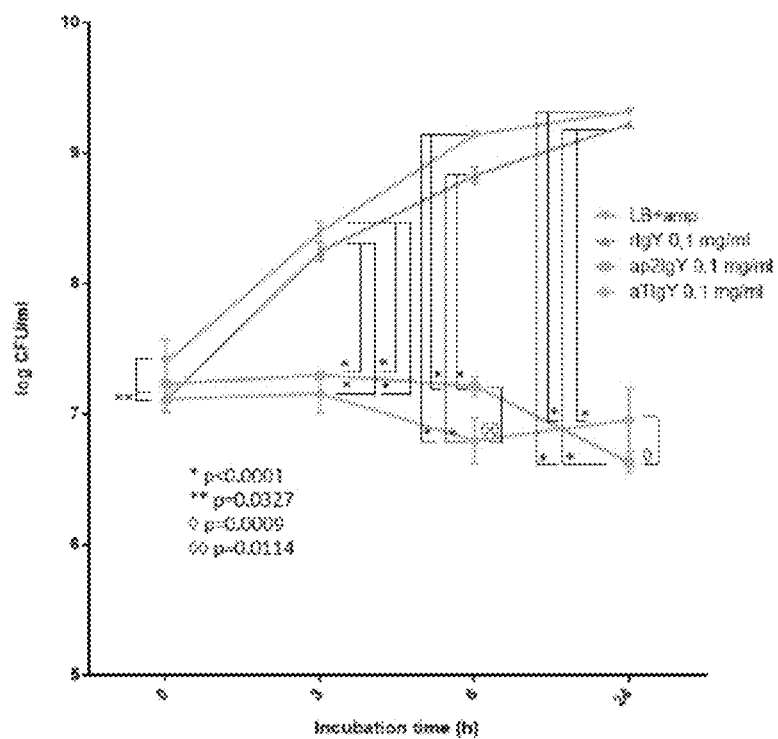
FIG. 18B is a growth curve of TEM-1 producing *E. coli* following incubation with 0.1 mg/mL rIgY, 0.1 mg/mL ap2IgY, 0.1 mg/mL aTIgY, or LB-+amp. 1 diamond, $p=0.0009$; 2 diamonds, $p=0.00114$; **, $p=0.0327$; *, $p<0.0001$

Treatment with ap2IgY and TIgY in the presence of ampicillin significantly decreased the number of CFU/ml in treated samples of TEM-1-producing *E. coli* cultures in comparison to rIgY and LB ($p<0.05$) (FIG. 18A). rIgY at the concentration of 0.1 mg/ml did not show non-specific inhibitory effect. The logarithmic values showed that the growth curves of TEM-1-producing *E. coli* treated with ap2IgY and aTIgY decreased and were significantly different from those representing treatment with rIgY or LB alone (p<0.05)(FIG. 18B). These results showed that affinity purified ap2 and aTIgY developed against TEM-1 at low concentrations such as 0.1 mg/ml, and in the presence of ampicillin showed inhibitory effect against TEM-1 producing *E. coli* strain in vitro. It might be that ap2IgY and aTIgY target the active site and coat the whole enzyme, respectively, and as a consequence inactivate the TEM-1 so the ampicillin can eradicate the *E. coli*. There are studies confirming neutralizing properties of specific IgYs against virulent proteins secreted by pathogens, e.g. Shiga toxin 2e produced by *E. coli* or Neurotoxin A produced by *C. botulinum* (Trott et al., *J. Food Prot.* 2009, 72: 1005-1011; and Arimitsu et al., *Microbiol. Immunol.* 2014, 58: 643-648). Additionally, Shin et al. reported development of an effective IgY inactivating a secreted-by-*H. pylori* Urease B, based on de novo synthesised short peptide representing the enzyme (Shin et al., *J. Med. Microbiol.* 2004,53:31-34).

All the data from Examples 1-9 are presented as mean values f SD. Statistical analysis for colorimetric detection of TEM-1 activity in *E. coli* culture was conducted using one-way ANOVA with Dunnett's multiple comparisons test. Statistical analysis of binding activity tests of IgYs via indirect ELISA were conducted using two-way ANOVA with Bonferroni's multiple comparisons tests. Statistical analysis of inhibition assays were conducted using two-way ANOVA with Tukey's multiple comparison tests.

Example 10. Treating Infections by Beta-Lactamase-Producing Bacteria with IgYs in Combination with Antibiotics in Humans To confirm the good inhibitory effect of TIgY, p2IgY, eIgY, and hIgY on TEM-1-producing *E. coli*, they are tested in animal infectious models to confirm their activity, either as a complementary or alternative therapy, to antibiotics. Such studies can be done using orally introduced specific antibodies, i.e., the IgYs described herein, against different bacteria in animal models, e.g., against *C. difficile* in hamster, *H. pylori* in mouse and *E. coli* in piglets (Malekshahi et al., *Microb. Pathog.* 2011, 51:366-372; Imberechts et al., *Vet. Microbiol.* 1997, 54:329-341; Marquadt et al., *FEMS Immnol. Med. Microbiol.* 1999, 23:283-288; and Kink et al., *Infect. Immun.* 1998, 66:2018-2025).

Such experiments show that the antibodies described herein provide an effective and safe antibody-based, e.g., IgY-based, therapy, e.g., oral therapy, for human patients against ESBL-producing gram negative bacteria.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

What is claimed is:

1. An antigen composition comprising a peptide mixed with an adjuvant or mixed with a pharmaceutically acceptable carrier, wherein the peptide comprises any one of:

```
TRLDRWEPELN,          (SEQ ID NO: 2)
TRLDSWEPELN,          (SEQ ID NO: 5)
TRLDHWEPELN, or       (SEQ ID NO: 6)
TRLDRYEPELN,          (SEQ ID NO: 9)
``` and wherein the peptide is between 10-20 amino acids in length.

2. The antigen composition of claim 1, wherein the adjuvant or the pharmaceutically acceptable carrier is selected from the group consisting of: bovine serum albumin (BSA), keyhole limpet hemocyanin (KLH), *Concholepas concholepas* hemocyanin (CCH), ovalbumin (OVA), Freund's complete adjuvant (FCA), Freund's incomplete adjuvant (FIA), specol, and lipopeptide Pam3Cys-Ser-(Lys)4 (PCSL).

3. The antigen composition of claim 1, wherein the peptide comprises TRLDRWEPELN (SEQ ID NO: 2).

4. A method of inducing an immune response against beta-lactamase in an avian host, the method comprising:

administering to the avian host the antigen composition of claim 1, wherein the antigen composition is administered in an amount sufficient to induce an immune response against the beta-lactamase in the avian host.

5. The method of claim 4, wherein the method further comprises recovering an egg from the avian host, and isolating IgY antibodies from the avian host egg.

* * * * *

SEQUENCE LISTING

```
<160> NUMBER OF SEQ ID NOS: 51

<210> SEQ ID NO 1
<211> LENGTH: 11
<212> TYPE: PRT
<213> ORGANISM: Escherichia coli

<400> SEQUENCE: 1

Arg Phe Pro Met Met Ser Thr Phe Lys Val Leu
1               5                   10

<210> SEQ ID NO 2
<211> LENGTH: 11
<212> TYPE: PRT
<213> ORGANISM: Escherichia coli

<400> SEQUENCE: 2

Thr Arg Leu Asp Arg Trp Glu Pro Glu Leu Asn
1               5                   10

<210> SEQ ID NO 3
<211> LENGTH: 10
<212> TYPE: PRT
<213> ORGANISM: Klebsiella pneumoniae

<400> SEQUENCE: 3

Phe Pro Met Met Ser Thr Phe Lys Val Leu
```

<210> SEQ ID NO 4
<211> LENGTH: 11
<212> TYPE: PRT
<213> ORGANISM: Escherichia coli

<400> SEQUENCE: 4

Thr Arg Leu Asp Arg Trp Glu Pro Glu Leu Asn
1               5                   10

<210> SEQ ID NO 5
<211> LENGTH: 11
<212> TYPE: PRT
<213> ORGANISM: Escherichia coli

<400> SEQUENCE: 5

Thr Arg Leu Asp Ser Trp Glu Pro Glu Leu Asn
1               5                   10

<210> SEQ ID NO 6
<211> LENGTH: 11
<212> TYPE: PRT
<213> ORGANISM: Escherichia coli

<400> SEQUENCE: 6

Thr Arg Leu Asp His Trp Glu Pro Glu Leu Asn
1               5                   10

<210> SEQ ID NO 7
<211> LENGTH: 10
<212> TYPE: PRT
<213> ORGANISM: Yersinia enterocolitica

<400> SEQUENCE: 7

Arg Leu Asp Arg Trp Glu Pro Asp Leu Asn
1               5                   10

<210> SEQ ID NO 8
<211> LENGTH: 11
<212> TYPE: PRT
<213> ORGANISM: Escherichia coli

<400> SEQUENCE: 8

Thr Arg Leu Asp Arg Trp Glu Thr Glu Leu Asn
1               5                   10

<210> SEQ ID NO 9
<211> LENGTH: 11
<212> TYPE: PRT
<213> ORGANISM: Citrobacter koseri

<400> SEQUENCE: 9

Thr Arg Leu Asp Arg Tyr Glu Pro Glu Leu Asn
1               5                   10

<210> SEQ ID NO 10
<211> LENGTH: 11
<212> TYPE: PRT
<213> ORGANISM: Pseudomonas aeruginosa

<400> SEQUENCE: 10

Thr Arg Leu Asp Arg Ile Glu Pro Asp Leu Asn
1               5                   10

```
<210> SEQ ID NO 11
<211> LENGTH: 11
<212> TYPE: PRT
<213> ORGANISM: Raoultella planticola

<400> SEQUENCE: 11

Ser Arg Leu Asp Arg Trp Glu Thr Glu Leu Asn
1               5                   10

<210> SEQ ID NO 12
<211> LENGTH: 11
<212> TYPE: PRT
<213> ORGANISM: Klebsiella pneumoniae

<400> SEQUENCE: 12

Arg Phe Pro Met Met Ser Thr Phe Lys Val Met
1               5                   10

<210> SEQ ID NO 13
<211> LENGTH: 11
<212> TYPE: PRT
<213> ORGANISM: Serratia rubidaea

<400> SEQUENCE: 13

Arg Phe Pro Met Met Ser Thr Phe Lys Val Ile
1               5                   10

<210> SEQ ID NO 14
<211> LENGTH: 11
<212> TYPE: PRT
<213> ORGANISM: Escherichia coli

<400> SEQUENCE: 14

Arg Phe Pro Met Met Ser Thr Phe Lys Val Val
1               5                   10

<210> SEQ ID NO 15
<211> LENGTH: 11
<212> TYPE: PRT
<213> ORGANISM: Klebsiella pneumoniae

<400> SEQUENCE: 15

Arg Phe Pro Leu Met Ser Thr Phe Lys Val Leu
1               5                   10

<210> SEQ ID NO 16
<211> LENGTH: 11
<212> TYPE: PRT
<213> ORGANISM: Vibrio harvey

<400> SEQUENCE: 16

Arg Phe Pro Met Met Ser Thr Phe Lys Thr Leu
1               5                   10

<210> SEQ ID NO 17
<211> LENGTH: 11
<212> TYPE: PRT
<213> ORGANISM: Escherichia coli

<400> SEQUENCE: 17

Arg Phe Pro Met Leu Ser Thr Phe Lys Val Leu
1               5                   10

<210> SEQ ID NO 18
```

```
<211> LENGTH: 11
<212> TYPE: PRT
<213> ORGANISM: Escherichia coli

<400> SEQUENCE: 18

Arg Phe Pro Met Ile Ser Thr Phe Lys Val Leu
1               5                   10

<210> SEQ ID NO 19
<211> LENGTH: 11
<212> TYPE: PRT
<213> ORGANISM: Escherichia coli

<400> SEQUENCE: 19

Arg Phe Pro Met Val Ser Thr Phe Lys Val Leu
1               5                   10

<210> SEQ ID NO 20
<211> LENGTH: 11
<212> TYPE: PRT
<213> ORGANISM: Klebsiella pneumoniae

<400> SEQUENCE: 20

Arg Phe Pro Ile Met Ser Thr Phe Lys Val Leu
1               5                   10

<210> SEQ ID NO 21
<211> LENGTH: 11
<212> TYPE: PRT
<213> ORGANISM: Klebsiella pneumoniae

<400> SEQUENCE: 21

Arg Phe Pro Met Met Asn Thr Phe Lys Val Val
1               5                   10

<210> SEQ ID NO 22
<211> LENGTH: 11
<212> TYPE: PRT
<213> ORGANISM: Klebsiella pneumoniae

<400> SEQUENCE: 22

Arg Phe Pro Met Leu Ser Thr Phe Lys Val Val
1               5                   10

<210> SEQ ID NO 23
<211> LENGTH: 11
<212> TYPE: PRT
<213> ORGANISM: Desulfovibrio desulfuricans

<400> SEQUENCE: 23

Arg Phe Pro Met Cys Ser Thr Phe Lys Val Leu
1               5                   10

<210> SEQ ID NO 24
<211> LENGTH: 11
<212> TYPE: PRT
<213> ORGANISM: Vibrio parahaemolyticus

<400> SEQUENCE: 24

Arg Phe Pro Leu Met Ser Thr Phe Lys Thr Leu
1               5                   10

<210> SEQ ID NO 25
<211> LENGTH: 11
<212> TYPE: PRT
```

```
<213> ORGANISM: Klebsiella pneumoniae

<400> SEQUENCE: 25

Arg Phe Pro Leu Met Ser Thr Phe Lys Ala Leu
1               5                   10

<210> SEQ ID NO 26
<211> LENGTH: 11
<212> TYPE: PRT
<213> ORGANISM: Klebsiella pneumoniae

<400> SEQUENCE: 26

Arg Phe Pro Met Val Ser Thr Phe Lys Val Val
1               5                   10

<210> SEQ ID NO 27
<211> LENGTH: 10
<212> TYPE: PRT
<213> ORGANISM: Escherichia coli

<400> SEQUENCE: 27

Phe Pro Met Met Ser Thr Phe Lys Val Val
1               5                   10

<210> SEQ ID NO 28
<211> LENGTH: 11
<212> TYPE: PRT
<213> ORGANISM: Klebsiella pneumoniae

<400> SEQUENCE: 28

Arg Phe Pro Val Val Ser Thr Phe Lys Val Leu
1               5                   10

<210> SEQ ID NO 29
<211> LENGTH: 11
<212> TYPE: PRT
<213> ORGANISM: Bordetella bronchiseptica

<400> SEQUENCE: 29

Arg Phe Pro Met Cys Ser Thr Phe Lys Leu Leu
1               5                   10

<210> SEQ ID NO 30
<211> LENGTH: 11
<212> TYPE: PRT
<213> ORGANISM: Pseudovibrio sp.

<400> SEQUENCE: 30

Arg Phe Pro Met Ala Ser Thr Phe Lys Ala Leu
1               5                   10

<210> SEQ ID NO 31
<211> LENGTH: 11
<212> TYPE: PRT
<213> ORGANISM: Comamonas testosteroni

<400> SEQUENCE: 31

Arg Phe Pro Met Cys Ser Thr Phe Lys Thr Leu
1               5                   10

<210> SEQ ID NO 32
<211> LENGTH: 11
<212> TYPE: PRT
<213> ORGANISM: Janthinobacterium sp.
```

<400> SEQUENCE: 32

Arg Phe Pro Leu Cys Ser Thr Phe Lys Val Met
1               5                   10

<210> SEQ ID NO 33
<211> LENGTH: 11
<212> TYPE: PRT
<213> ORGANISM: Escherichia coli

<400> SEQUENCE: 33

Ile Ala Asp Lys Ser Gly Ala Gly Glu Arg Gly
1               5                   10

<210> SEQ ID NO 34
<211> LENGTH: 11
<212> TYPE: PRT
<213> ORGANISM: Escherichia coli

<400> SEQUENCE: 34

Ile Ala Asp Lys Thr Gly Ala Gly Glu Arg Gly
1               5                   10

<210> SEQ ID NO 35
<211> LENGTH: 11
<212> TYPE: PRT
<213> ORGANISM: Salmonella enterica

<400> SEQUENCE: 35

Ile Ala Asp Lys Ser Gly Thr Gly Glu Arg Gly
1               5                   10

<210> SEQ ID NO 36
<211> LENGTH: 11
<212> TYPE: PRT
<213> ORGANISM: Escherichia coli

<400> SEQUENCE: 36

Ile Ala Asp Lys Ser Gly Ala Gly Lys Arg Gly
1               5                   10

<210> SEQ ID NO 37
<211> LENGTH: 11
<212> TYPE: PRT
<213> ORGANISM: Escherichia coli

<400> SEQUENCE: 37

Ile Ala Asp Lys Ser Gly Ala Ser Glu Arg Gly
1               5                   10

<210> SEQ ID NO 38
<211> LENGTH: 11
<212> TYPE: PRT
<213> ORGANISM: Shigella sonnei

<400> SEQUENCE: 38

Ile Ala Asp Lys Ser Gly Ala Gly Arg Arg Gly
1               5                   10

<210> SEQ ID NO 39
<211> LENGTH: 11
<212> TYPE: PRT
<213> ORGANISM: Escherichia coli

<400> SEQUENCE: 39

Ile Ala Asp Lys Ser Gly Ala Asn Glu Arg Gly
1               5                   10

<210> SEQ ID NO 40
<211> LENGTH: 11
<212> TYPE: PRT
<213> ORGANISM: Klebsiella pneumoniae

<400> SEQUENCE: 40

Ile Ala Asp Lys Ala Gly Ala Gly Glu Arg Gly
1               5                   10

<210> SEQ ID NO 41
<211> LENGTH: 11
<212> TYPE: PRT
<213> ORGANISM: Escherichia coli

<400> SEQUENCE: 41

Ile Ala Asp Lys Ser Gly Ala Asp Glu Arg Gly
1               5                   10

<210> SEQ ID NO 42
<211> LENGTH: 11
<212> TYPE: PRT
<213> ORGANISM: Escherichia coli

<400> SEQUENCE: 42

Ile Ala Asp Arg Thr Gly Ala Gly Glu Arg Gly
1               5                   10

<210> SEQ ID NO 43
<211> LENGTH: 11
<212> TYPE: PRT
<213> ORGANISM: Enterobacter aerogenes

<400> SEQUENCE: 43

Ile Ala Asp Lys Ser Gly Ala Gly Val Arg Gly
1               5                   10

<210> SEQ ID NO 44
<211> LENGTH: 11
<212> TYPE: PRT
<213> ORGANISM: Escherichia coli

<400> SEQUENCE: 44

Ile Ala Asp Lys Ser Gly Thr Gly Lys Arg Gly
1               5                   10

<210> SEQ ID NO 45
<211> LENGTH: 11
<212> TYPE: PRT
<213> ORGANISM: Citrobacter gillenii

<400> SEQUENCE: 45

Ile Ala Asp Lys Thr Gly Ala Gly Ala Arg Gly
1               5                   10

<210> SEQ ID NO 46
<211> LENGTH: 11
<212> TYPE: PRT
<213> ORGANISM: Escherichia coli

<400> SEQUENCE: 46

Ile Ala Asp Lys Thr Gly Ala Gly Lys Arg Gly
1               5                   10

<210> SEQ ID NO 47
<211> LENGTH: 11
<212> TYPE: PRT
<213> ORGANISM: Escherichia coli

<400> SEQUENCE: 47

Thr Arg Leu Gly Arg Trp Glu Pro Glu Leu Asn
1               5                   10

<210> SEQ ID NO 48
<211> LENGTH: 10
<212> TYPE: PRT
<213> ORGANISM: Mycobacterium fortuitum

<400> SEQUENCE: 48

Arg Leu Asp Arg Trp Glu Val Glu Leu Asn
1               5                   10

<210> SEQ ID NO 49
<211> LENGTH: 10
<212> TYPE: PRT
<213> ORGANISM: Escherichia coli

<400> SEQUENCE: 49

Arg Leu Asp Arg Trp Glu Leu Glu Leu Asn
1               5                   10

<210> SEQ ID NO 50
<211> LENGTH: 11
<212> TYPE: PRT
<213> ORGANISM: Escherichia coli

<400> SEQUENCE: 50

Thr Arg Leu Asp Arg Ile Glu Pro Asp Leu Asn
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: X = T or S or omitted
<220> FEATURE:
<221> NAME/KEY: MISC_FEATURE
<222> LOCATION: (5)..(5)
<223> OTHER INFORMATION: X = R, S, or H
<220> FEATURE:
<221> NAME/KEY: MISC_FEATURE
<222> LOCATION: (6)..(6)
<223> OTHER INFORMATION: X = W, Y, or I
<220> FEATURE:
<221> NAME/KEY: MISC_FEATURE
<222> LOCATION: (8)..(8)
<223> OTHER INFORMATION: X = P or T
<220> FEATURE:
<221> NAME/KEY: MISC_FEATURE
<222> LOCATION: (9)..(9)
<223> OTHER INFORMATION: X = E or D

<400> SEQUENCE: 51

Xaa Arg Leu Asp Xaa Xaa Glu Xaa Xaa Leu Asn
1               5                   10